US012662461B2

(12) United States Patent
Pagire et al.

(10) Patent No.: US 12,662,461 B2
(45) Date of Patent: Jun. 23, 2026

(54) TRICYCLIC COMPOUND AND PHARMACEUTICAL USE THEREOF

(71) Applicant: JD BIOSCIENCE INC., Buk-gu (KR)

(72) Inventors: Haushabhau Shivaji Pagire, Buk-gu (KR); Suvarna Haushabhau Pagire, Buk-gu (KR); Min Hee Kim, Buk-gu (KR); Won Mi Lee, Buk-gu (KR); Jin Hee Ahn, Buk-gu (KR); Sung Min Song, Buk-gu (KR); Heejong Lee, Buk-gu (KR); Dooseop Kim, Buk-gu (KR); Eun Young Lee, Buk-gu (KR)

(73) Assignee: JD BIOSCIENCE INC., Buk-gu (KR)

(*) Notice: Subject to any disclaimer, the term of this patent is extended or adjusted under 35 U.S.C. 154(b) by 1091 days.

(21) Appl. No.: 17/773,452

(22) PCT Filed: Oct. 30, 2020

(86) PCT No.: PCT/KR2020/015079
§ 371 (c)(1),
(2) Date: Apr. 29, 2022

(87) PCT Pub. No.: WO2021/086133
PCT Pub. Date: May 6, 2021

(65) Prior Publication Data

US 2023/0002349 A1 Jan. 5, 2023

(30) Foreign Application Priority Data

Oct. 31, 2019 (KR) ........................ 10-2019-0137775

(51) Int. Cl.
*C07D 401/06* (2006.01)
*C07D 401/14* (2006.01)

(52) U.S. Cl.
CPC ......... *C07D 401/06* (2013.01); *C07D 401/14* (2013.01)

(58) Field of Classification Search
CPC .. C07D 401/06; C07D 401/04; C07D 401/14; C07D 413/14; C07D 471/04; C07D 495/04; C07D 513/04; A61P 3/00; A61P 3/04; A61P 3/06; A61P 3/10; A61P 1/16; A61P 35/00; A61P 9/10; A61P 9/12; A61K 31/4545; A61K 31/517; A61K 31/519
USPC .......................................................... 514/279
See application file for complete search history.

(56) References Cited

U.S. PATENT DOCUMENTS

| | | | | |
|---|---|---|---|---|
| 4,282,233 | A * | 8/1981 | Vilani | |
| 5,476,856 | A | 12/1995 | Carceller et al. | |
| 5,719,148 | A | 2/1998 | Bishop | |
| 6,140,337 | A | 10/2000 | Binder et al. | |
| 6,242,458 | B1 * | 6/2001 | Bishop et al. | |

FOREIGN PATENT DOCUMENTS

| | | | | |
|---|---|---|---|---|
| CN | 102 924 430 | B | * | 10/2014 |
| EP | 0270818 | A1 | | 6/1988 |
| JP | 2016513734 | A | | 5/2016 |
| JP | 2017-128541 | A | * | 7/2017 |
| WO | 1995010516 | A1 | | 4/1995 |
| WO | WO 95/10516 | A1 | * | 4/1995 |
| WO | 2002042290 | A1 | | 5/2002 |
| WO | WO 02/42290 | A1 | * | 5/2002 |
| WO | 2014144130 | A2 | | 9/2014 |
| WO | WO 2019/169082 | A1 | * | 9/2019 |

OTHER PUBLICATIONS

Piwinski et al: "Dual Antagonists of Platelet Activating Factor and Histamine Identification of Structural Requirements For Dual Activity of N-Acyl-4-(5,6-Dihydro-11 H-Benzo[5,6] Cyclohepta-[1,2-B]Pyridin-11-Ylidene )Piperidines", J. Med. Chem., vol. 34, No. 1, Jan. 1, 1991, pp. 457-461 ("Piwinski"). (Year: 1991).*

Google Patent [English Version] JP 2017-128541 A to Tokyo Women's Medical College et al. ("JP '541A") Jul. 27, 2017. (Year: 2017).*

Lin Yan et al: "Design, Synthesis Antihistamine Eval. of N-Hydroxyalkyl Desloratadine Analogs", Med.Chem, Nov. 1, 2012, vol. 8, No. 6, pp. 1126-1132, (Year: 2012).*

Njoroge et al. "Novel Tricyclic Aminoacetyl & Sulfonamide Inhibitors Ras Farnesyl Protein Transferase", Bioorg & Med. Chem. Lett., Jan. 1, 1996, vol. 6, No. 24, pp. 2977-2982 (Year: 1996).*

Kreutner et al., "Antiallergic Activity Of Loratadine, A Non-Sedating Antihistamine", Allergy, 1987, 42, pp. 57-63 SSN0105-4538eISSN1398-9995 Online (Year: 1987).*

Google Patents [English] CN 102 924 430 B Tianjin Inst Pharm Re (Year: 2014).*

Bryce et al., "Desloratadine Inhibits Allergen-Induced Airway Inflammation And Bronchial Hyperresponsiveness And Alters T-Cell Responses In Murine Models Of Asthma", J Allergy Clin Immunol, vol. 112, No. 1, (Jul. 2003) pp. 1149-1158. (Year: 2003).*

(Continued)

*Primary Examiner* — Kortney L. Klinkel
*Assistant Examiner* — Grace Ching Hsu
(74) *Attorney, Agent, or Firm* — COZEN O'CONNOR

(57) ABSTRACT

A compound of the present invention, which is a tricyclic derivative represented by chemical formula 1 or a pharmaceutically acceptable salt thereof, has an excellent inhibitory effect on serotonin activity and a pharmaceutical composition comprising same can be thus advantageously used for preventing or treating a metabolic disease associated with serotonin activation, etc.

7 Claims, No Drawings

(56) References Cited

OTHER PUBLICATIONS

PubChem CID 11961794 Compound Summary: CAS RN No. 100643-71-8 (Date Created Dec. 11, 2006; Date Modify Sep. 27, 2025); (Year: 2025).*
Liu et al., "Design and synthesis of thiourea derivatives containing a benzo[5,6]cyclohepta[1,2-b]pyridine moiety as potential antitumor and anti-inflammatory agents", Bioorganic & Medicinal Chemistry Letters., vol. 22, pp. 2701-2704 (2012).
Lin et al., "Design, Synthesis and Antihistamine Evaluations of Several N-hydroxyalkyl Desloratadine Analogues", Medicinal Chemistry, Vo. 8, pp. 1126-1132 (2012).
Bosma et al., "Route to Prolonged Residence Time at the Histamine $H_1$ Receptor: Growing from Desloratadine to Rupatadine" Journal of Medical Chemistry, vol. 62 , (2019), pp. 6630-6644.
International Application No. PCT/KR2020/015079, "International Search Report", mailed Feb. 9, 2021, 9 pages.
Sarrouilhe et al., "Serotonin and Cancer: What Is the Link?", Current Molecular Medicine, (2015), vol. 15, pp. 62-77.
Lin et al., "Design, synthesis and biological activity evaluation of desloratadine analogues as $H_1$ receptor antagonists", Bioorganic & Medicinal Chemistry, (2013), vol. 21, pp. 4178-4185.
Njoroge et al., "Novel tricyclic aminoacetyl and sulfonamide inhibitors of Ras farnesyl protein transferase", Bioorganic & Medicinal Chemistry Letters, (1996), vol. 6, No. 24, pp. 2977-2982.
Oh et al., "Regulation of systemic energy homeostasis by serotonin in adipose tissues", Nature Communications, 6:6794 (2015), pp. 1-12.
Ruddell et al., "A Role for Serotonin (5-HT) in Hepatic Stellate Cell Function and Liver Fibrosis", The American Journal of Pathology, (2006), vol. 169, No. 3, pp. 861-876.
Kim et al., "5-$HT_{2A}$ receptor antagonists inhibit hepatic stellate cell activation and facilitate apoptosis", Liver International, (2013), vol. 33, pp. 535-543.
Choi et al., "Serotonin signals through a gut-liver axis to regulate hepatic steatosis", Nature Communications, 9:4824 (2018), pp. 1-9.
Piwinski et al., "Dual antagonists of platelet activating factor and histamine. Identification of structural requirements for dual activity of N-acyl-4-(5,6-dihydro-11H-benzo[5,6]cyclohepta-[I,2-b]pyridin-11-ylidene)piperidines", Journal of Medicinal Chemistry, (1991) vol. 34, No. 1, p. 457-461.

* cited by examiner

TRICYCLIC COMPOUND AND PHARMACEUTICAL USE THEREOF

This is a national stage application, filed under 35 U.S.C. § 371, of International Patent Application No. PCT/KR2020/015079, filed on Oct. 30, 2020, which claims priority to KR Application No. 10-2019-0137775, filed on Oct. 31, 2019, which are incorporated by reference herein in their entirety.

TECHNICAL FIELD

The present invention relates to a tricyclic compound that acts as a serotonin receptor antagonist, and a pharmaceutical use thereof for metabolic diseases or the like. More specifically, the present invention relates to a tricyclic compound that acts as a serotonin 2A receptor antagonist, and a pharmaceutical use for the treatment of obesity, fatty liver, steatohepatitis, or the like including the same.

BACKGROUND ART

Obesity refers to a condition in which an excessive amount of body fat is accumulated in the body. Obesity is caused by the accumulation of extra energy in the form of body fat when calories burned are less than calories taken in. Causes of obesity include irregular eating habits, excessive food intake, a lack of exercise, a genetic factor, or a psychological factor. Obesity shows symptoms such as cardiovascular diseases, hypertension, sleep apnea, dyslipidemia, hyperinsulinemia, and osteoarthritis, in addition to a breathless symptom and arthralgia.

The purpose of obesity treatment is the prevention and treatment of obesity-related complications. The most basic treatment method for obesity is lifestyle changes, and in the case of drug treatment, an appetite suppressant is mainly used. However, such an appetite suppressant acts on the central nervous system, and thus has side effects, for example, mental diseases such as depression.

The appetite suppressant regulates serotonin (5-HT) in the central nervous system, and the serotonin is a neurotransmitter that regulates mood, sleep, or appetite. Serotonin acts not only on the central nervous system but also on peripheral tissues and has been reported to play an important role in metabolic regulation in peripheral tissues. Serotonin cannot cross the blood brain barrier, and thus serotonin in the central nervous system and serotonin in peripheral tissues are considered to be an independent system.

It is known that when the synthesis of serotonin in peripheral tissues is inhibited, energy is burned by reducing lipogenesis in white adipocytes and generating heat in brown adipocytes (Oh C et al., Nature Communication 6, 6794, 2015).

Meanwhile, fatty liver refers to a disease caused by an increase in the fat content in the liver due to the accumulation of a large amount of fat in hepatocytes. Fatty liver is roughly divided into alcoholic fatty liver and non-alcoholic fatty liver. Excessive alcohol intake accumulates fat in hepatocytes, and metabolites of alcohol damage hepatocytes. However, non-alcoholic fatty liver refers to a disease in which fat is accumulated in the liver despite not drinking alcohol or drinking a small amount of alcohol.

Fatty liver includes various forms of liver diseases, from simple fatty liver in which only fat is accumulated, and hepatocytes are not damaged, to steatohepatitis in which hepatocyte damage persists, and liver cirrhosis accompanied by ascites, jaundice, or the like. Fatty liver is caused by the accumulation of neutral fat in hepatocytes, and the size of the blister of the accumulated neutral fat increases over time. Such a fat blister increases the inflammatory response to induce hepatitis or liver fibrosis.

The treatment of fatty liver includes body weight loss through diet and exercise therapy, and in the case of drug treatment, a diabetes-treating agent that improves insulin resistance is used for short-term treatment. However, the agent is used for short-term treatment, and the long-term treatment effects of the agent have not been reported so far. Moreover, commercially available lipid improvers or hepatoprotective agents are only meaningful for maintenance, not treatment.

According to recent studies, when a serotonin receptor antagonist was treated in liver-damaged mice, the serotonin receptor antagonist inhibited the proliferation of damaged hepatocytes and increased the rate of apoptosis (Ruddell et al., The American Journal of Pathology, 169(3), 861-876, 2006 September). Moreover, when ketanserin and sarpogrelate, which are serotonin receptor inhibitors, were treated, the viability of liver-damaged cells in LX-2 cells was reduced and apoptosis was induced (Kim et al., Liver International, 33(4), 535-543, 2013). Furthermore, serotonin receptor 2A (HTR2A) liver-specific knockout mice were produced, and the amelioration of hepatic steatosis and the reduction of inflammation and fibrosis-related genes were confirmed (Choi et al., Nature Communications, 9, 4824, 2018).

PRIOR ART DOCUMENTS (Non-patent document 1) Oh C et al., Nature Communications, 6, 6794, 2015

(Non-patent document 2) Ruddell et al., The American Journal of Pathology, 169(3), 861-876, 2006 September (Non-patent document 3) Kim et al., Liver International, 33(4), 535-543, 2013

(Non-patent document 4) Choi et al., Nature Communications, 9, 4824, 2018

DISCLOSURE OF INVENTION

Technical Problem

For the treatment of obesity, it is important to inhibit the synthesis of serotonin present in the peripheral nervous system. Accordingly, the present inventors have tried to find serotonin receptors associated with obesity in peripheral tissues, and as a result, it was confirmed that the expression of a serotonin 2A ($5\text{-}HT_{2A}$) receptor is increased in the obese state. Moreover, it was confirmed that body weight can be reduced, and fatty liver, steatohepatitis and fibrosis of the liver can be ameliorated by knocking out the serotonin 2A receptor.

Therefore, an object of the present invention is to provide a compound that acts as a serotonin receptor antagonist, and a pharmaceutical use thereof for diseases associated with serotonin activation.

Solution to Problem

Accordingly, the present invention provides a compound which is a tricyclic derivative represented by Chemical Formula 1 or a pharmaceutically acceptable salt, stereoisomer, or prodrug thereof.

Moreover, the present invention provides a pharmaceutical composition for preventing or treating diseases associated with serotonin activation, the pharmaceutical composition containing the compound according to the present invention as an active ingredient.

Advantageous Effects of Invention

The compound, which is a tricyclic derivative or a pharmaceutically acceptable salt, stereoisomer, or prodrug thereof, according to the present invention can exhibit an excellent antagonistic effect on serotonin receptor, in particular, serotonin 2A receptor.

Therefore, the compound according to the present invention can be usefully used for the prevention or treatment of diseases associated with serotonin activation, for example, metabolic diseases such as obesity, fatty liver and steatohepatitis.

BEST MODE FOR CARRYING OUT THE INVENTION

Hereinafter, the present invention will be described in detail.

The term "halogen" in the present specification refers to F, Cl, Br, or I, unless otherwise noted.

The term "alkyl" refers to a linear or branched saturated hydrocarbon residue, unless otherwise noted. For example, "$C_{1-10}$ alkyl" refers to alkyl having a skeleton consisting of 1 to 10 carbon atoms. Specifically, $C_{1-10}$ alkyl may be methyl, ethyl, n-propyl, i-propyl, n-butyl, i-butyl, t-butyl, n-pentyl, i-pentyl, t-pentyl, sec-pentyl, neopentyl, hexyl, heptyl, octyl, nonyl, decyl, or the like.

The term "alkoxy" refers to a linear or branched alkyl-oxy residue, unless otherwise noted. For example, "$C_{1-6}$ alkoxy" refers to alkyl-oxy having a skeleton consisting of 1 to 6 carbon atoms. Specifically, $C_{1-6}$ alkoxy may include methoxy, ethoxy, n-propoxy, i-propoxy, n-butoxy, i-butoxy, t-butoxy, n-pentoxy, i-pentoxy, t-pentoxy, sec-pentoxy, neopentoxy, hexyloxy, or the like.

The term "haloalkyl" or "haloalkoxy" refers to alkyl or alkoxy substituted with one or more halogens. Specifically, haloalkyl or haloalkoxy may be alkyl or alkoxy substituted with one or more homogeneous or heterogeneous halogens.

The term "cycloalkyl" refers to a saturated monocycle or polycycle containing only carbon atoms in a ring. For example, cycloalkyl may be a monocycle and have 3 to 7 carbon atoms.

In one aspect, the present invention provides a compound which is a tricyclic derivative represented by Chemical Formula 1 or a pharmaceutically acceptable salt, stereoisomer, or prodrug thereof.

[Chemical Formula 1]

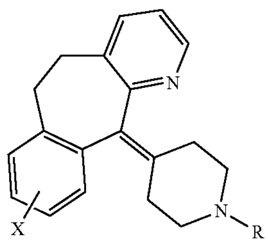

In the formula,

X is H, a halogen, $C_{1-6}$ alkyl, or $C_{1-6}$ alkoxy;

R is H, $C_{1-10}$ alkyl, -A, $-L^1-R^1$, $-L^1-A$, $-L^1-L^2-A$, or $-L^1-L^2-L^3-A$;

$L^1$ is $-(CH_2)_n-$, $-C(=O)-$, $-C(=O)-O-$, $-CH(-OH)-CH_2-$, $-S(=O)_2-$, or $-C(=S)-NH-$;

$L^2$ is $-O-$, $-C(=O)-$, $-CH(-OH)-$, $-CH_2-CH(-NH_2)-$,

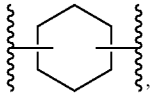, or 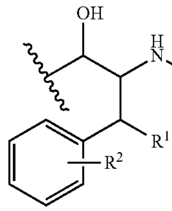 ;

$L^3$ is $-C(=O)-$, $-(CH_2)_n-$, or $-(CH_2)_n-O-$;

n's are each an integer of 1 to 6;

A is

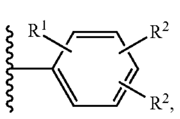 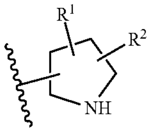 , 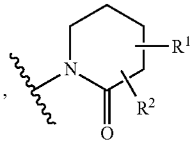 ,

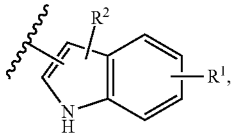 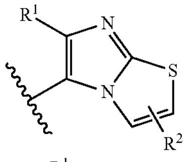 ,

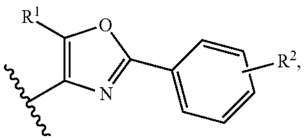 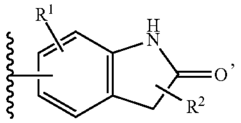

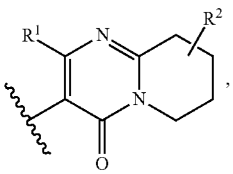 , 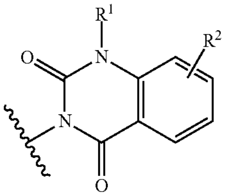 ,

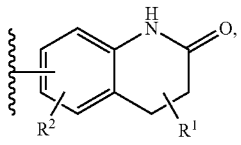 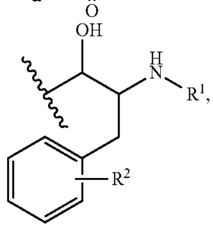

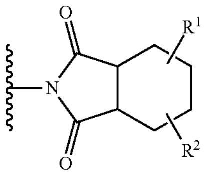 , 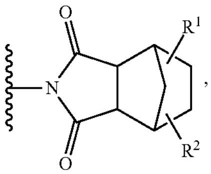 ,

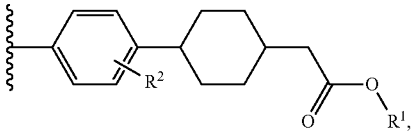

-continued

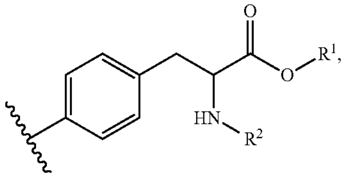

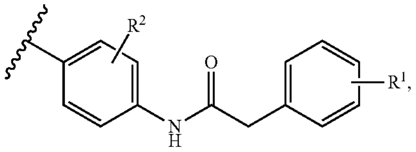

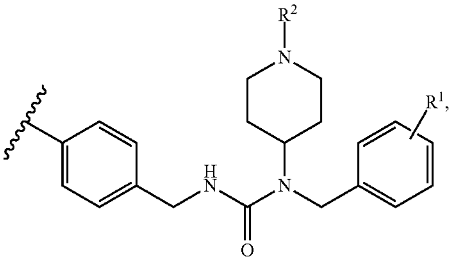

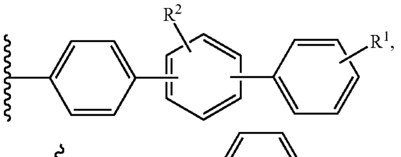

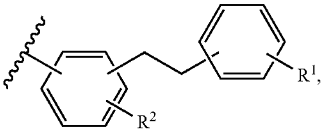

or

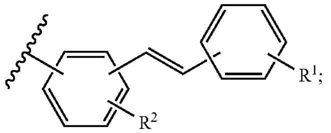

and $R^1$ and $R^2$ are each independently H, a halogen, —OH, halo $C_{1-6}$ alkyl, $C_{1-6}$ alkoxy, halo $C_{1-6}$ alkoxy, —CN, —COOH, $C_{1-6}$ alkyl, allyl, $C_{3-6}$ cycloalkyl, amino, —NH—C(═O)—$C_{1-6}$ alkyl, —NH—C(═O)—$C_{1-6}$ alkoxy, —C(═O)—$C_{1-6}$ alkoxy, or

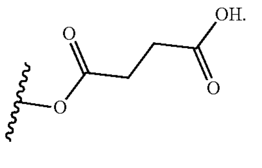 [SMILES: *OC(=O)CCC(=O)O]

In Chemical Formula 1, the substitution position of the X group may be carbon 7, 8, 9, or 10 in 5,6-dihydro-11H-benzo[5,6]cyclohepta[1,2-b]pyridine.

Examples of various substitution positions of the X group include Chemical Formulae 1-1 to 1-4.

1-1

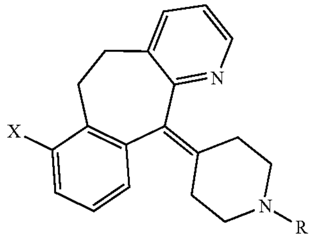

1-2

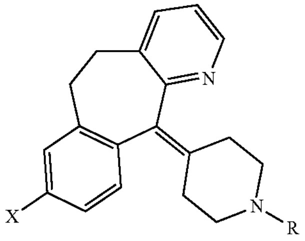

1-3

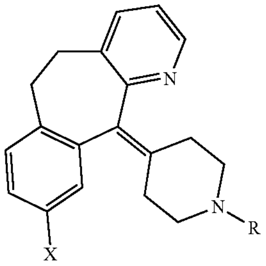

1-4

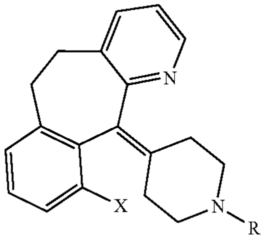

According to one embodiment, in Chemical Formula 1, R is H, $C_{1-10}$ alkyl, or -$L^1$-$R^1$; L is —$(CH_2)_n$—, —C(═O)—, —C(═O)—O—, —S(═O)$_2$—, or —C(═S)—NH—; n is an integer of 1 to 6; and $R^1$ is —OH or $C_{1-3}$ alkyl.

According to another embodiment, in Chemical Formula 1, R is -A, -$L^1$-A, -$L^1$-$L^2$-A, or -$L^1$-$L^2$-$L^3$-A; $L^1$ is —$(CH_2)_n$— or —C(═O)—; $L^2$ is —O— or

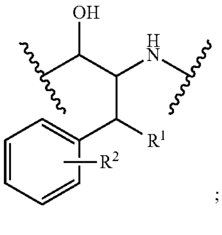

;

$L^3$ is —C(=O)—; n is an integer of 1 to 6; A is

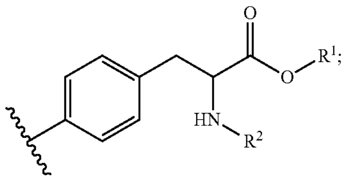

and $R^1$ and $R^2$ are each independently H, —Cl, or $C_{1-3}$ alkyl.

According to still another embodiment, in Chemical Formula 1, R is $-L^1-R^1$, $-L^1-L^2-A$, or $-L^1-L^2-L^3-A$; $L^1$ is $—(CH_2)_n—$; $L^2$ is —CH(—OH)— or

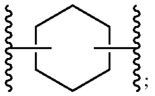

$L^3$ is $—(CH_2)_n—$; n's are each an integer of 1 to 6; A is

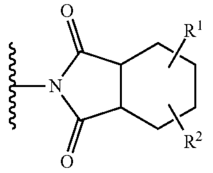

or

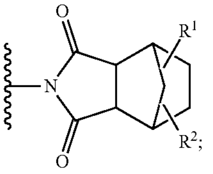

and $R^1$ and $R^2$ are both H.

According to still another embodiment, in Chemical Formula 1, R is $-L^1-L^2-A$ or $-L^1-L^2-L^3-A$; $L^1$ is $—(CH_2)_n—$ or —C(=O)—; $L^2$ is —O—, —CH(—OH)—, or

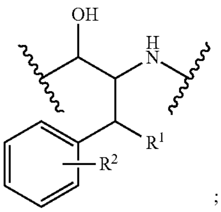

;

$L^3$ is —C(=O)— or $—(CH_2)_n—O—$; n's are each an integer of 1 to 6; A is

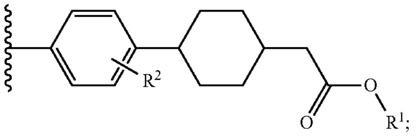

and $R^1$ and $R^2$ are each independently H or $C_{1-3}$ alkyl.

According to still another embodiment, in Chemical Formula 1, R is -A, $-L^1-A$, $-L^1-L^2-A$, or $-L^1-L^2-L^3-A$; $L^1$ is $—(CH_2)_n—$ or —C(=O); $L^2$ is —O—, —C(=O)—, —CH(—OH)—, $—CH_2—CH(—NH_2)—$, or

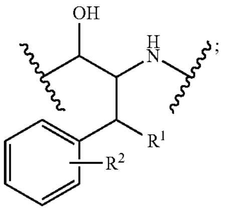

$L^3$ is —C(=O)— or $—(CH_2)_n—$; n's are each an integer of 1 to 6; A is

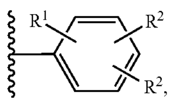

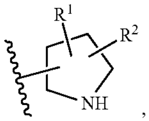

,

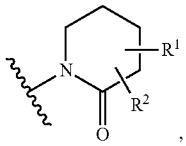

,

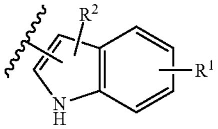

,

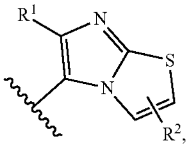

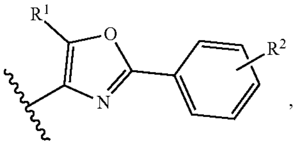

,

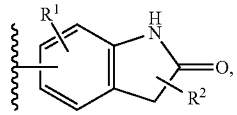

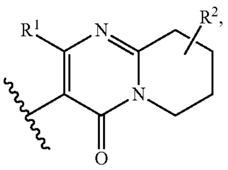

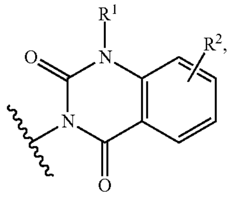

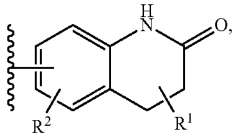

or

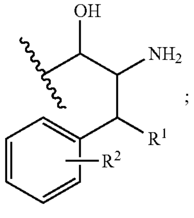

;

and $R^1$ and $R^2$ are each independently H, —F, —Cl, —Br, —OH, $—CF_3$, —CN, —COOH, or $C_{1-3}$ alkyl.

According to still another embodiment, in Chemical Formula 1, R is $-L^1-L^2-A$ or $-L^1-L^2-L^3-A$; $L^1$ is $—(CH_2)_n—$; $L^2$ is —O— or —CH(—OH)—; $L^3$ is $—(CH_2)_n—O—$; A is

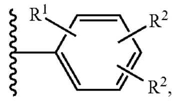

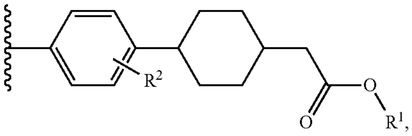

-continued

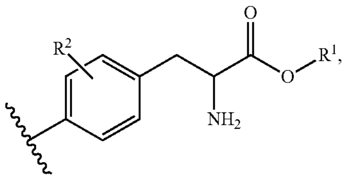

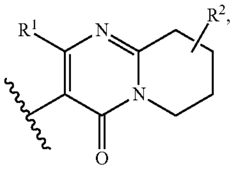

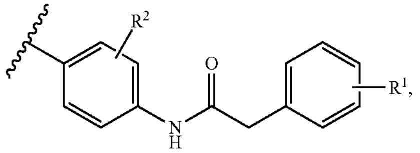

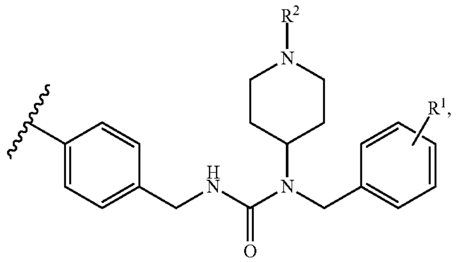

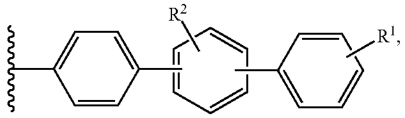

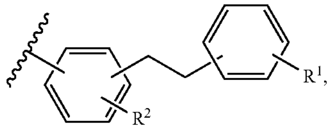

or

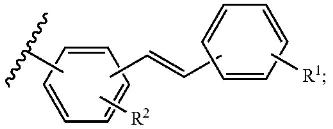

and $R^1$ and $R^2$ are each independently H, F, $C_{1-6}$ alkyl, $C_{1-6}$ alkoxy, —$CF_3$, allyl, —COOH, $C_{3-6}$ cycloalkyl, amino, —C(=O)—$C_{1-6}$ alkoxy, or

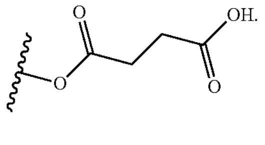 [SMILES: *OC(=O)CCC(=O)O]

According to one specific embodiment, the tricyclic derivative may be represented by Chemical Formula 1a.

[Chemical Formula 1a]

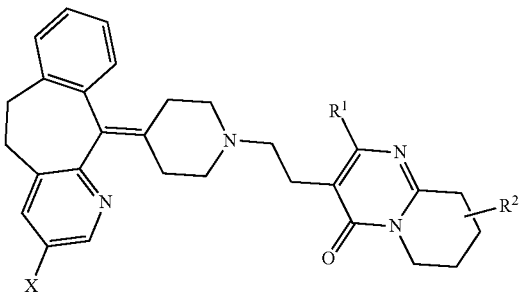

In the formula,

X is H, a halogen, $C_{1-6}$ alkyl, or $C_{1-6}$ alkoxy; and $R^1$ and $R^2$ are each independently H, a halogen, —OH, $C_{1-6}$ alkyl, halo $C_{1-6}$ alkyl, or $C_{1-6}$ alkoxy.

According to another specific embodiment, the tricyclic derivative may be represented by Chemical Formula 1b.

[Chemical Formula Ib]

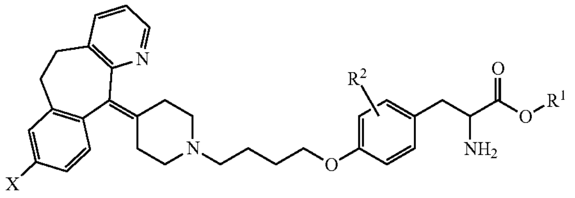

In the formula,

X is H, a halogen, $C_{1-6}$ alkyl, or $C_{1-6}$ alkoxy; and $R^1$ and $R^2$ are each independently H, a halogen, —OH, $C_{1-6}$ alkyl, halo $C_{1-6}$ alkyl, or $C_{1-6}$ alkoxy.

According to still another specific embodiment, the tricyclic derivative may be represented by Chemical Formula 1c.

[Chemical Formula 1c]

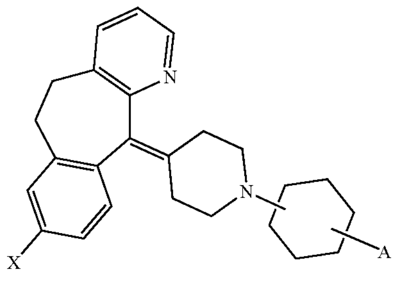

In the formula,

X is H, a halogen, $C_{1-6}$ alkyl, or $C_{1-6}$ alkoxy;

A is

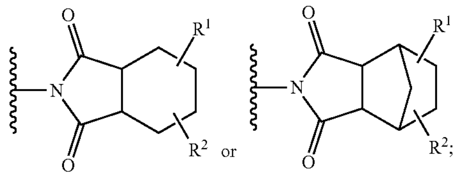

and $R^1$ and $R^2$ are each independently H, a halogen, —OH, $C_{1-6}$ alkyl, halo $C_{1-6}$ alkyl, or $C_{1-6}$ alkoxy.

The compound according to the present invention includes a pharmaceutically acceptable salt of the tricyclic derivative represented by Chemical Formula 1.

The pharmaceutically acceptable salt is required to have low toxicity to humans and not to have any negative effect on the biological activity and physicochemical properties of the parent compound. For example, the pharmaceutically acceptable salt may be an acid addition salt that is formed using a pharmaceutically acceptable free acid.

An inorganic acid or an organic acid may be used as the free acid, and here, the inorganic acid may be hydrochloric acid, sulfuric acid, nitric acid, phosphoric acid, perchloric acid, bromic acid, or the like, and the organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, or the like.

The acid addition salt may be prepared by a conventional method, for example, by dissolving a compound represented by Chemical Formula 1 in an excessive amount of an acid aqueous solution and precipitating the salt using a water-miscible organic solvent, for example, methanol, ethanol, acetone, or acetonitrile.

Moreover, the pharmaceutically acceptable salt may be an alkali metal salt (sodium salt or the like) or an alkaline earth metal salt (potassium salt or the like). The alkali metal salt or the alkaline earth metal salt can be obtained, for example, by dissolving a compound represented by Chemical Formula 1 in an excessive amount of an alkali metal hydroxide or alkaline earth metal hydroxide solution, filtering an undissolved compound salt, and evaporating and drying the filtrate.

In addition, the compound according to the present invention may have a chiral carbon center, and thus may be present in the form of an R- or S-isomer, a racemic compound, individual enantiomers or mixtures thereof, or individual diastereomers or mixtures thereof, and all such stereoisomers and mixtures thereof may fall within the scope of the present invention.

Moreover, the compound according to the present invention may include a prodrug of the compound represented by Chemical Formula 1. The prodrug may refer to a functional derivative of the compound and is easily convertible to the compound in vivo. The prodrug may be more easily administered than the compound in some situations and is thus useful in some cases. The prodrug is bioavailable, for example, through oral administration, unlike the compound. The prodrug may also have improved solubility in a pharmaceutical composition, compared to the compound. The prodrug can also be converted to the corresponding drug by various mechanisms, including enzymatic processes and metabolic hydrolysis. An example of the prodrug is a compound in which an amino group of the compound is protected with a protecting group such as t-butyloxycarbonyl (Boc).

Furthermore, the compound according to the present invention may include a hydrate or solvate of the compound represented by Chemical Formula 1. The hydrate or solvate may be prepared using a known method and is preferably non-toxic and water-soluble. In particular, preferably, the hydrate or solvate may be one in which one to five molecules of water or an alcoholic solvent (in particular, ethanol or the like) are bound.

According to the specific embodiment, specific examples of the compound according to the present invention are as follows:

1) ethyl 4-(8-chloro-5,6-dihydro-11H-benzo[5,6]cyclohepta[1,2-b]pyridin-11-ylidene)piperidine-1-carboxylate;

2) 8-chloro-11-(piperidin-4-ylidene)-6,11-dihydro-5H-benzo[5,6]cyclohepta[1,2-b]pyridine dihydrochloride;

3) 8-chloro-11-(1-(methylsulfonyl)piperidin-4-ylidene)-6,11-dihydro-5H-benzo[5,6]cyclohepta[1,2-b]pyridine;

4) 4-(8-chloro-5,6-dihydro-11H-benzo[5,6]cyclohepta[1,2-b]pyridin-11-ylidene)-N-isopropylpiperidine-1-carbothioamide;

5) 1-(4-(8-chloro-5,6-dihydro-11H-benzo[5,6]cyclohepta[1,2-b]pyridin-11-ylidene)piperidin-1-yl)ethan-1-one;

6) (R)-3-amino-1-(4-(8-chloro-5,6-dihydro-11H-benzo[5,6]cyclohepta[1,2-b]pyridin-11-ylidene)piperidin-1-yl)-4-(2,4,5-trifluorophenyl)butan-1-one dihydrochloride;

7) (S)-2-amino-3-(4-(4-(8-chloro-5,6-dihydro-11H-benzo[5,6]cyclohepta[1,2-b]pyridin-11-ylidene)piperidine-1-carbonyl)phenyl)propionic acid dihydrochloride;

8) (S)-1-(2-amino-4-(4-(8-chloro-5,6-dihydro-11H-benzo[5,6]cyclohepta[1,2-b]pyridin-11-ylidene)piperidin-1-yl)-4-oxobutyl)-5,5-difluoropiperidin-2-one dihydrochloride;

9) 3-(2-(4-(8-chloro-5,6-dihydro-11H-benzo[5,6]cyclohepta[1,2-b]pyridin-11-ylidene)piperidin-1-yl)ethyl)-2-methyl-6,7,8,9-tetrahydro-4H-pyrido[1,2-a]pyrimidin-4-one;

10) 3-(2-(4-(8-chloro-5,6-dihydro-11H-benzo[5,6]cyclohepta[1,2-b]pyridin-11-ylidene)piperidin-1-yl)ethyl)-9-hydroxy-2-methyl-6,7,8,9-tetrahydro-4H-pyrido[1,2-a]pyrimidin-4-one;

11) 2-(4-(8-chloro-5,6-dihydro-11H-benzo[5,6]cyclohepta[1,2-b]pyridin-11-ylidene)piperidin-1-yl)-1-(6-methylimidazo[2,1-b]thiazol-5-yl)ethan-1-one;

12) 3-(2-(4-(8-chloro-5,6-dihydro-11H-benzo[5,6]cyclohepta[1,2-b]pyridin-11-ylidene)piperidin-1-yl)ethyl)quinazoline-2,4(1H,3H)-dione;

13) 8-chloro-11-(1-methylpiperidin-4-ylidene)-6,11-dihydro-5H-benzo[5,6]cyclohepta[1,2-b]pyridine;

14) (S)-2-amino-3-(4-(4-(4-(8-chloro-5,6-dihydro-11H-benzo[5,6]cyclohepta[1,2-b]pyridin-11-ylidene)piperidin-1-yl)butoxy)phenyl)propionic acid trihydrochloride;

15) 2-(4-(8-chloro-5,6-dihydro-11H-benzo[5,6]cyclohepta[1,2-b]pyridin-11-ylidene)piperidin-1-yl)-1-(6-methylimidazo[2,1-b]thiazol-5-yl)ethan-1-ol;

16) ethyl (S)-2-((t-butoxycarbonyl)amino)-3-(4-(4-(4-(8-chloro-5,6-dihydro-11H-benzo[5,6]cyclohepta[1,2-b]pyridin-11-ylidene)piperidin-1-yl)butoxy)phenyl)propanoate;

17) (S)-2-((t-butoxycarbonyl)amino)-3-(4-(4-(4-(8-chloro-5,6-dihydro-11H-benzo[5,6]cyclohepta[1,2-b]pyridin-11-ylidene)piperidin-1-yl)butoxy)phenyl)propionic acid;

18) 7-(4-(4-(8-chloro-5,6-dihydro-11H-benzo[5,6]cyclohepta[1,2-b]pyridin-11-ylidene)piperidin-1-yl)butoxy)-3,4-dihydroquinolin-2(1H)-one;

19) 2-(4-(4-(8-chloro-5,6-dihydro-11H-benzo[5,6]cyclohepta[1,2-b]pyridin-11-ylidene)piperidin-1-yl)butyl)hexahydro-1H-isoindole-1,3(2H)-dione;

20) (S)-2-amino-3-(3-chloro-4-(4-(4-(8-chloro-5,6-dihydro-11H-benzo[5,6]cyclohepta[1,2-b]pyridin-11-ylidene)piperidin-1-yl)butoxy)phenyl)propionic acid trihydrochloride;

21) (S)-2-amino-3-(3-chloro-4-(3-(4-(8-chloro-5,6-dihydro-11H-benzo[5,6]cyclohepta[1,2-b]pyridin-11-ylidene)piperidin-1-yl)propoxy)phenyl)propionic acid trihydrochloride;

22) (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propionic acid trihydrochloride;

23) (2S,4S)-4-(4-(8-chloro-5,6-dihydro-11H-benzo[5,6]cyclohepta[1,2-b]pyridin-11-ylidene)piperidin-1-yl)pyrrolidine-2-carboxylic acid trihydrochloride;

24) 1-(4-bromophenyl)-2-(4-(8-chloro-5,6-dihydro-11H-benzo[5,6]cyclohepta[1,2-b]pyridin-11-ylidene)piperidin-1-yl)ethan-1-one;

25) (4R,7S)-2-(((1S,2S)-2-((4-(8-chloro-5,6-dihydro-11H-benzo[5,6]cyclohepta[1,2-b]pyridin-11-ylidene)piperidin-1-yl)methyl)cyclohexyl)methyl)hexahydro-1H-4,7-methanoisoindole-1,3(2H)-dione;

26) 2-(((1S,2S)-2-((4-(8-chloro-5,6-dihydro-11H-benzo[5,6]cyclohepta[1,2-b]pyridin-11-ylidene)piperidin-1-yl)methyl)cyclohexyl)methyl)hexahydro-1H-isoindole-1,3(2H)-dione;

27) 1-(4-bromophenyl)-2-(4-(8-chloro-5,6-dihydro-11H-benzo[5,6]cyclohepta [1,2-b]pyridin-11-ylidene)piperidin-1-yl)ethan-1-ol;

28) (2S,4R)-4-(4-(8-chloro-5,6-dihydro-11H-benzo[5,6]cyclohepta[1,2-b]pyridin-11-ylidene)piperidin-1-yl)pyrrolidine-2-carboxylic acid;

29) (S)-2-amino-3-(4-(4-(8-chloro-5,6-dihydro-11H-benzo[5,6]cyclohepta[1,2-b]pyridin-11-ylidene)piperidin-1-yl)phenyl)propionic acid dihydrochloride;

30) (4R,7S)-2-(4-(4-(8-chloro-5,6-dihydro-11H-benzo[5,6]cyclohepta[1,2-b]pyridin-11-ylidene)piperidin-1-yl)butyl)hexahydro-1H-4,7-methanoisoindole-1,3(2H)-dione;

31) ethyl (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propanoate trihydrochloride;

32) 4-(4-(8-chloro-5,6-dihydro-11H-benzo[5,6]cyclohepta[1,2-b]pyridin-11-ylidene)piperidin-1-yl)butan-1-ol;

33) 3-(4-(4-(8-chloro-5,6-dihydro-11H-benzo[5,6]cyclohepta[1,2-b]pyridin-11-ylidene)piperidin-1-yl)butyl)-1H-indole-5-carbonitrile;

34) t-butyl ((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)carbamate;

35) (2R,3S)-3-amino-1-(4-(8-chloro-5,6-dihydro-11H-benzo[5,6]cyclohepta[1,2-b]pyridin-11-ylidene)piperidin-1-yl)-4-phenylbutan-2-ol;

36) trans-methyl 2-(-4-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)cyclohexyl)acetate;

37) 2-(3-(4-(8-chloro-5,6-dihydro-11H-benzo[5,6]cyclohepta[1,2-b]pyridin-11-ylidene)piperidin-1-yl)-2-hydroxypropyl)hexahydro-1H-isoindole-1,3(2H)-dione;

38) (4R,7S)-2-(3-(4-(8-chloro-5,6-dihydro-11H-benzo[5,6]cyclohepta[1,2-b]pyridin-11-ylidene)piperidin-1-yl)-2-hydroxypropyl)hexahydro-1H-4,7-methanoisoindole-1,3(2H)-dione;

39) 6-chloro-5-(2-(4-(8-chloro-5,6-dihydro-11H-benzo[5,6]cyclohepta[1,2-b]pyridin-11-ylidene)piperidin-1-yl)ethyl)indolin-2-one;

40) trans-methyl 2-(-4-(4-(4-(4-(8-chloro-5,6-dihydro-11H-benzo[5,6]cyclohepta[1,2-b]pyridin-11-ylidene)piperidin-1-yl)butoxy)phenyl)cyclohexyl)acetate;

41) trans-2-(4-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)cyclohexyl)acetic acid;

42) trans-2-(4-(4-(4-(4-(8-chloro-5,6-dihydro-11H-benzo[5,6]cyclohepta[1,2-b]pyridin-11-ylidene)piperidin-1-yl)butoxy)phenyl)cyclohexyl)acetic acid;

43) (S)-2-((t-butoxycarbonyl)amino)-3-(4-(((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)carbamoyl)phenyl)propionic acid;

44) (S)-2-amino-3-(4-(((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)carbamoyl)phenyl)propionic acid trihydrochloride;

45) trans-2-(4-(4-(((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)carbamoyl)phenyl)cyclohexyl)acetic acid;

46) N-((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)-2-phenyl-5-(trifluoromethyl)oxazole-4-carboxamide;

47) (4R,7S)-2-(3-(4-(8-chloro-5,6-dihydro-11H-benzo[5,6]cyclohepta[1,2-b]pyridin-11-ylidene)piperidin-1-yl)propyl)hexahydro-1H-4,7-methanoisoindole-1,3(2H)-dione;

48) 8-chloro-11-(piperidin-4-ylidene)-6,11-dihydro-5H-benzo[5,6]cyclohepta[1,2-b]pyridine;

49) isopropyl (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propanoate trihydrochloride;

50) neopentyl (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propanoate trihydrochloride;

51) cyclopentyl (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propanoate trihydrochloride;

52) 4-((3-(2-(4-(8-chloro-5,6-dihydro-11H-benzo[5,6]cyclohepta[1,2-b]pyridin-11-ylidene)piperidin-1-yl)ethyl)-2-methyl-4-oxo-6,7,8,9-tetrahydro-4H-pyrido[1,2-a]pyrimidin-9-yl)oxy)-4-oxobutanoic acid;

53) 2-((1R,4R)-4-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)cyclohexyl)acetic acid;

54) 4-(3-(4-(8-chloro-5,6-dihydro-11H-benzo[5,6]cyclohepta[1,2-b]pyridin-11-ylidene)piperidin-1-yl)-2-hydroxypropoxy)-4"-(trifluoromethoxy)-[1,1':3',1"-terphenyl]-5'-carboxylic acid;

55) (2S)-2-amino-3-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)propionic acid trihydrochloride;

56) 3-(4-(3-(4-(8-chloro-5,6-dihydro-11H-benzo[5,6]cyclohepta[1,2-b]pyridin-11-ylidene)piperidin-1-yl)propoxy)benzyl)-1-(4-fluorobenzyl)-1-(1-methylpiperidin-4-yl)urea;

57) N-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)acetamide;

58) t-butyl (4-(3-(4-(8-chloro-5,6-dihydro-11H-benzo[5,6]cyclohepta[1,2-b]pyridin-11-ylidene)piperidin-1-yl)-2-hydroxypropoxy)phenyl)carbamate;

59) N-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)-2-(4-fluorophenyl)acetamide;

60) 1-(4-(8-chloro-5,6-dihydro-11H-benzo[5,6]cyclohepta[1,2-b]pyridin-11-ylidene)piperidin-1-yl)-3-(2-(3-methoxyphenethyl)phenoxy)propan-2-ol;

61) 1-(2-allylphenoxy)-3-(4-(8-chloro-5,6-dihydro-11H-benzo[5,6]cyclohepta[1,2-b]pyridin-11-ylidene)piperidin-1-yl)propan-2-ol;

62) (E)-1-(4-(8-chloro-5,6-dihydro-11H-benzo[5,6]cyclohepta[1,2-b]pyridin-11-ylidene)piperidin-1-yl)-3-(2-(3-methoxystyryl)phenoxy)propan-2-ol;

63) 9-hydroxy-3-(2-(4-(8-methoxy-5,6-dihydro-11H-benzo[5,6]cyclohepta[1,2-b]pyridin-11-ylidene)piperidin-1-yl)ethyl)-2-methyl-6,7,8,9-tetrahydro-4H-pyrido[1,2-a]pyrimidin-4-one;

64) 9-hydroxy-2-methyl-3-(2-(4-(8-methyl-5,6-dihydro-11H-benzo[5,6]cyclohepta[1,2-b]pyridin-11-ylidene)piperidin-1-yl)ethyl)-6,7,8,9-tetrahydro-4H-pyrido[1,2-a]pyrimidin-4-one;

65) 3-(2-(4-(5,6-dihydro-11H-benzo[5,6]cyclohepta[1,2-b]pyridin-11-ylidene)piperidin-1-yl)ethyl)-9-hydroxy-2-methyl-6,7,8,9-tetrahydro-4H-pyrido[1,2-a]pyrimidin-4-one;

66) (S)-2-amino-3-(4-(4-(4-(8-methoxy-5,6-dihydro-11H-benzo[5,6]cyclohepta[1,2-b]pyridin-11-ylidene)piperidin-1-yl)butoxy)phenyl)propionic acid trihydrochloride;

67) (S)-2-amino-3-(4-(4-(4-(8-methyl-5,6-dihydro-11H-benzo[5,6]cyclohepta[1,2-b]pyridin-11-ylidene)piperidin-1-yl)butoxy)phenyl)propionic acid trihydrochloride;

68) (S)-2-amino-3-(4-(4-(4-(5,6-dihydro-11H-benzo[5,6]cyclohepta[1,2-b]pyridin-11-ylidene)piperidin-1-yl)butoxy)phenyl)propionic acid trihydrochloride;

69) (4R,7S)-2-((trans-2-((4-(8-methoxy-5,6-dihydro-11H-benzo[5,6]cyclohepta[1,2-b]pyridin-11-ylidene)piperidin-1-yl)methyl)cyclohexyl)methyl)hexahydro-1H-4,7-methanoisoindole-1,3(2H)-dione;

70) (4R,7S)-2-((trans-2-((4-(5,6-dihydro-11H-benzo[5,6]cyclohepta[1,2-b]pyridin-11-ylidene)piperidin-1-yl)methyl)cyclohexyl)methyl)hexahydro-1H-4,7-methanoisoindole-1,3(2H)-dione;

71) (4R,7S)-2-((trans-2-((4-(8-methyl-5,6-dihydro-11H-benzo[5,6]cyclohepta[1,2-b]pyridin-11-ylidene)piperidin-1-yl)methyl)cyclohexyl)methyl)hexahydro-1H-4,7-methanoisoindole-1,3(2H)-dione;

72) 2-((trans-2-((4-(8-methoxy-5,6-dihydro-11H-benzo[5,6]cyclohepta[1,2-b]pyridin-11-ylidene)piperidin-1-yl)methyl)cyclohexyl)methyl)hexahydro-1H-isoindole-1,3(2H)-dione;

73) 2-((trans-2-((4-(5,6-dihydro-11H-benzo[5,6]cyclohepta[1,2-b]pyridin-11-ylidene)piperidin-1-yl)methyl)cyclohexyl)methyl)hexahydro-1H-isoindole-1,3(2H)-dione; and 74) 2-((trans-2-((4-(8-methyl-5,6-dihydro-11H-benzo[5,6]cyclohepta[1,2-b]pyridin-11-ylidene)piperidin-1-yl)methyl)cyclohexyl)methyl)hexahydro-1H-isoindole-1,3(2H)-dione.

In another aspect, the present invention provides a use of the compound, which is the tricyclic derivative represented by Chemical Formula 1 or a pharmaceutically acceptable salt, stereoisomer, or prodrug thereof, as a serotonin receptor antagonist (in particular, a serotonin 2A receptor antagonist).

Moreover, the present invention provides a use of the compound, which is the tricyclic derivative represented by Chemical Formula 1 or a pharmaceutically acceptable salt, stereoisomer, or prodrug thereof, for the prevention or treatment of diseases associated with serotonin activation.

Here, the "prevention" refers to any action that inhibits or delays the occurrence, spread, and recurrence of metabolic diseases or abnormally proliferative diseases through administration of the pharmaceutical composition, and the "treatment" refers to any action that ameliorates or advantageously changes the symptoms of the aforementioned diseases through administration of the pharmaceutical composition.

Further, the present invention provides a use of the compound, which is the tricyclic derivative represented by Chemical Formula 1 or a pharmaceutically acceptable salt, stereoisomer, or prodrug thereof, for the production of a drug for preventing or treating diseases associated with serotonin activation. Furthermore, the present invention provides a use of the compound, which is the tricyclic derivative represented by Chemical Formula 1 or a pharmaceutically acceptable salt, stereoisomer, or prodrug thereof, for the production of a drug for inhibiting the activity of serotonin.

In addition, the present invention provides a method for preventing or treating diseases associated with serotonin activation, the method including administering the compound, which is the tricyclic derivative represented by Chemical Formula 1 or a pharmaceutically acceptable salt, stereoisomer, or prodrug thereof, to a subject in need thereof. Moreover, the present invention provides a method for inhibiting the activity of serotonin, the method including administering the compound, which is the tricyclic derivative represented by Chemical Formula 1 or a pharmaceutically acceptable salt, stereoisomer, or prodrug thereof, to a subject in need thereof. Here, the "subject in need thereof" refers to any animal including a human, a monkey, a cow, a horse, a sheep, a pig, a chicken, a turkey, a quail, a cat, a dog, a mouse, a rat, and a rabbit in which diseases associated with serotonin activation are developed or may be developed.

Moreover, the "administration" refers to providing a predetermined substance to a subject in need thereof by any suitable method, and regarding the administration route of the compound according to the present invention, administration can be performed through any general route as long as the compound can reach a target tissue.

In still another aspect, the present invention provides a pharmaceutical composition for inhibiting the activity of serotonin, the pharmaceutical composition containing, as an active ingredient, the compound which is the tricyclic derivative represented by Chemical Formula 1 or a pharmaceutically acceptable salt, stereoisomer, or prodrug thereof.

In still another aspect, the present invention provides a pharmaceutical composition for preventing or treating diseases associated with serotonin activation, the pharmaceutical composition containing, as an active ingredient, the compound which is the tricyclic derivative represented by Chemical Formula 1 or a pharmaceutically acceptable salt, stereoisomer, or prodrug thereof.

The serotonin receptor to be inhibited by the compound or pharmaceutical composition according to the present invention may be, in particular, serotonin 2A ($5\text{-}HT_{2A}$) receptor.

Moreover, the diseases, which are associated with serotonin activation and are to be prevented or treated in the present invention, may be a metabolic disease or cancer.

The metabolic diseases may be any one selected from the group consisting of obesity, diabetes, hyperlipidemia, arteriosclerosis, fatty liver, steatohepatitis, fibrosis, and hypertension. Here, the fatty liver and steatohepatitis include non-alcoholic fatty liver diseases (NAFLD) and non-alcoholic steatohepatitis (NASH), in addition to alcoholic fatty liver diseases.

Furthermore, the cancer may be any one selected from the group consisting of colon cancer, breast cancer, and ovarian cancer.

The pharmaceutical composition according to the present invention may contain the compound, which is the tricyclic derivative represented by Chemical Formula 1 or a pharmaceutically acceptable salt, stereoisomer, or prodrug thereof, as an active ingredient in an amount of 0.1 to 90 wt %, specifically 0.1 to 75 wt %, and more specifically 1 to 50 wt % with respect to the total weight of the composition.

The composition according to the present invention may further contain, as an active ingredient, a typical and non-toxic pharmaceutically acceptable additive blended in a formulation according to a conventional method, in addition to the compound according to the present invention. For example, the pharmaceutical composition may further contain a pharmaceutically acceptable carrier, diluent, or excipient.

Examples of the additive used in the composition according to the present invention include a sweetening agent, a binder, a solvent, a solubilizing agent, a wetting agent, an emulsifying agent, an isotonic agent, an absorbent, a disintegrating agent, an antioxidant, a preservative, a lubricant, a filler, and a flavoring agent. For example, the additive may include lactose, dextrose, sucrose, mannitol, sorbitol, cellulose, glycine, silica, talc, stearic acid, stearin, magnesium stearate, magnesium aluminosilicate, starch, gelatin, gum tragacanth, alginic acid, sodium alginate, methylcellulose, sodium carboxymethylcellulose, agar, water, ethanol, polyethylene glycol, polyvinyl pyrrolidone, sodium chloride, calcium chloride, orange essence, strawberry essence, vanilla flavor, and the like.

The composition according to the present invention may be blended in various formulation forms for oral administration (for example, a tablet, a pill, a powdered drug, a capsule, a syrup, or an emulsion) or parenteral administration (for example, an intramuscular, intravenous, or subcutaneous injection).

Preferably, the composition according to the present invention may be blended as a formulation for oral administration, and the additive used at this time may include cellulose, calcium silicate, corn starch, lactose, sucrose, dextrose, calcium phosphate, stearic acid, magnesium stearate, calcium stearate, gelatin, talc, a surfactant, a suspending agent, an emulsifying agent, a diluent, and the like.

Specifically, a solid formulation for oral administration includes a tablet, a pill, a powdered drug, a granule, a capsule, and the like, and such a solid formulation may be formulated by mixing the aforementioned composition with at least one excipient, for example, starch, calcium carbonate, sucrose, lactose, gelatin, and the like. Moreover, lubricants such as magnesium stearate and talc can be used, in addition to simple excipients.

Furthermore, examples of a liquid formulation for oral administration include a suspending agent, an oral liquid, an emulsion, and a syrup, and various excipients, for example, a wetting agent, a sweetening agent, an air freshener, a preservative, and the like may be included, in addition to water and liquid paraffin which are commonly used simple diluents.

In addition, a formulation for parenteral administration includes a sterilized aqueous solution agent, a non-aqueous solvent, a suspending agent, an emulsion, a freeze-dried formulation, and a suppository. Propylene glycol, polyethylene glycol, a vegetable oil such as olive oil, and an injectable ester such as ethyl oleate can be used as the non-aqueous solvent and the suspending agent. Witepsol, Macrogol, Tween 61, cacao butter, laurinum, glycerogelatin, and the like can be used as the base of the suppository. Meanwhile, an injection may include additives in the related art such as a solubilizer, an isotonic agent, a suspending agent, an emulsifying agent, a stabilizer, and an antiseptic agent.

The compound or composition according to the present invention may be administered to a patient in a therapeutically effective amount or in a pharmaceutically effective amount.

Here, the "therapeutically effective amount" or the "pharmaceutically effective amount" is an amount of a compound or composition effective for preventing or treating a target disease, and refers to an amount which is sufficient to treat a disease with a reasonable benefit/risk ratio applicable to medical treatment and does not cause side effects. The level of the effective amount can be determined according to factors including the health condition of a patient, the type and severity of a disease, the activity of a drug, sensitivity to a drug, an administration method, an administration time, an administration route, an excretion rate, a treatment period, and a blended or concurrently used drug, and other factors well known in the medical field.

The compound or composition according to the present invention may be administered as an individual therapeutic agent or may be administered in combination with other therapeutic agents, may be administered sequentially or simultaneously with a therapeutic agent in the related art, and may be administered singly or in multiples. It is important to administer an amount capable of achieving the maximum effect in the minimum amount without causing side effects, in consideration of all of the aforementioned factors, and the amount can be easily determined by a person with ordinary skill in the art.

Specifically, the effective amount of the compound in the composition according to the present invention may vary depending on the age, sex, and body weight of a patient, and in general, 0.1 to 1,000 mg and preferably 5 to 200 mg per kg of body weight may be administered daily or every other day, or may be dividedly administered once to three times a day. However, the amount may be increased or decreased depending on an administration route, the severity of a disease, a sex, a body weight, an age, and the like, and thus the scope of the present invention is not limited thereto.

Preferably, the compound or composition according to the present invention may be administered for tumor therapy in combination with chemotherapy, radiation therapy, immunotherapy, hormone treatment, bone marrow transplantation, stem cell replacement therapy, other biological treatment, surgical intervention, or a combination thereof. For example, the compound or composition according to the present invention can be used as adjuvant therapy together with other long-term progressive treatment strategies or can be used to maintain the condition of a critically ill patient subjected to tumor regression or chemopreventive therapy.

Preferably, the pharmaceutical composition according to the present invention may additionally contain one or more active ingredients, and the additional active ingredient may be an anti-proliferative compound such as an aromatase inhibitor, an anti-estrogen, a topoisomerase I inhibitor, a topoisomerase II inhibitor, a microtubule active compound, an alkylating compound, a histone deacetylase inhibitor, a compound that induces cell differentiation processes, a cyclooxygenase inhibitor, an MMP inhibitor, an mTOR inhibitor, an anti-neoplastic anti-metabolite, a platin compound, a compound that targets/reduces protein or lipid kinase activity, an anti-angiogenic compound, a compound that targets, reduces, or inhibits protein or lipid phosphatase activity, a gonadorelin agonist, an anti-androgen, a methionine aminopeptidase inhibitor, a bisphosphonate, a biological response modifier, an anti-proliferative antibody, a heparanase inhibitor, an Ras oncogenic isotype inhibitor, a telomerase inhibitor, a proteasome inhibitor, a compound used in the treatment of hematologic malignancies, a compound that targets, reduces, or inhibits Flt-3 activity, a Hsp90 inhibitor, a kinesin spindle protein inhibitor, an MEK inhibitor, a leucovorin, an EDG binding agent, an anti-leukemia compound, a ribonucleotide reductase inhibitor, an S-adenosylmethionine decarboxylase inhibitor, a hemostatic steroid, a corticosteroid, other chemotherapeutic compounds, or a photosensitizing compound, but is not limited to these examples.

MODE FOR THE INVENTION

Hereinafter, the present invention will be described in more detail with reference to the following Examples. However, the following Examples are provided only for a better understanding of the present invention, and the contents of the present invention are not limited by these Examples.

Example 2: Preparation of 8-chloro-11-(piperidin-4-ylidene)-6,11-dihydro-5H-benzo[5,6]cyclohepta[1,2-b]pyridine dihydrochloride

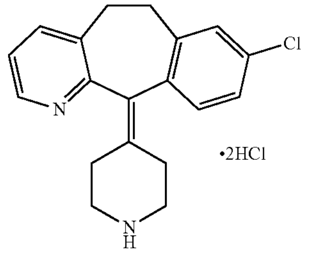 [SMILES: Clc1ccc2c(c1)CCc1cccnc1C2=C1CCNCC1]

•2HCl

Loratadine (10 g, 26.117 mmol) was added to 100 mL of a concentrated hydrochloric acid solution, and the resultant was refluxed while stirring for 12 hours. Thereafter, an excessive amount of the hydrochloric acid solution was evaporated to obtain a title compound (9.5 g, yield of 95%). $^1$H NMR (300 MHz, DMSO-$d_6$): δ 9.43 (bs, 3H), 8.67 (d, J=5.49 Hz, 1H), 8.39 (d, J=7.63 Hz, 1H), 7.93-7.81 (m, 1H), 7.47-7.39 (m, 1H), 7.34 (d, J=8.24 Hz, 1H), 7.20 (d, J=7.93 Hz, 1H), 3.20-2.30 (m, 12H).

Example 9: Preparation of 3-(2-(4-(8-chloro-5,6-dihydro-11H-benzo[5,6]cyclohepta[1,2-b]pyridin-11-ylidene)piperidin-1-yl)ethyl)-2-methyl-6,7,8,9-tetrahydro-4H-pyrido[1,2-a]pyrimidin-4-one

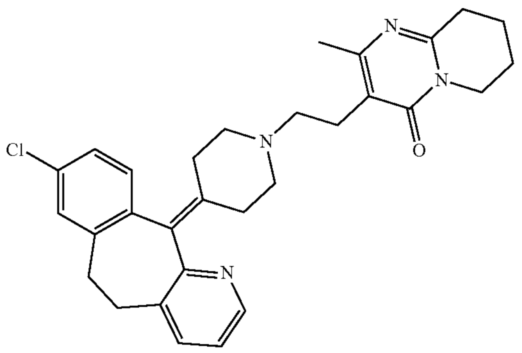 [SMILES: Cc1nc2n(c(=O)c1CCN1CCC(=C3c4ccc(Cl)cc4CCc4cccnc43)CC1)CCCC2]

Step 1: Preparation of 8-chloro-11-(piperidin-4-ylidene)-6,11-dihydro-5H-benzo[5,6]cyclohepta[1,2-b]pyridine Loratadine (2 g, 5.2 mmol) was dissolved in 10 mL of a concentrated hydrochloric acid solution, and then refluxed for 12 hours. After the hydrochloric acid solution was evaporated, water was added to the mixed solution. The pH was adjusted to 8 using ammonium hydroxide, and the mixed solution was extracted with dichloromethane and then washed with water and brine. The collected organic layer was dried over anhydrous sodium sulfate and then concentrated to obtain a title compound as a white solid (1.5 g, yield of 92%). $^1$H NMR (400 MHz, DMSO-$d_6$): δ 8.32 (d, J=4.58 Hz, 1H), 7.56 (d, J=7.63 Hz, 1H), 7.28 (s, 1H), 7.23-7.15 (m, 2H), 7.06 (dd, J=8.24, 1.53 Hz, 1H), 3.46-3.21 (m, 3H), 2.93-2.75 (m, 4H), 2.65-2.53 (m, 1H), 2.34-2.04 (m, 4H); LCMS [M+H] 311.1

Step 2: Preparation of 3-(2-(4-(8-chloro-5,6-dihydro-11H-benzo[5,6]cyclohepta[1,2-b]pyridin-11-ylidene)piperidin-1-yl)ethyl)-2-methyl-6,7,8,9-tetrahydro-4H-pyrido[1,2-a]pyrimidin-4-one After the compound (120 mg, 0.313 mmol) obtained in the step 1 of Example 9 was dissolved in 2 mL of N,N-dimethylformamide, sodium carbonate (99.43 mg, 0.938 mmol), potassium iodide (51.91 mg, 0.313 mmol), 3-(2-chloroethyl)-2-methyl-6,7,8,9-tetrahydro-4H-pyrido[1,2-a]pyrimidin-4-one (77.74 mg, 0.344 mmol) were sequentially added, and the resultant was then heated to 80° C. After the completion of the reaction, extraction was performed twice with brine and ethyl acetate. The collected organic layer was dried over anhydrous sodium sulfate and then concentrated. The residue was purified by silica gel column chromatography to obtain a title compound (140 mg, yield of 89%). $^1$H NMR (300 MHz, MeOD): δ 8.49 (dd, J=4.88, 1.22 Hz, 1H), 7.87 (d, J=7.63 Hz, 1H), 7.50-7.44 (m, 1H), 7.38 (d, J=2.14 Hz, 1H), 7.35-7.23 (m, 2H), 4.92-4.78 (m, 2H), 3.65-3.28 (m, 9H), 2.96-2.43 (m, 16H)

Example 10: Preparation of 3-(2-(4-(8-chloro-5,6-dihydro-11H-benzo[5,6]cyclohepta[1,2-b]pyridin-11-ylidene)piperidin-1-yl)ethyl)-9-hydroxy-2-methyl-6,7,8,9-tetrahydro-4H-pyrido[1,2-a]pyrimidin-4-one

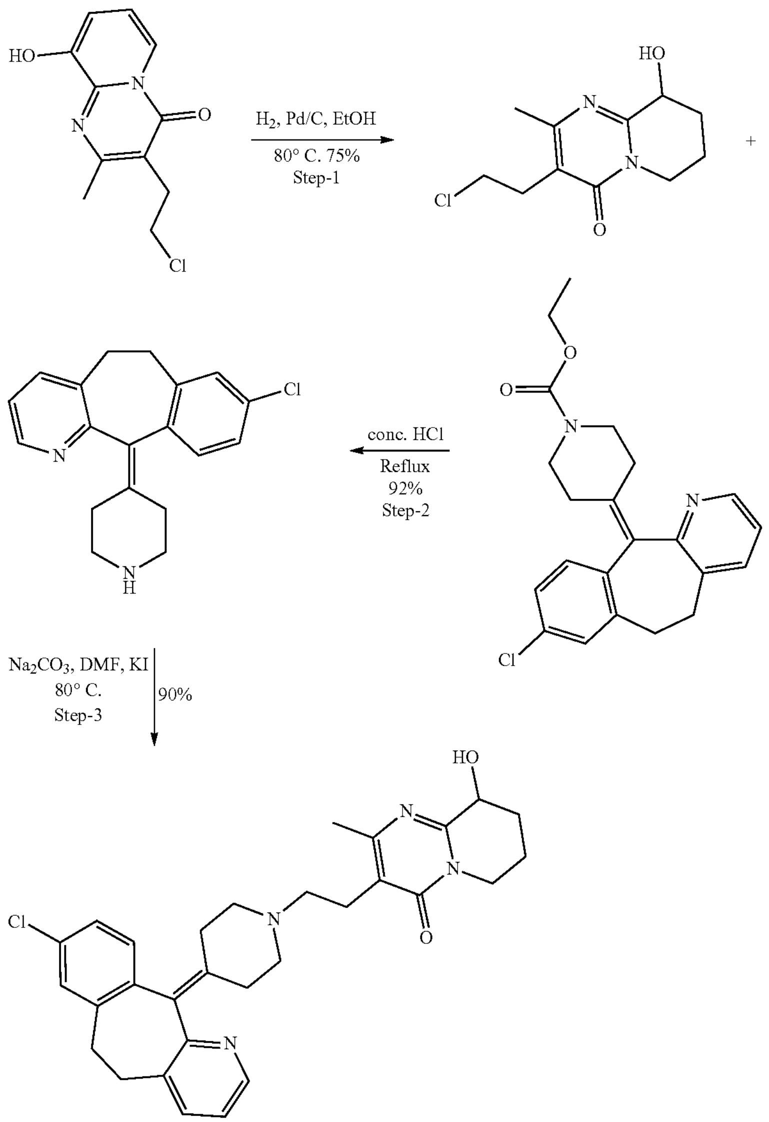

Step 1: Preparation of 3-(2-chloroethyl)-9-hydroxy-2-methyl-6,7,8,9-tetrahydro-4H-pyrido[1,2-a]pyrimidin-4-one In a 10-L reaction vessel connected to a gas purger and a thermo pocket, 3-(2-chloroethyl)-9-hydroxy-2-methyl-4H-pyrido[1,2-a]pyrimidin-4-one hydrochloride (400 g, 1.45 mol) was dissolved in methanol (4,800 mL), and the resultant was then stirred. After filling the reaction vessel with nitrogen gas, 10% Pd/C/RD-854 (80 g) was added. The obtained solution was heated to 55° C., and then stirred for 2 hours while slowly injecting hydrogen gas. After the completion of the reaction, the mixed solution was cooled to room temperature, and Pd/C was then removed by filtration with celite under nitrogen gas. The residue was washed with methanol (2×400 mL) and then concentrated. Water (1,480 mL) was added to the obtained compound, and the resultant was then heated to 80° C. to 85° C. for 15 minutes. The mixed solution was cooled to room temperature, and potassium acetate (285.4 g, 2.9077 mol) dissolved in 300 mL of water was then slowly added for 1 hour. The solution was stirred at room temperature for 1 hour, cooled to 8° C. to 12° C. for 2 hours, and then stirred. The generated crystals were filtered, then washed with ethylenediaminetetraacetic acid disodium salt dihydrate (2 g) dissolved in 400 mL of water, and washed with water (400 mL) and isopropyl alcohol (200 mL) to obtain a solid. The solid was dried under vacuum to obtain a title compound as a white solid (266 g, yield of 75%). $^1H$ NMR (400 MHz, DMSO-$d_6$): δ 5.71 (s, 1H), 4.48-4.41 (m, 1H), 3.96-3.84 (m, 1H), 3.78-3.62 (m, 3H), 2.95-2.85 (m, 2H), 2.28 (s, 3H), 2.06-1.74 (m, 4H); LCMS [M+H] 243.1

Step 2: Preparation of 8-chloro-11-(piperidin-4-ylidene)-6,11-dihydro-5H-benzo[5,6]cyclohepta[1,2-b]pyridine Loratadine (2 g, 5.2 mmol) was dissolved in 10 mL of a concentrated hydrochloric acid solution, and the resultant was then refluxed for 12 hours. After the hydrochloric acid solution was evaporated, water was added to the mixed solution. The pH was adjusted to 8 using ammonium hydroxide, and the mixed solution was extracted with dichloromethane and then washed with water and brine. The collected organic layer was dried over anhydrous sodium sulfate and then concentrated to obtain a title compound as a white solid (1.5 g, yield of 92%). $^1$H NMR (400 MHz, DMSO-$d_6$): δ 8.32 (d, J=4.58 Hz, 1H), 7.56 (d, J=7.63 Hz, 1H), 7.28 (s, 1H), 7.23-7.15 (m, 2H), 7.06 (dd, J=8.24, 1.53 Hz, 1H), 3.46-3.21 (m, 3H), 2.93-2.75 (m, 4H), 2.65-2.53 (m, 1H), 2.34-2.04 (m, 4H); LCMS [M+H] 311.1

Step 3: Preparation of 3-(2-(4-(8-chloro-5,6-dihydro-11H-benzo[5,6]cyclohepta[1,2-b]pyridin-11-ylidene)piperidin-1-yl)ethyl)-9-hydroxy-2-methyl-6,7,8,9-tetrahydro-4H-pyrido[1,2-a]pyrimidin-4-one After the compound (500 mg, 1.609 mmol) obtained in the step 2 of Example 10 was dissolved in 4 mL of N,N-dimethylformamide, sodium carbonate (511.49 mg, 4.826 mmol), potassium iodide (267.04 mg, 1.0609 mmol), and the compound (390.41 mg, 1.609 mmol) obtained in the step 1 of Example 10 were sequentially added, and the mixed solution was heated to 80° C. After the completion of the reaction, extraction was performed twice with ethyl acetate and brine. The collected organic layer was dried over anhydrous sodium sulfate and concentrated. The residue was purified by silica gel column chromatography to obtain a title compound (745 mg, yield of 90%). $^1$H NMR (400 MHz, DMSO-$d_6$): δ 8.30 (d, J=4.58 Hz, 1H), 7.53 (d, J=7.63 Hz, 1H), 7.26 (s, 1H), 7.21-7.12 (m, 2H), 7.04 (d, J=7.93 Hz, 1H), 5.63 (d, J=4.27 Hz, 1H), 4.43-4.34 (m, 1H), 3.89-3.78 (m, 1H), 3.67-3.55 (m, 1H), 3.29 (s, 3H), 3.35-3.20 (m, 2H), 2.86-2.42 (m, 6H), 2.40-2.04 (m, 10H), 1.98-1.68 (m, 2H); LCMS [M+H] 517.2

Example 22: Preparation of (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propionic acid trihydrochloride

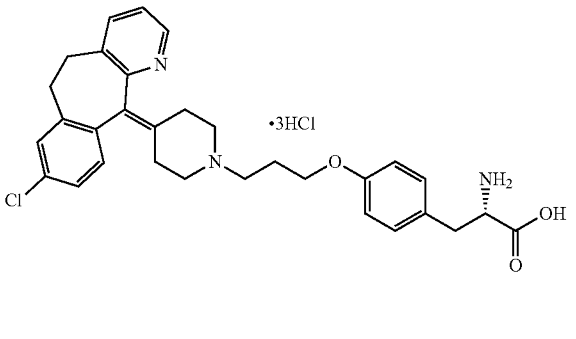 [SMILES: N[C@@H](Cc1ccc(OCCCN2CCC(=C3c4ccc(Cl)cc4CCc4cccnc43)CC2)cc1)C(=O)O]

Step 1: Preparation of ethyl (t-butoxycarbonyl)-L-tyrosine

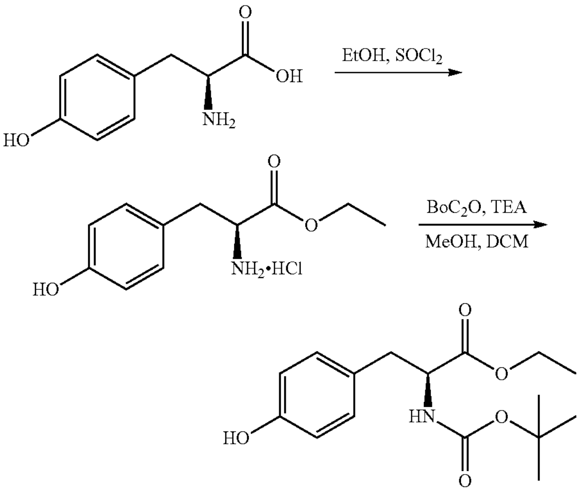

After L-tyrosine (100 g, 0.552 mol) was dissolved in 800 mL of ethanol, the resultant was stirred while slowly adding thionyl chloride (100.1 mL, 1.38 mol). The mixed solution was stirred at 0° C. for 1 hour and then refluxed overnight. After the completion of the reaction, the mixed solution was concentrated to remove a volatile substance, thereby obtaining ethyl L-tyrosinate hydrochloride. The ethyl L-tyrosinate hydrochloride was added to 100 mL of methanol and 800 mL of dichloromethane, and the resultant was stirred at room temperature. Thereafter, triethylamine (154 mL, 1.1 mol) and di-t-butyl dicarbonate (120.5 g, 0.552 mol) dissolved in 200 mL of dichloromethane were sequentially added to the reaction solution at 0° C. The mixed solution was stirred at room temperature overnight, and the solid was then removed by filtration. Water was added to the mixed solution to perform extraction, and the organic layer was treated with sodium sulfate and then concentrated to obtain a title compound (136 g, yield of 80%) as a white solid.

Step 2: Preparation of ethyl (S)-3-(4-(3-bromopropoxy)phenyl)-2-((t-butoxycarbonyl)amino)propanoate

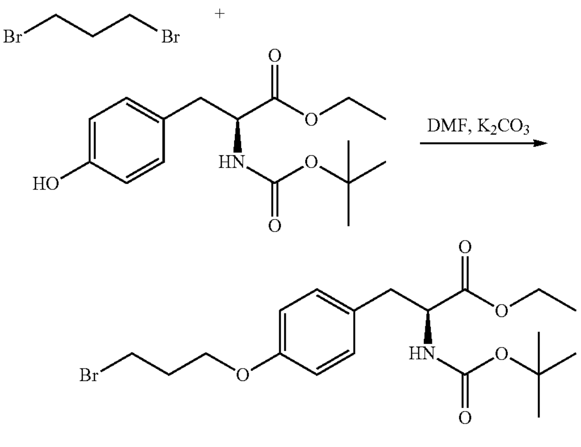

Ethyl (t-butoxycarbonyl)-L-tyrosinate (2 g, 6.645 mmol), calcium carbonate (902.39 mg, 6.53 mmol), 1,3-dibromopropane (3.92 g, 19.39 mmol) were dissolved in 20 mL of N,N-dimethylformamide, and the resultant was then stirred at 100° C. for 7 hours. After the mixed solution was cooled to room temperature, 200 mL of water was added to perform extraction with ethyl acetate, and washing with brine was performed. The organic layer was treated with sodium sulfate, and the filtrate was concentrated and then purified by silica gel column chromatography to obtain a title compound (1.1 g, yield of 40%).

Step 3: Preparation of ethyl (S)-2-((t-butoxycarbonyl)amino)-3-(4-(3-(4-(8-chloro-5,6-dihydro-11H-benzo[5,6]cyclohepta[1,2-b]pyridin-11-ylidene)piperidin-1-yl)propoxy)phenyl)propanoate

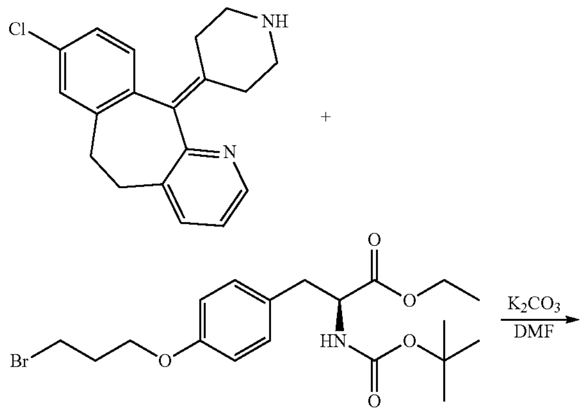

-continued

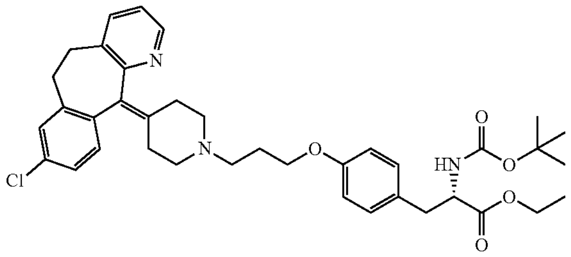

8-Chloro-11-(piperidin-4-ylidene)-6,11-dihydro-5H-benzo[5,6]cyclohepta[1,2-b]pyridine (200 mg, 0.521 mmol) was dissolved in 4 mL of N,N-dimethylformamide, and the resultant was stirred. Sodium carbonate (209.91 mg, 1.98 mmol) and ethyl (S)-3-(4-(3-bromopropoxy)phenyl)-2-((t-butoxycarbonyl)amino)propanoate (246.69 mg, 0.573 mmol) were sequentially added to the reaction solution. Thereafter, the mixed solution was heated to 80° C. and then stirred for 3 hours. After the completion of the reaction, brine and ethyl acetate were added to the mixed solution to perform extraction. The organic layer was treated with sodium sulfate, and the filtrate was concentrated and then purified by silica gel column chromatography to obtain a title compound (310 mg, yield of 90%).

Step 4: Preparation of (S)-2-((t-butoxycarbonyl)amino)-3-(4-(3-(4-(8-chloro-5,6-dihydro-11H-benzo[5,6]cyclohepta[1,2-b]pyridin-11-ylidene)piperidin-1-yl)propoxy)phenyl)propionic acid

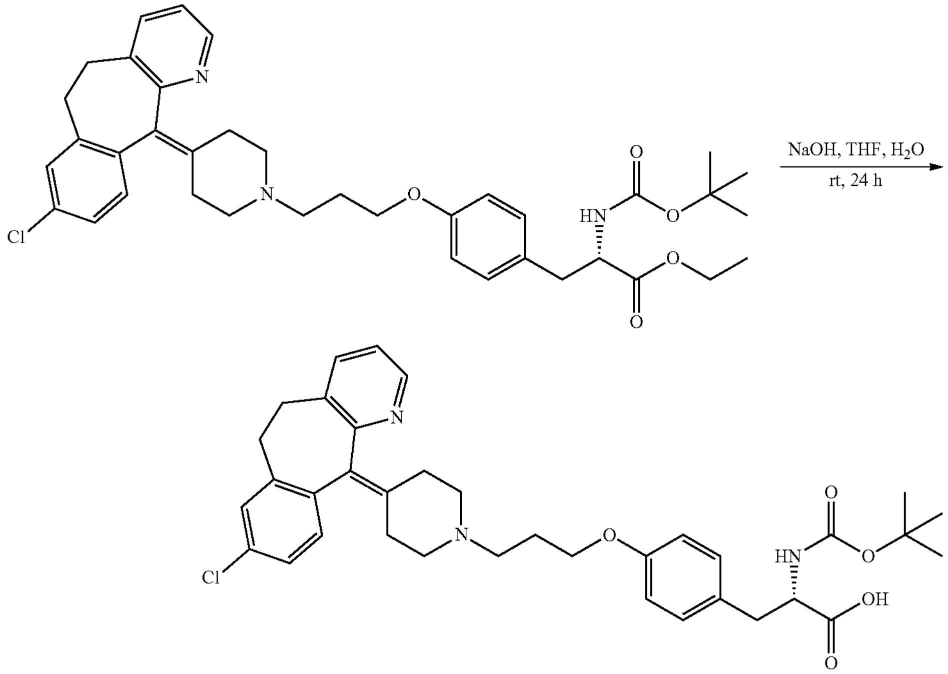

The compound (310 mg, 0.469 mmol) obtained in the step 3 of Example 22 was dissolved in 80 mL of a tetrahydrofuran/water (3:1) solution, and sodium hydroxide (93.9 mg, 2.34 mmol) was then added. Thereafter, the mixed solution was stirred at room temperature for 24 hours. After the completion of the reaction, tetrahydrofuran was evaporated, and the pH was adjusted to 4 using a 1 N hydrochloric acid solution. After adding 50 mL of water, extraction with ethyl acetate was performed (3×100 mL). The organic layer was washed with brine and then treated with sodium sulfate to concentrate the filtrate. The concentrated mixture was purified by silica gel column chromatography to obtain a title compound (260 mg, yield of 87%).

Step 5: Preparation of (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl) propionic acid trihydrochloride

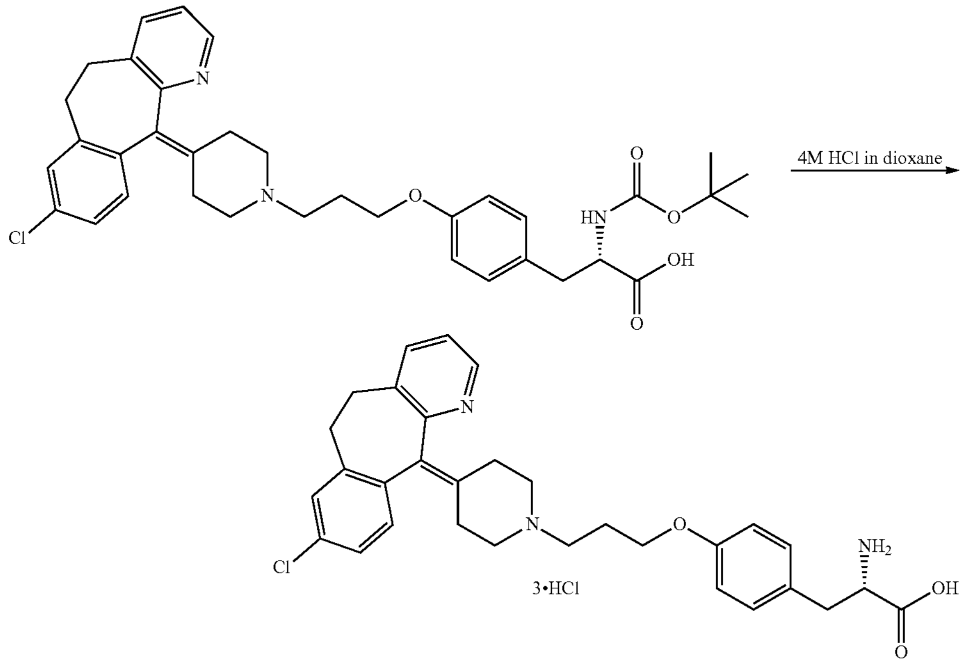

After ((S)-2-((t-butoxycarbonyl)amino)-3-(4-(3-(4-(8-chloro-5,6-dihydro-11H-benzo[5,6]cyclohepta[1,2-b]pyridin-11-ylidene)piperidin-1-yl)propoxy)phenyl)propionic acid was dissolved in 10 mL of ethyl acetate, 10 mL of a solution of 4.0 M hydrochloric acid in 1,4-dioxin was added. Thereafter, the mixed solution was stirred for 12 hours. The mixed solution was concentrated and then filtered to obtain a title compound (180 mg, yield of 77%) as a white solid. $^1H$ NMR (300 MHz, DMSO-$d_6$): δ 11.40 (s, 1H), 8.63-8.55 (m, 1H), 8.45 (bs, 3H), 8.24-8.11 (m, 1H), 7.79-7.63 (m, 1H), 7.42 (dd, J=9.00, 2.14 Hz, 1H), 7.32 (d, J=8.24 Hz, 1H), 7.29-7.11 (m, 3H), 6.90 (dd, J=18.92, 8.54 Hz, 2H), 4.12-3.98 (m, 3H), 3.53-3.41 (m, 2H), 3.36-2.76 (m, 8H), 2.67-2.35 (m, 6H), 2.31-2.11 (m, 2H).

Example 25: Preparation of (4R,7S)-2-(((1S,2S)-2-((4-(8-chloro-5,6-dihydro-11H-benzo[5,6]cyclohepta[1,2-b]pyridin-11-ylidene)piperidin-1-yl)methyl) cyclohexyl)methyl)hexahydro-1H-4,7-methanoisoindole-1,3(2H)-dione

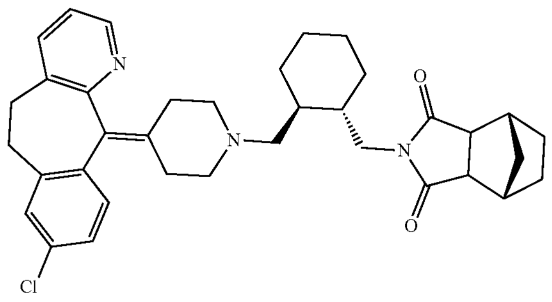 [SMILES: O=C1C2C(C(=O)N1C[C@H]1CCCC[C@@H]1CN1CCC(=C3c4ccc(Cl)cc4CCc4cccnc43)CC1)[C@H]1CC[C@@H]2C1]

Step 1: Preparation of ((1R,2R)-cyclohexane-1,2-diyl)bis(methylene) dimethanesulfonate

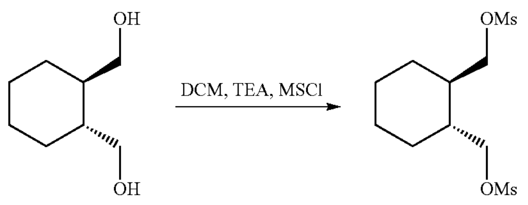 [SMILES: OC[C@@H]1CCCC[C@H]1CO ; CS(=O)(=O)OC[C@@H]1CCCC[C@H]1COS(C)(=O)=O]

Methanesulfonyl chloride (1.2 mL, 15.257 mmol) and triethylamine (2.5 mL, 17.337 mmol) were sequentially added at 0° C. to 5° C. to ((1R,2R)-cyclohexane-1,2-diyl) dimethanol (1 g, 6.935 mmol) dissolved in 50 mL of dichloromethane. After the temperature was slowly raised to room temperature, the reaction solution was stirred for 2 hours. 50 mL of dichloromethane was added to the obtained mixture, and extraction with water was performed. The collected organic layer was dried over anhydrous sodium sulfate and concentrated. The residue was purified by silica gel column chromatography to obtain a title compound (1.8 g, yield of 86%).

Step 2: Preparation of ((1R,2R)-2-(((4R,7S)-1,3-dioxooctahydro-2H-4,7-methanolisoindol-2-yl) methyl)cyclohexyl)methyl methanesulfonate

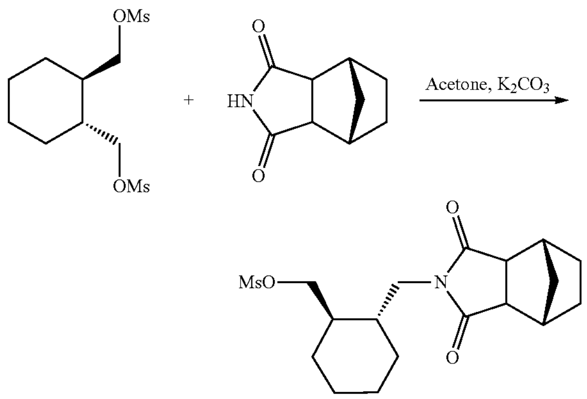

The compound (545 mg, 1.816 mmol) obtained in the step 1 of Example 25 and (4R,7S)-hexahydro-1H-4,7-methanoisoindole-1,3(2H)-dione (300 mg, 1.816 mmol) were dissolved in 20 mL of acetone, potassium carbonate (376.45 mg, 2.724 mmol) was then added, and the resultant was refluxed for 12 hours. After the obtained mixture was concentrated, the residue was purified by silica gel column chromatography to obtain a title compound (520 mg, yield of 78%).

Step 3: Preparation of (4R,7S)-2-(((1S,2S)-2-((4-(8-chloro-5,6-dihydro-11H-benzo[5,6]cyclohepta[1,2-b] pyridin-11-ylidene)piperidin-1-yl)methyl)cyclohexyl)methyl)hexahydro-1H-4,7-methanoisoindole-1,3(2H)-dione

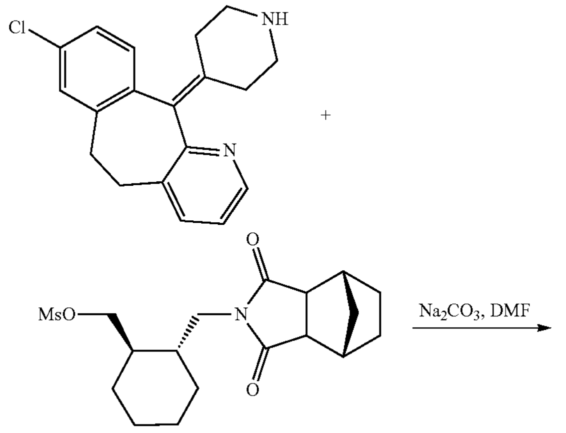

-continued

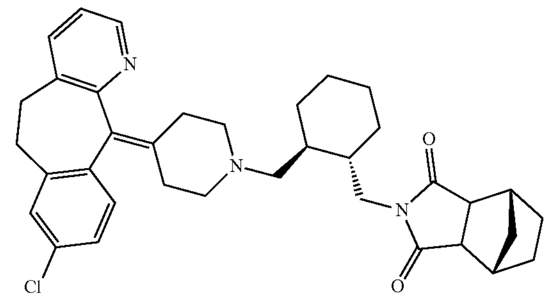

After the compound (200 mg, 0.521 mmol) obtained in the step 2 of Example 10 was dissolved in 2 mL of N,N-dimethylformamide, sodium carbonate (165.72 mg, 1.564 mmol) and the compound (211.84 mg, 0.573 mmol) obtained in the step 2 of Example 25 were sequentially added, and the resultant was stirred at 80° C. for 3 hours. After the completion of the reaction, extraction was performed twice with brine and ethyl acetate. The collected organic layer was dried over anhydrous sodium sulfate and then concentrated. The residue was purified by silica gel column chromatography to obtain a title compound (250 mg, yield of 82%). $^1H$ NMR (300 MHz, $CDCl_3$): δ 8.47-8.32 (m, 1H), 7.42 (d, J=7.93 Hz, 1H), 7.24-7.02 (m, 4H), 4.01-3.11 (m, 4H), 2.93-0.93 (m, 32H)

Example 26: Preparation of 2-(((1S,2S)-2-((4-(8-chloro-5,6-dihydro-11H-benzo[5,6]cyclohepta[1,2-b] pyridin-11-ylidene)piperidin-1-yl)methyl)cyclohexyl)methyl)hexahydro-1H-isoindole-1,3(2H)-dione

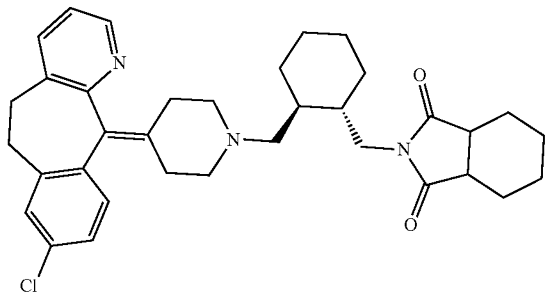 [SMILES: O=C1C2CCCCC2C(=O)N1C[C@H]1CCCC[C@@H]1CN1CCC(=C2c3ccc(Cl)cc3CCc3cccnc32)CC1]

Step 1: Preparation of ((1R,2R)-2-((1,3-dioxooctahydro-2H-isoindol-2-yl)methyl)cyclohexyl)methyl methanesulfonate

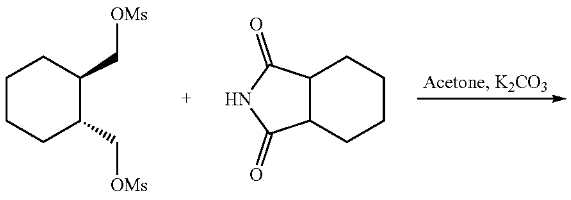

-continued

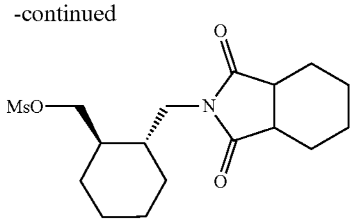

The compound (588.25 mg, 1.958 mmol) obtained in the step 1 of Example 25 and hexahydro-1H-isoindole-1,3(2H)-dione (300 mg, 1.958 mmol) were dissolved in 20 mL of acetone, potassium carbonate (405.94 mg, 2.937 mmol) was then added, and the resultant was refluxed for 12 hours. The obtained mixture was concentrated, and the residue was purified by silica gel column chromatography to obtain a title compound (550 mg, yield of 79%).

Step 2: Preparation of 2-(((1S,2S)-2-((4-(8-chloro-5,6-dihydro-11H-benzo[5,6]cyclohepta[1,2-b]pyridin-11-ylidene)piperidin-1-yl)methyl)cyclohexyl)methyl)hexahydro-1H-isoindole-1,3(2H)-dione

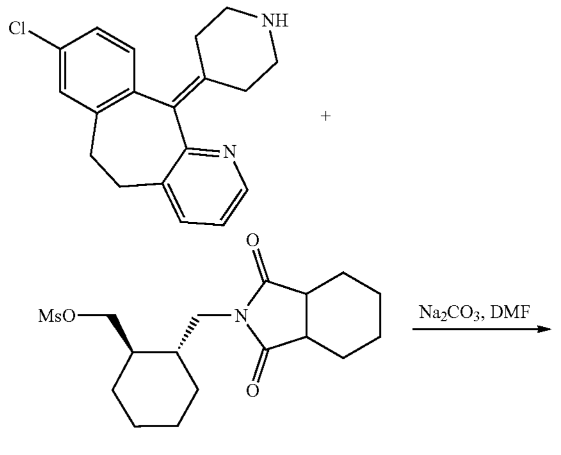

-continued

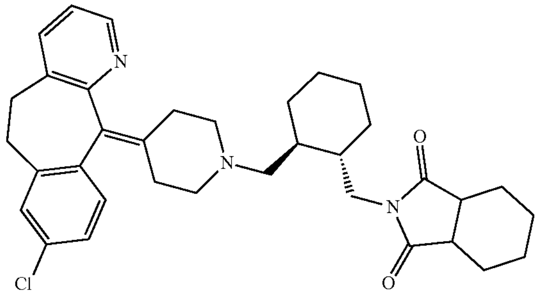

After the compound (200 mg, 0.521 mmol) obtained in the step 2 of Example 10 was dissolved in 2 mL of N,N-dimethylformamide, sodium carbonate (165.72 mg, 1.564 mmol) and the compound (204.96 mg, 0.573 mmol) obtained in the step 1 of Example 26 were sequentially added, and the resultant was heated to 80° C. for 3 hours. After the completion of the reaction, extraction was performed twice with brine and ethyl acetate. The collected organic layer was dried over anhydrous sodium sulfate and concentrated. The residue was purified by silica gel column chromatography to obtain a title compound (260 mg, yield of 87%). $^1$H NMR (300 MHz, $CDCl_3$): δ 8.44-8.34 (m, 1H), 7.41 (d, J=7.93 Hz, 1H), 7.23-7.03 (m, 4H), 3.48-3.12 (m, 2H), 2.92-0.94 (m, 34H).

Example 31: Preparation of ethyl (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propanoate trihydrochloride

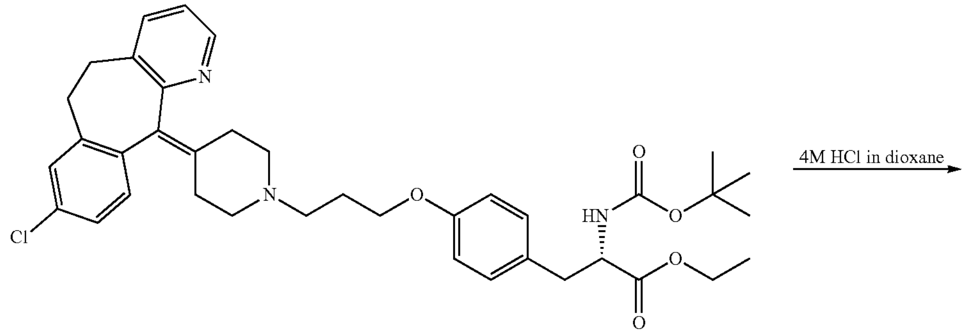

-continued

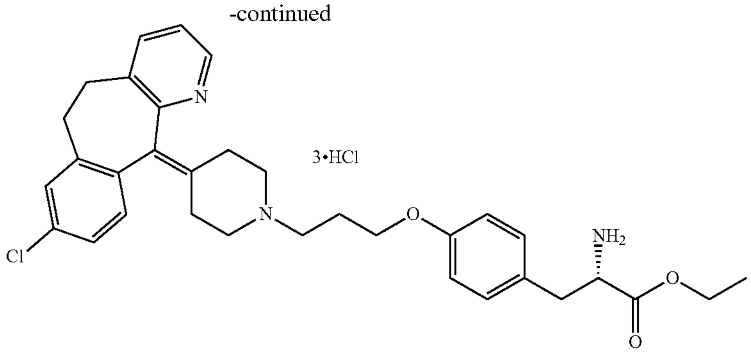

After the compound (900 mg, 1.36 mmol) obtained in the step 3 of Example 22 was dissolved in 20 mL of ethyl acetate, 15 mL of a solution of 4.0 M hydrochloric acid in 1,4-dioxin was added, and the resultant was stirred for 12 hours. Thereafter, the mixed solution was concentrated and then filtered to obtain a title compound (810 mg, yield of 88%) as a white solid. $^{1}H$ NMR (300 MHz, DMSO-$d_6$): δ 8.66-8.47 (m, 4H), 8.24-8.08 (m, 1H), 7.78-7.60 (m, 1H), 7.39 (d, J=11.29 Hz, 1H), 7.29 (d, J=8.24 Hz, 1H), 7.17-7.07 (m, 3H), 6.93-6.79 (m, 2H), 4.21-3.94 (m, 5H), 3.49-3.37 (m, 2H), 3.30-2.08 (m, 18H), 1.13 (t, J=7.02 Hz, 3H).

Example 48: Preparation of 8-chloro-11-(piperidin-4-ylidene)-6,11-dihydro-5H-benzo[5,6]cyclohepta[1,2-b]pyridine

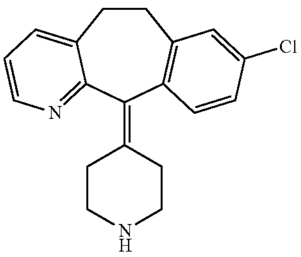 [SMILES: Clc1ccc2c(c1)CCc1cccnc1C2=C1CCNCC1]

After the compound (5 g) obtained in Example 2 was dissolved in water, an ammonia aqueous solution was added to adjust the pH to 8. Thereafter, the mixed solution was extracted with ethyl acetate (3×100 mL). The organic layer was washed with brine and treated with sodium sulfate, and the filtrate was then concentrated to obtain a title compound. LC-MS (m/z): 311.1270 (M+H)

Example 51: Preparation of cyclopentyl (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propanoate trihydrochloride

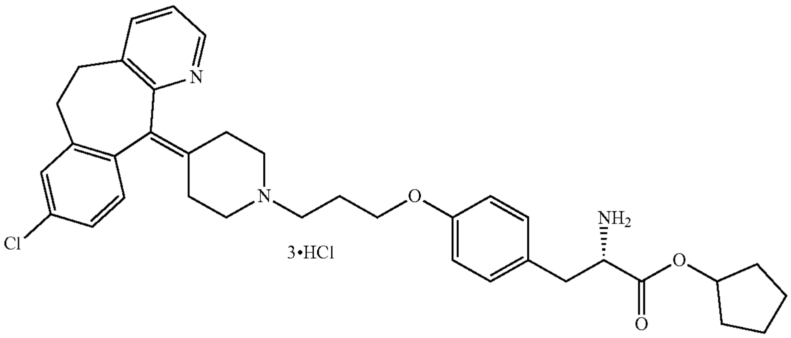 [SMILES: N[C@@H](Cc1ccc(OCCCN2CCC(=C3c4ccc(Cl)cc4CCc4cccnc43)CC2)cc1)C(=O)OC1CCCC1]

Step 1: Preparation of cyclopentyl (S)-3-(4-(3-bromopropoxy)phenyl)-2-((tert-butoxycarbonyl)amino)propanoate

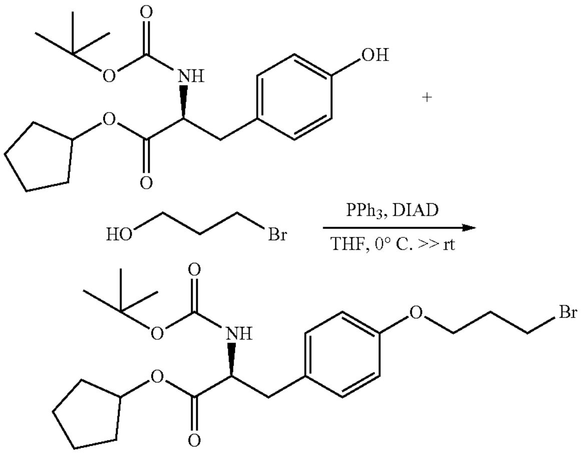

Triphenylphosphine (563 g, 2.146 mmol) and 3-bromopropan-1-ol (298 mg, 2.146 mmol) were added to cyclopentyl (tert-butoxycarbonyl)-L-tyrosinate (500 mg, 1.431 mmol) dissolved in 100 mL of tetrahydrofuran. The mixed solution was cooled to 0° C., and diisopropyl azodicarboxylate (DIAD, 0.4 mL, 2.146 mmol) was then slowly added. The temperature of the mixed solution was slowly raised to room temperature and the mixed solution was stirred for 24 hours. The obtained mixture was evaporated, and extraction with water and ethyl acetate was then performed. The collected organic layer was dried over anhydrous sodium sulfate and concentrated. The residue was purified by silica gel column chromatography to obtain a title compound (560 mg, yield of 83%).

Step 2: Preparation of cyclopentyl (S)-2-((tert-butoxycarbonyl)amino)-3-(4-(3-(4-(8-chloro-5,6-dihydro-11H-benzo[5,6]cyclohepta[1,2-b]pyridin-11-ylidene)piperidin-1-yl)propoxy)phenyl)propanoate

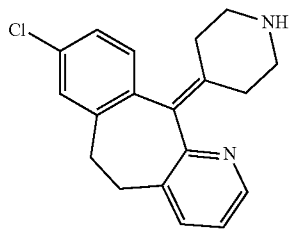

+

-continued

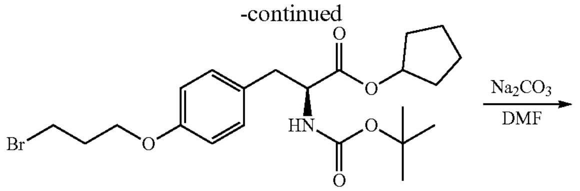

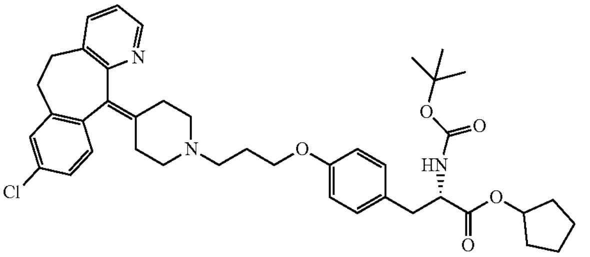

After the compound (170 mg, 0.443 mmol) obtained in the step 2 of Example 10 was dissolved in 2 mL of N,N-dimethylformamide, sodium carbonate (141 mg, 1.329 mmol) and the compound (219 mg, 0.465 mmol) obtained in the step 1 of Example 51 were sequentially added, and the resultant was heated to 80° C. for 3 hours. After the completion of the reaction, extraction was performed twice with brine and ethyl acetate. The collected organic layer was dried over anhydrous sodium sulfate and concentrated. The residue was purified by silica gel column chromatography to obtain a title compound (270 mg, yield of 87%).

Step 3: Preparation of cyclopentyl (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propanoate trihydrochloride

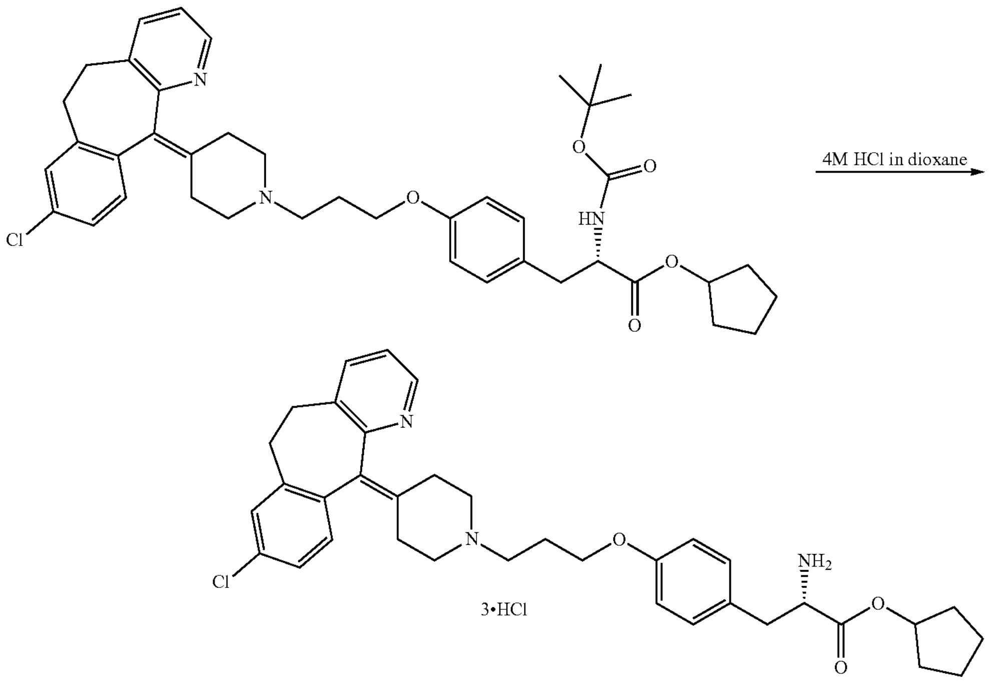

After the compound (270 mg, 0.386 mmol) obtained in the step 2 of Example 51 was dissolved in ethyl acetate (20 mL), a solution of 4 M hydrochloric acid in 1,4-dioxin was added, and the resultant was stirred. The mixed solution was evaporated and then filtered to obtain a title compound (220 mg, yield of 80%). $^1$H NMR (300 MHz, DMSO-$d_6$): δ 8.66-8.52 (m, 4H), 8.22 (s, 1H), 7.76 (s, 1H), 7.43 (dd, J=11.14, 2.14 Hz, 1H), 7.33 (dd, J=8.24, 2.14 Hz, 1H), 7.29-7.09 (m, 3H), 6.90 (dd, J=18.62, 8.54 Hz, 2H), 5.11-5.0 (m, 1H), 4.18-3.95 (m, 3H), 3.54-3.37 (m, 2H), 3.33-2.71 (m, 8H), 2.68-2.32 (m, 6H), 2.31-2.08 (m, 2H), 1.83-1.65 (m, 2H), 1.63-1.31 (m, 6H)

Example 63: Preparation of 9-hydroxy-3-(2-(4-(8-methoxy-5,6-dihydro-11H-benzo[5,6]cyclohepta[1,2-b]pyridin-11-ylidene)piperidin-1-yl)ethyl)-2-methyl-6,7,8,9-tetrahydro-4H-pyrido[1,2-a]pyrimidin-4-one

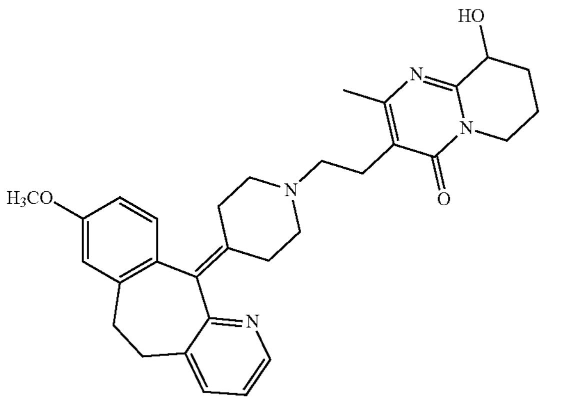 [SMILES: COc1ccc2c(c1)CCc1cccnc1C2=C1CCN(CCc2c(C)nc3n(c2=O)CCCC3O)CC1]

Step 1: Preparation of 8-methoxy-11-(piperidin-4-ylidene)-6,11-dihydro-5H-benzo[5,6]cyclohepta[1,2-b]pyridine Ethyl 4-(8-methoxy-5,6-dihydro-11H-benzo[5,6]cyclohepta[1,2-b]pyridin-11-ylidene)piperidine-1-carboxylate (150 mg, 0.396 mmol) was dissolved in 1 mL of a concentrated hydrochloric acid solution, and the resultant was then refluxed for 12 hours. After the hydrochloric acid solution was evaporated, water was added. The pH was adjusted to 8 using ammonium hydroxide, and extraction with dichloromethane was then performed. The collected organic layer was washed with water and brine, dried over anhydrous sodium sulfate, and then concentrated to obtain a title compound (110 g, yield of 90%).

Step 2: Preparation of 9-hydroxy-3-(2-(4-(8-methoxy-5,6-dihydro-11H-benzo[5,6]cyclohepta[1,2-b]pyridin-11-ylidene)piperidin-1-yl)ethyl)-2-methyl-6,7,8,9-tetrahydro-4H-pyrido[1,2-a]pyrimidin-4-one After the compound (100 mg, 0.326 mmol) obtained in the step 1 of Example 63 was dissolved in 2 mL of N,N-dimethylformamide, sodium carbonate (103.77 mg, 0.979 mmol), potassium iodide (54.18 mg, 0.326 mmol), and the compound (79.21 mg, 0.326 mmol) obtained in the step 1 of Example 10 were sequentially added, and the resultant was heated to 80° C. After the completion of the reaction, extraction was performed twice with brine and ethyl acetate. The collected organic layer was dried over anhydrous sodium sulfate and concentrated. The residue was purified by silica gel column chromatography to obtain a title compound (140 mg, yield of 84%). LCMS [M+H] 513.2

Example compounds as shown in Table 1 below were synthesized through the aforementioned synthetic routes and routes similar to the synthetic routes.

TABLE 1

| No | Structure | Chemical name | NMR/MS |
|---|---|---|---|
| 1 | 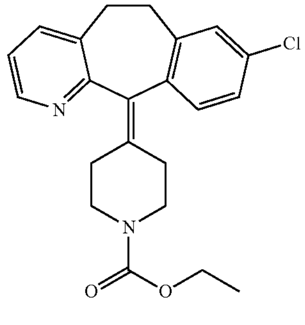 [SMILES: CCOC(=O)N1CCC(=C2c3ccc(Cl)cc3CCc3cccnc32)CC1] | ethyl 4-(8-chloro-5,6-dihydro-11H-benzo-[5,6]cyclohepta[1,2-b]-pyridin-11-ylidene)-piperidine-1-carbox-ylate | LC-MS (m/z): 383.1482 (M + H) |
| 2 | 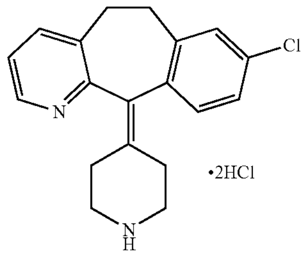 [SMILES: Clc1ccc2c(c1)CCc1cccnc1C2=C1CCNCC1] •2HCl | 8-chloro-11-(piperi-din-4-ylidene)-6,11-dihydro-5H-benzo-[5,6]cyclohepta[1,2-b]pyridine dihydro-chloride | $^1$H NMR (300 MHz, DMSO-$d_6$): δ 9.43(bs, 3H), 8.67 (d, J = 5.49 Hz, 1H), 8.39 (d, J = 7.63 Hz, 1H), 7.93-7.81 (m, 1H), 7.47-7.39 (m, 1H), 7.34 (d, J = 8.24 Hz, 1H), 7.20 (d, J = 7.93 Hz, 1H), 3.20-2.30 (m, 12H). |

TABLE 1-continued

| No | Structure | Chemical name | NMR/MS |
|---|---|---|---|
| 3 | 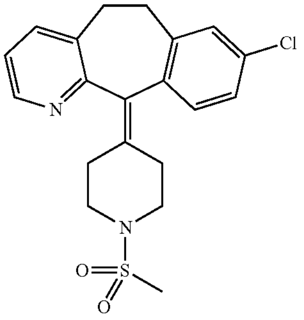 [SMILES: CS(=O)(=O)N1CCC(=C2c3ccc(Cl)cc3CCc3cccnc32)CC1] | 8-chloro-11-(1-(methylsulfonyl)piperidin-4-ylidene)-6,11-dihydro-5H-benzo-[5,6]cyclohepta[1,2-b]pyridine | LC-MS (m/z): 389.1046 (M + H) |
| 4 | 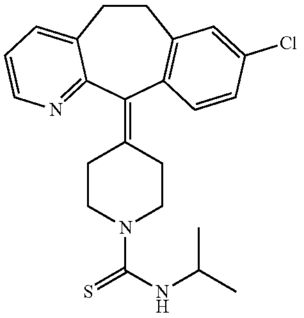 [SMILES: CC(C)NC(=S)N1CCC(=C2c3ccc(Cl)cc3CCc3cccnc32)CC1] | 4-(8-chloro-5,6-dihydro-11H-benzo-[5,6]cyclohepta[1,2-b]pyridin-11-ylidine)-N-isopropylpiperidine-1-carbothioamide | LC-MS (m/z): 412.1570 (M + H) |
| 5 | 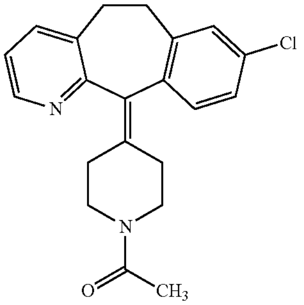 [SMILES: CC(=O)N1CCC(=C2c3ccc(Cl)cc3CCc3cccnc32)CC1] | 1-(4-(8-chloro-5,6-dihydro-11H-benzo-[5,6]cyclohepta[1,2-b]pyridin-11-ylidene)-piperidin-1-yl)ethan-1-one | LC-MS (m/z): 353.1376 (M + H) |
| 6 | 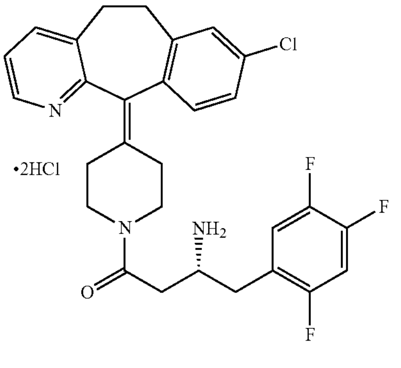 [SMILES: N[C@@H](CC(=O)N1CCC(=C2c3ccc(Cl)cc3CCc3cccnc32)CC1)Cc1cc(F)c(F)cc1F] •2HCl | (R)-3-amino-1-(4-(8-chloro-5,6-dihydro-11H-benzo[5,6]cyclohepta[1,2-b]pyridin-11-ylidene)piperidin-1-yl)-4-(2,4,5-trifluorophenyl)butan-1-one dihydrochloride | LC-MS (m/z): 527.1765 (M + H) |
| 7 | 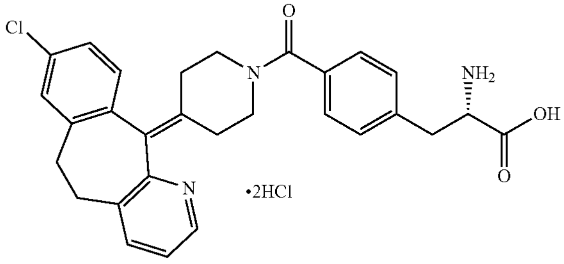 [SMILES: N[C@@H](Cc1ccc(C(=O)N2CCC(=C3c4ccc(Cl)cc4CCc4cccnc43)CC2)cc1)C(=O)O] •2HCl | (S)-2-amino-3-(4-(4-(8-chloro-5,6-dihydro-11H-benzo[5,6]cyclohepta[1,2-b]pyridin-11-ylidene)piperidine-1-carbonyl)phenyl)-propionic acid dihydrochloride | LC-MS (m/z): 503.1790 (M + H) |

TABLE 1-continued

| No | Structure | Chemical name | NMR/MS |
|---|---|---|---|
| 8 | 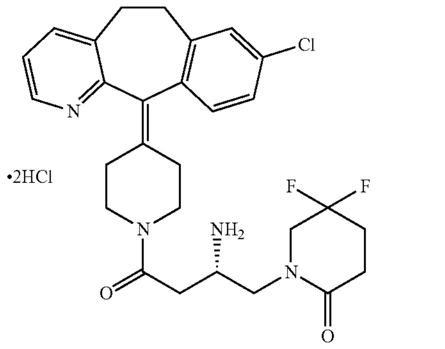 [SMILES: N[C@@H](CC(=O)N1CCC(=C2c3ccc(Cl)cc3CCc3cccnc32)CC1)CN1CC(F)(F)CCC1=O] | (S)-1-(2-amino-4-(4-(8-chloro-5,6-dihydro-11H-benzo[5,6]cyclo-hepta[1,2-b]pyridin-11-ylidene)piperidin-1-yl)-4-oxobutyl)-5,5-difluoropiperidin-2-one dihydrochloride | LC-MS (m/z): 530.2074 (M + H) |
| 9 | 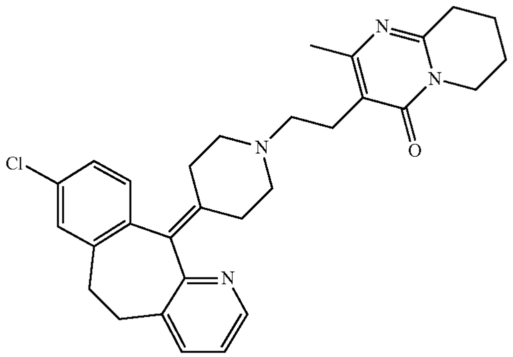 [SMILES: Cc1nc2n(c(=O)c1CCN1CCC(=C3c4ccc(Cl)cc4CCc4cccnc43)CC1)CCCC2] | 3-(2-(4-(8-chloro-5,6-dihydro-11H-benzo-[5,6]cyclohepta[1,2-b]pyridin-11-ylidene)-piperidin-1-yl)ethyl)-2-methyl-6,7,8,9-tetra-hydro-4H-pyrido[1,2-a]pyrimidin-4-one | $^1$H NMR (300 MHz, MeOD): δ 8.49 (dd, J = 4.88, 1.22 Hz, 1H), 7.87 (d, J = 7.63 Hz, 1H), 7.50-7.44 (m, 1H), 7.38 (d, J = 2.14 Hz, 1H), 7.35-7.23 (m, 2H), 4.92-4.78 (m, 2H), 3.65-3.28 (m, 9H), 2.96-2.43 (m, 16H). |
| 10 | 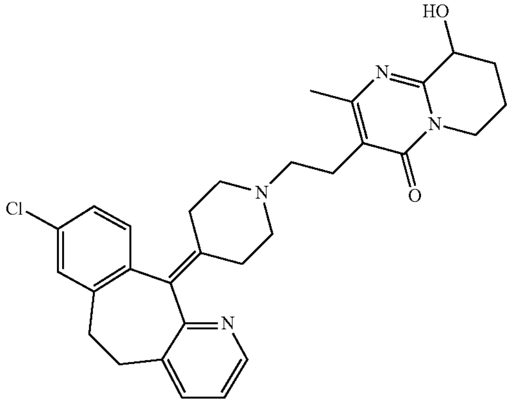 [SMILES: Cc1nc2n(c(=O)c1CCN1CCC(=C3c4ccc(Cl)cc4CCc4cccnc43)CC1)CCCC2O] | 3-(2-(4-(8-chloro-5,6-dihydro-11H-benzo-[5,6]cyclohepta[1,2-b]pyridin-11-ylidene)-piperidin-1-yl)ethyl)-9-hydroxy-2-methyl-6,7,8,9-tetrahydro-4H-pyrido[1,2-a]-pyrimidin-4-one | $^1$H NMR (300 MHz, DMSO-$d_6$): δ 8.30 (d, J = 4.58 Hz, 1H), 7.53 (d, J = 7.63 Hz, 1H), 7.26 (s, 1H), 7.21-7.12 (m, 2H), 7.04 (d, J = 7.93 Hz, 1H), 5.63 (d, J = 4.27 Hz, 1H), 4.43-4.34 (m, 1H), 3.89-3.78 (m, 1H), 3.67-3.55 (m, 1H), 3.29 (s, 3H), 3.35-3.20 (m, 2H), 2.86-2.42 (m, 6H), 2.40-2.04 (m, 10H), 1.98-1.68 (m, 2H). |
| 11 | 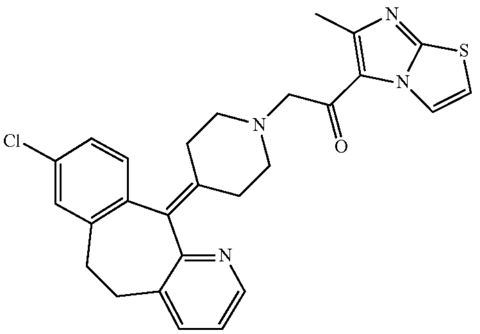 [SMILES: Cc1nc2sccn2c1C(=O)CN1CCC(=C2c3ccc(Cl)cc3CCc3cccnc32)CC1] | 2-(4-(8-chloro-5,6-dihydro-11H-benzo-[5,6]cyclohepta[1,2-b]pyridin-11-ylidene)-piperidin-1-yl)-1-(6-methylimidazo[2,1-b]thiazol-5-yl)ethan-1-one | LC-MS (m/z): 490.1408 (M + H) |

TABLE 1-continued

| No | Structure | Chemical name | NMR/MS |
|---|---|---|---|
| 12 | 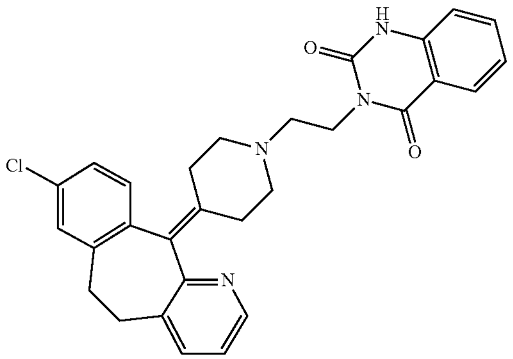 [SMILES: O=c1[nH]c2ccccc2c(=O)n1CCN1CCC(=C2c3ccc(Cl)cc3CCc3cccnc32)CC1] | 3-(2-(4-(8-chloro-5,6-dihydro-11H-benzo-[5,6]cyclohepta[1,2-b]pyridin-11-ylidene)-piperidin-1-yl)ethyl)-quinazoline-2,4-(1H,3H)-dione | $^1$H NMR (300 MHz, DMSO-$d_6$): δ 11.41 (s, 1H), 8.33 (d, J = 4.27 Hz, 1H), 7.91 (d, J = 7.93 Hz, 1H), 7.64 (t, J = 7.93 Hz, 1H), 7.56 (d, J = 7.63 Hz, 1H), 7.33-7.11 (m, 5H), 7.06 (d, J = 8.24 Hz, 1H), 4.01 (t, J = 6.10 Hz, 2H), 3.39-3.21 (m, 2H), 2.90-2.64 (m, 4H), 2.37-2.06 (m, 8H). |
| 13 | 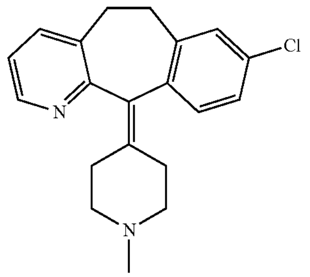 [SMILES: CN1CCC(=C2c3ccc(Cl)cc3CCc3cccnc32)CC1] | 8-chloro-11-(1-methyl-piperidin-4-ylidene)-6,11-dihydro-5H-benzo[5,6]cyclohepta-[1,2-b]pyridine | $^1$H NMR (300 MHz, $CDCl_3$): δ 8.39 (d, J = 4.58 Hz, 1H), 7.40 (d, J = 7.63 Hz, 1H), 7.25-6.98 (m, 4H), 3.52-3.28 (m, 2H), 2.91-2.63 (m, 4H), 2.63-2.31 (m, 4H), 2.26 (s, 3H), 2.16-2.02 (m, 2H). |
| 14 | 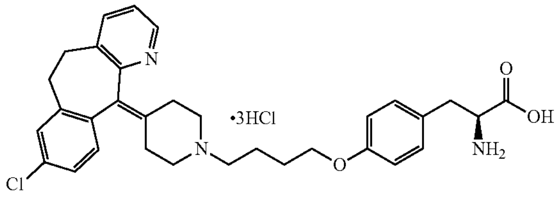 [SMILES: N[C@@H](Cc1ccc(OCCCCN2CCC(=C3c4ccc(Cl)cc4CCc4cccnc43)CC2)cc1)C(=O)O] | (S)-2-amino-3-(4-(4-(4-(8-chloro-5,6-dihydro-11H-benzo-[5,6]cyclohepta[1,2-b]pyridin-11-ylidene)-piperidin-1-yl)butoxy)-phenyl)propionic acid trihydrochloride | 1H NMR (300 MHz, DMSO-$d_6$): δ 13.7 (s, 1H), 8.53-8.45 (m, 1H), 8.28 (bs, 2H), 8.08-7.88 (m, 1H), 7.62-7.44 (m, 1H), 7.36 (d, J = 9.16 Hz, 1H), 8.24 (d, J = 7.26 Hz, 1H), 7.20-7.06 (m, 3H), 6.91-6.79 (m, 2H), 4.12-4.02 (m, 1H), 3.98-3.86 (m, 2H), 3.45-3.33 (m, 2H), 3.20-2.30 (m, 14H), 1.84-1.64 (m, 4H). |
| 15 | 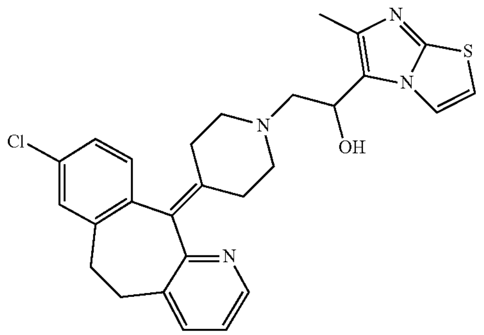 [SMILES: Cc1nc2sccn2c1C(O)CN1CCC(=C2c3ccc(Cl)cc3CCc3cccnc32)CC1] | 2-(4-(8-chloro-5,6-dihydro-11H-benzo-[5,6]cyclohepta[1,2-b]pyridin-11-ylidene)-piperidin-1-yl)-1-(6-methylimidazo[2,1-b]thiazol-5-yl)ethan-1-ol | $^1$H NMR (300 MHz, DMSO-$d_6$): δ 8.33 (d, J = 3.36 Hz, 1H), 7.81 (d, J = 3.05 Hz, 1H), 7.56 (d, J = 7.63 Hz, 1H), 7.38-6.98 (m, 5H), 5.29 (s, 1H), 5.04-4.88 (m, 1H), 2.92-2.42 (m, 6H), 2.50 (s, 3H), 2.39-2.05 (m, 8H). |
| 16 | 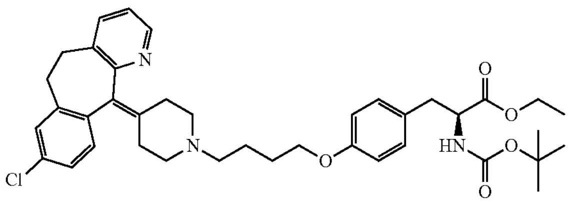 [SMILES: CCOC(=O)[C@H](Cc1ccc(OCCCCN2CCC(=C3c4ccc(Cl)cc4CCc4cccnc43)CC2)cc1)NC(=O)OC(C)(C)C] | ethyl (S)-2-((t-butoxy-carbonyl)amino)-3-(4-(4-(4-(8-chloro-5,6-dihydro-11H-benzo-[5,6]cyclohepta[1,2-b]pyridin-11-ylidene)-piperidin-1-yl)butoxy)-phenyl)propanoate | $^1$H NMR (300 MHz, $CDCl_3$): δ 8.34 (d, J = 4.12 Hz, 1H), 7.38 (dd, J = 7.56, 0.92 Hz, 1H), 7.15-6.92 (m, 6H), 6.74 (d, J = 8.47 Hz, 2H), 4.96 (d, J = 7.79 Hz, 1H), 4.53-4.39 (m, 1H), 4.11 (q, J = 7.10 Hz, 2H), 3.90 (t, J = 5.27 Hz, 2H), 3.41-3.23 (m, 2H), |

TABLE 1-continued

| No | Structure | Chemical name | NMR/MS |
|---|---|---|---|
| | | | 3.07-2.36 (m, 14H), 1.89-1.67 (m, 4H), 1.37 (s, 9H), 1.19 (t, J = 7.10 Hz, 3H). |
| 17 | 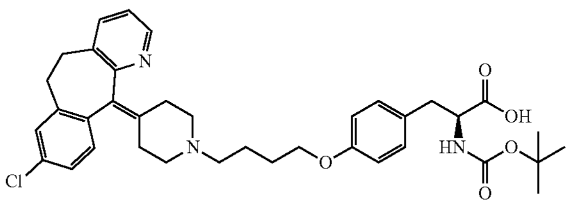 [SMILES: CC(C)(C)OC(=O)N[C@@H](Cc1ccc(OCCCCN2CCC(=C3c4ccc(Cl)cc4CCc4cccnc43)CC2)cc1)C(=O)O] | (S)-2-((t-butoxycarbonyl)amino)-3-(4-(4-(4-(8-chloro-5,6-dihydro-11H-benzo-[5,6]cyclohepta[1,2-b]pyridin-11-ylidene)piperidin-1-yl)butoxy)phenyl)-propionic acid | LC-MS (m/z): 647.2940 (M + H) |
| 18 | 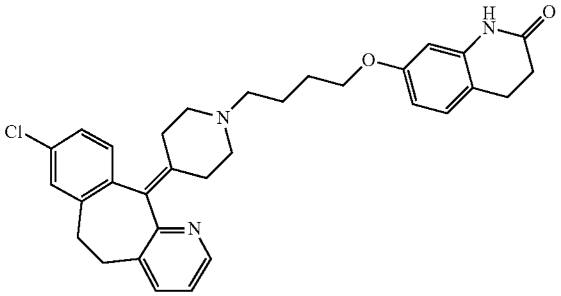 [SMILES: O=C1CCc2ccc(OCCCCN3CCC(=C4c5ccc(Cl)cc5CCc5cccnc54)CC3)cc2N1] | 7-(4-(4-(8-chloro-5,6-dihydro-11H-benzo-[5,6]cyclohepta[1,2-b]pyridin-11-ylidene)-piperidin-1-yl)-butoxy)-3,4-dihydro-quinolin-2(1H)-one | $^1$H NMR (300 MHz, DMSO-$d_6$): δ 9.93 (s, 1H), 8.29 (d, J = 4.58 Hz, 1H), 7.53 (d, J = 7.93 Hz, 1H), 7.31-6.93 (m, 5H), 6.42 (dd, J = 8.24, 2.44 Hz, 1H), 6.37 (d, J = 2.44 Hz, 1H), 3.85 (t, J = 6.41 Hz, 2H), 3.38-3.16 (m, 2H), 2.90-1.90 (m, 16H), 1.77-1.37 (m, 4H). |
| 19 | 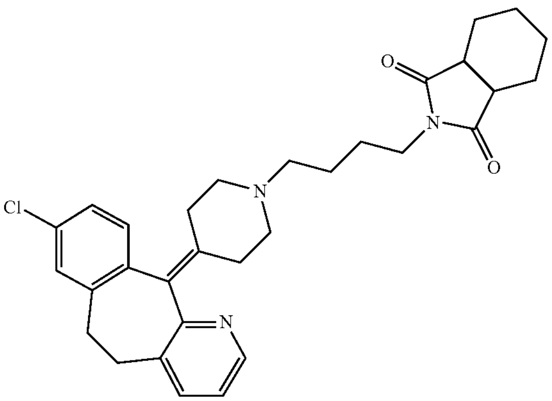 [SMILES: O=C1C2CCCCC2C(=O)N1CCCCN1CCC(=C2c3ccc(Cl)cc3CCc3cccnc32)CC1] | 2-(4-(4-(8-chloro-5,6-dihydro-11H-benzo-[5,6]cyclohepta[1,2-b]pyridin-11-ylidene)-piperidin-1-yl)butyl)-hexahydro-1H-iso-indole-1,3(2H)-dione | $^1$H NMR (300 MHz, DMSO-$d_6$): δ 8.32 (dd, J = 4.58, 1.53 Hz, 1H), 7.56 (dd, J = 7.63, 1.53 Hz, 1H), 7.28 (d, J = 2.14 Hz, 1H), 7.24-7.16 (m, 2H), 7.05 (d, J = 8.24 Hz, 1H), 3.42-3.22 (m, 4H), 2.97-2.75 (m, 4H), 2.69-2.52 (m, 1H), 2.38-1.98 (m, 7H), 1.80-1.65 (m, 2H), 1.61-1.15 (m, 12H). |
| 20 | 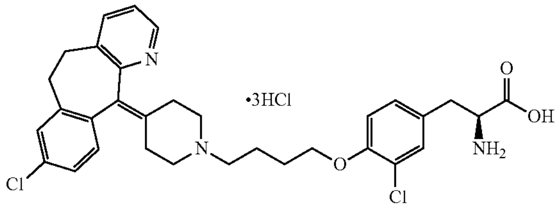 [SMILES: N[C@@H](Cc1ccc(OCCCCN2CCC(=C3c4ccc(Cl)cc4CCc4cccnc43)CC2)c(Cl)c1)C(=O)O] | (S)-2-amino-3-(3-chloro-4-(4-(4-(8-chloro-5,6-dihydro-11H-benzo[5,6]cyclo-hepta[1,2-b]pyridin-11-ylidene)piperidin-1-yl)butoxy)phenyl)-propionic acid tri-hydrochloride | $^1$H NMR (300 MHz, DMSO-$d_6$): δ 11.12 (s, 1H), 8.65-8.55 (m, 1H), 8.44 (bs, 3H), 8.26-8.11 (m, 1H), 7.81-7.65 (m, 1H), 7.47-7.05 (m, 6H), 4.20-3.98 (m, 3H), 3.54-3.40 (m, 2H), 3.27-2.73 (m, 6H), 2.63-2.35 (m, 8H), 1.98-1.74 (m, 4H). |
| 21 | 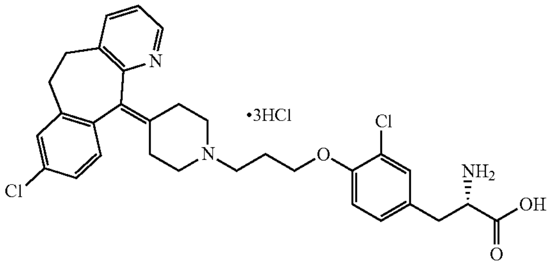 [SMILES: N[C@@H](Cc1ccc(OCCCN2CCC(=C3c4ccc(Cl)cc4CCc4cccnc43)CC2)c(Cl)c1)C(=O)O] | (S)-2-amino-3-(3-chloro-4-(3-(4-(8-chloro-5,6-dihydro-11H-benzo[5,6]cyclo-hepta[1,2-b]pyridin-11-ylidene)piperidin-1-yl)propoxy)phenyl)-propionic acid tri-hydrochloride | $^1$H NMR (300 MHz, DMSO-$d_6$): δ 11.37 (s, 1H), 8.65-8.56 (m, 1H), 8.45 (bs, 3H), 8.25-8.13 (m, 1H), 7.81-7.67 (m, 1H), 7.47-7.08 (m, 6H), 4.18 (t, J = 6.10 Hz, 1H), 4.12 (t, J = 5.80 Hz, 2H), 3.54-3.42 (m, 2H), 3.37-2.75 (m, 8H), 2.68-2.14 (m, 8H). |

TABLE 1-continued

| No | Structure | Chemical name | NMR/MS |
|---|---|---|---|
| 22 | 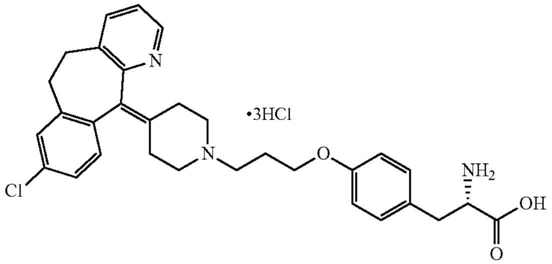 [SMILES: N[C@@H](Cc1ccc(OCCCN2CCC(=C3c4ccc(Cl)cc4CCc4cccnc43)CC2)cc1)C(=O)O] •3HCl | (S)-2-amino-3-(4-(3-(4-(8-chloro-5,6-dihydro-11H-benzo-[5,6]cyclohepta[1,2-b]pyridin-11-ylidene)-piperidin-1-yl)pro-poxy)phenyl)propionic acid trihydrochloride | $^1$H NMR (300 MHz, DMSO-$d_6$): δ 11.40 (s, 1H), 8.63-8.55 (m, 1H), 8.45 (bs, 3H), 8.24-8.11 (m, 1H), 7.79-7.63 (m, 1H), 7.42 (dd, J = 9.00, 2.14 Hz, 1H), 7.32 (d, J = 8.24 Hz, 1H), 7.29-7.11 (m, 3H), 6.90 (dd, J = 18.92, 8.54 Hz, 2H), 4.12-3.98 (m, 3H), 3.53-3.41 (m, 2H), 3.36-2.76 (m, 8H), 2.67-2.35 (m, 6H), 2.31-2.11 (m, 2H). |
| 23 | 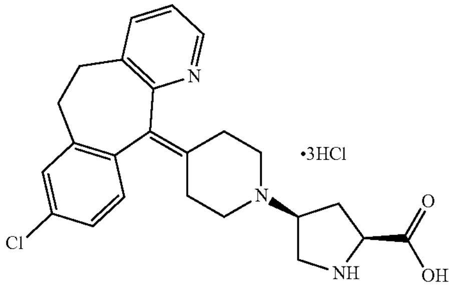 [SMILES: O=C(O)[C@@H]1C[C@H](N2CCC(=C3c4ccc(Cl)cc4CCc4cccnc43)CC2)CN1] •3HCl | (2S,4S)-4-(4-(8-chloro-5,6-dihydro-11H-benzo[5,6]cyclo-hepta[1,2-b]pyridin-11-ylidene)piperidin-1-yl)pyrrolidine-2-carboxylic acid tri-hydrochloride | $^1$H NMR (300 MHz, DMSO-$d_6$): δ 12.30 (s, 1H), 8.45 (bs, 3H), 8.25 (d, J = 3.36 Hz, 1H), 7.31 (d, J = 7.32 Hz, 1H), 7.06-6.93 (m, 4H), 3.73-3.41 (m, 1H), 3.20-2.63 (m, 7H), 2.60-1.52 (m, 10H). |
| 24 | 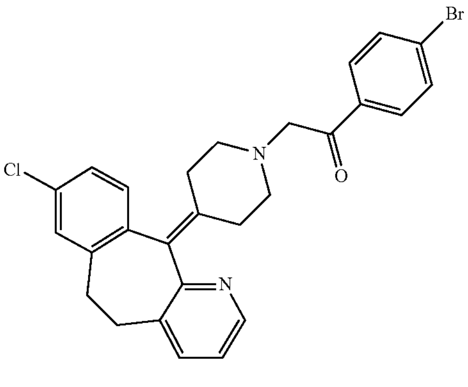 [SMILES: O=C(CN1CCC(=C2c3ccc(Cl)cc3CCc3cccnc32)CC1)c1ccc(Br)cc1] | 1-(4-bromophenyl)-2-(4-(8-chloro-5,6-dihydro-11H-benzo-[5,6]cyclohepta[1,2-b]pyridin-11-ylidene)-piperidin-1-yl)ethan-1-one | $^1$H NMR (300 MHz, DMSO-$d_6$): δ 8.33 (dd, J = 4.73, 1.53 Hz, 1H), 7.91 (d, J = 8.54 Hz, 2H), 7.72 (d, J = 8.54 Hz, 2H), 7.56 (d, J = 6.41 Hz, 1H), 7.29 (d, J = 2.14 Hz, 1H), 7.25-7.15 (m, 2H), 7.06 (d, J = 8.24 Hz, 1H), 3.82 (s, 2H), 2.88-2.76 (m, 4H), 2.42-2.10 (m, 8H). |
| 25 | 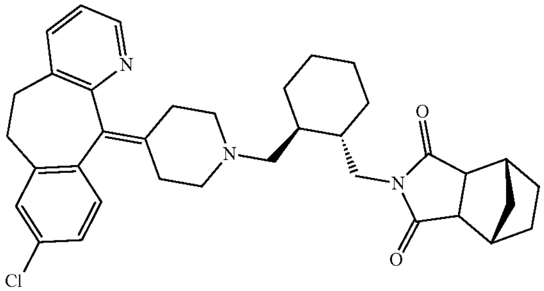 [SMILES: O=C1C2C(C(=O)N1C[C@H]1CCCC[C@@H]1CN1CCC(=C3c4ccc(Cl)cc4CCc4cccnc43)CC1)[C@H]1CC[C@@H]2C1] | (4R,7S)-2-(((1S,2S)-2-((4-(8-chloro-5,6-dihydro-11H-benzo-[5,6]cyclohepta[1,2-b]pyridin-11-ylidene)-piperidin-1-yl)meth-yl)cyclohexyl)meth-yl)hexahydro-1H-4,7-methanoisoindole-1,3(2H)-dione | $^1$H NMR (300 MHz, $CDCl_3$): δ 8.47-8.32 (m, 1H), 7.42 (d, J = 7.93 Hz, 1H), 7.24-7.02 (m, 4H), 4.01-3.11 (m, 4H), 2.93-0.93 (m, 32H). |

TABLE 1-continued

| No | Structure | Chemical name | NMR/MS |
|---|---|---|---|
| 26 | 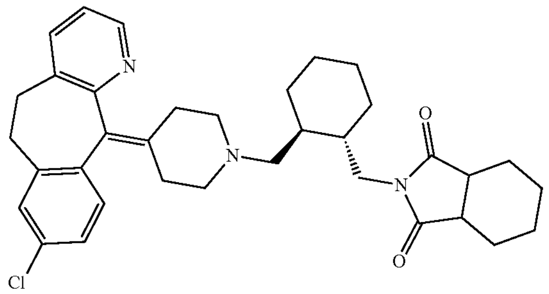 [SMILES: O=C1C2CCCCC2C(=O)N1C[C@H]1CCCC[C@@H]1CN1CCC(=C2c3ccc(Cl)cc3CCc3cccnc32)CC1] | 2-(((1S,2S)-2-((4-(8-chloro-5,6-dihydro-11H-benzo[5,6]cyclohepta[1,2-b]pyridin-11-ylidene)piperidin-1-yl)methyl)cyclohexyl)methyl)hexahydro-1H-isoindole-1,3(2H)-dione | $^1$H NMR (300 MHz, $CDCl_3$): δ 8.44-8.34 (m, 1H), 7.41 (d, J = 7.93 Hz, 1H), 7.23-7.03 (m, 4H), 3.48-3.12 (m, 2H), 2.92-0.94 (m, 34H). |
| 27 | 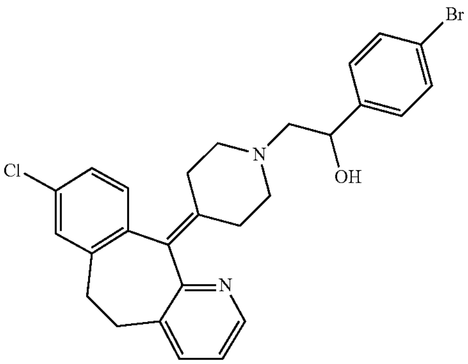 [SMILES: OC(CN1CCC(=C2c3ccc(Cl)cc3CCc3cccnc32)CC1)c1ccc(Br)cc1] | 1-(4-bromophenyl)-2-(4-(8-chloro-5,6-dihydro-11H-benzo-[5,6]cyclohepta[1,2-b]pyridin-11-ylidene)-piperidin-1-yl)ethan-1-ol | $^1$H NMR (300 MHz, $CDCl_3$): δ 8.40 (d, J = 4.27 Hz, 1H), 7.49-7.39 (m, 3H), 7.28-7.20 (m, 2H), 7.20-7.06 (m, 4H), 4.74-4.64 (m, 1H), 3.47-3.29 (m, 2H), 3.27-2.18 (m, 12H). |
| 28 | 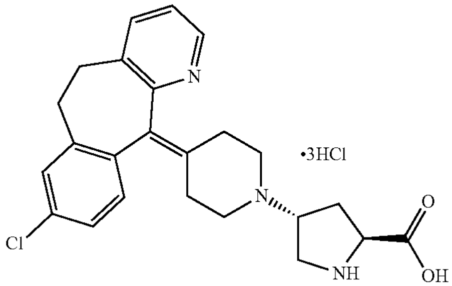 [SMILES: O=C(O)[C@@H]1C[C@@H](N2CCC(=C3c4ccc(Cl)cc4CCc4cccnc43)CC2)CN1] | (2S,4R)-4-(4-(8-chloro-5,6-dihydro-11H-benzo[5,6]cyclohepta[1,2-b]pyridin-11-ylidine)piperidin-1-yl)pyrrolidine-2-carboxylic acid | LC-MS (m/z): 424.1747 (M + H) |
| 29 | 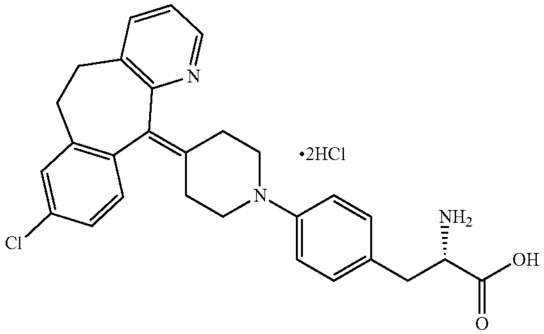 [SMILES: N[C@@H](Cc1ccc(N2CCC(=C3c4ccc(Cl)cc4CCc4cccnc43)CC2)cc1)C(=O)O] | (S)-2-amino-3-(4-(4-(8-chloro-5,6-dihydro-11H-benzo[5,6]cyclohepta[1,2-b]pyridin-11-ylidene)piperidin-1-yl)phenyl)propionic acid dihydrochloride | LC-MS (m/z): 475.1841 (M + H) |

TABLE 1-continued

| No | Structure | Chemical name | NMR/MS |
|---|---|---|---|
| 30 | 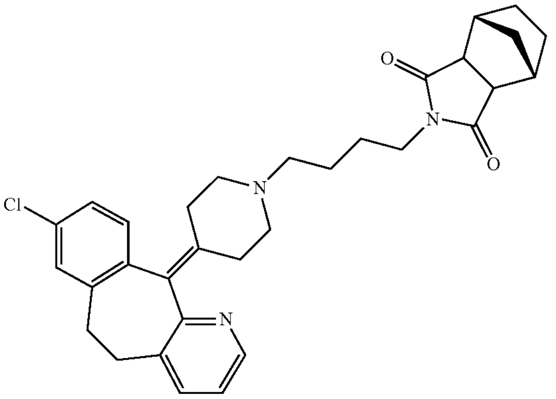 [SMILES: O=C1C2C(C(=O)N1CCCCN1CCC(=C3c4ccc(Cl)cc4CCc4cccnc43)CC1)[C@H]1CC[C@@H]2C1] | (4R,7S)-2-(4-(4-(8-chloro-5,6-dihydro-11H-benzo[5,6]cyclohepta[1,2-b]pyridin-11-ylidene)piperidin-1-yl)butyl)hexahydro-1H-4,7-methanoisoindole-1,3(2H)-dione | LC-MS (m/z): 531.2467 (M + H) |
| 31 | 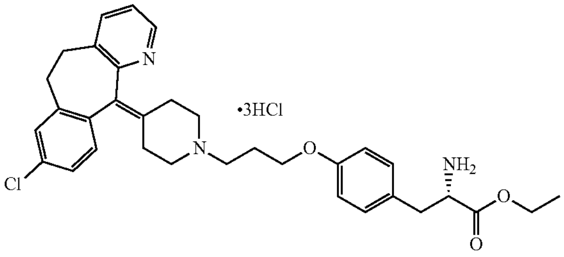 [SMILES: CCOC(=O)[C@@H](N)Cc1ccc(OCCCN2CCC(=C3c4ccc(Cl)cc4CCc4cccnc43)CC2)cc1] | ethyl (S)-2-amino-3-(4-(3-(4-(8-chloro-5,6-dihydro-11H-benzo-[5,6]cyclohepta[1,2-b]pyridin-11-ylidene)-piperidin-1-yl)propoxy)phenyl)propanoate trihydrochloride | $^1$H NMR (300 MHz, DMSO-$d_6$): δ 8.66-8.47 (m, 4H), 8.24-8.08 (in, 1H), 7.78-7.60 (m, 1H), 7.39 (d, J = 11.29 Hz, 1H), 7.29 (d, J = 8.24 Hz, 1H), 7.17-7.07 (m, 3H), 6.93-6.79 (m, 2H), 4.21-3.94 (m, 5H), 3.49-3.37 (m, 2H), 3.30-2.08 (m, 18H), 1.13 (t, J = 7.02 Hz, 3H). |
| 32 | 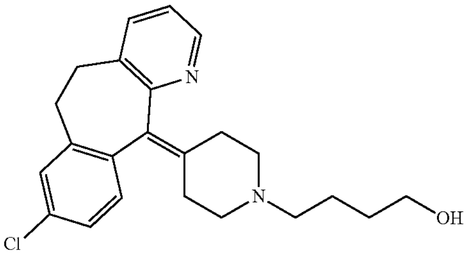 [SMILES: OCCCCN1CCC(=C2c3ccc(Cl)cc3CCc3cccnc32)CC1] | 4-(4-(8-chloro-5,6-dihydro-11H-benzo-[5,6]cyclohepta[1,2-b]pyridin-11-ylidene)-piperidin-1-yl)butan-1-ol | LC-MS (m/z): 383.1845 (M + H) |
| 33 | 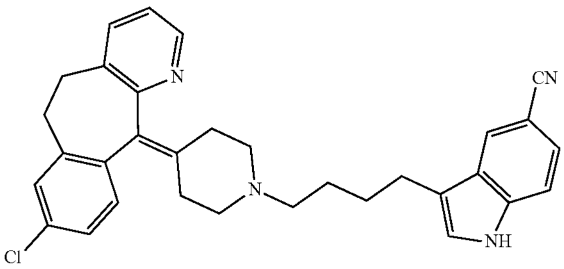 [SMILES: N#Cc1ccc2[nH]cc(CCCCN3CCC(=C4c5ccc(Cl)cc5CCc5cccnc54)CC3)c2c1] | 3-(4-(4-(8-chloro-5,6-dihydro-11H-benzo-[5,6]cyclohepta[1,2-b]pyridin-11-ylidene)-piperidin-1-yl)butyl)-1H-indole-5-carbonitrile | LC-MS (m/z): 508.2208 (M + H) |
| 34 | 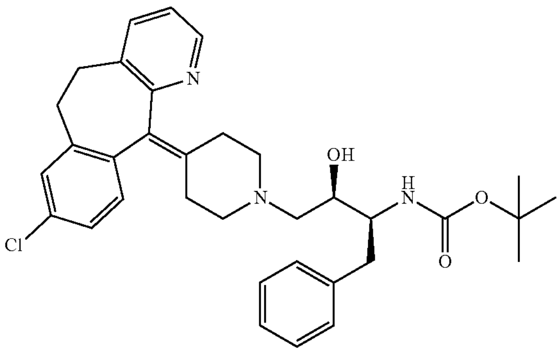 [SMILES: CC(C)(C)OC(=O)N[C@@H](Cc1ccccc1)[C@H](O)CN1CCC(=C2c3ccc(Cl)cc3CCc3cccnc32)CC1] | t-butyl ((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)-carbamate | LC-MS (m/z): 575.2729 (M + H) |

TABLE 1-continued

| No | Structure | Chemical name | NMR/MS |
|---|---|---|---|
| 35 | 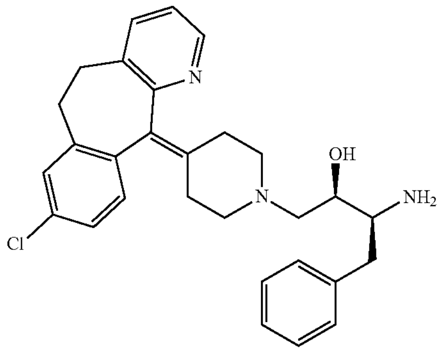 [SMILES: N[C@@H](Cc1ccccc1)[C@H](O)CN1CCC(=C2c3ccc(Cl)cc3CCc3cccnc32)CC1] | (2R,3S)-3-amino-1-(4-(8-chloro-5,6-dihydro-11H-benzo-[5,6]cyclohepta[1,2-b]pyridin-11-ylidene)-piperidin-1-yl)-4-phenylbutan-2-ol | LC-MS (m/z): 475.2204 (M + H) |
| 36 | 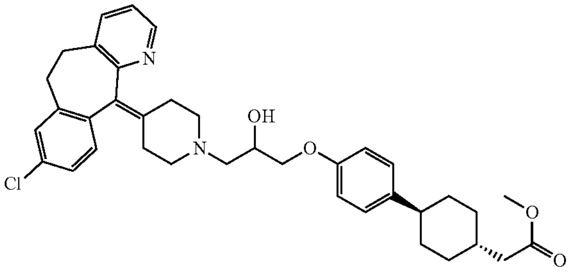 [SMILES: COC(=O)C[C@H]1CC[C@H](c2ccc(OCC(O)CN3CCC(=C4c5ccc(Cl)cc5CCc5cccnc54)CC3)cc2)CC1] | trans-methyl 2-(-4-(4-(3-(4-(8-chloro-5,6-dihydro-11H-benzo-[5,6]cyclohepta[1,2-b]pyridin-11-ylidene)-piperidin-1-yl)-2-hydroxypropoxy)-phenyl)cyclohexyl)-acetate | LC-MS (m/z): 616.2882 (M + H) |
| 37 | 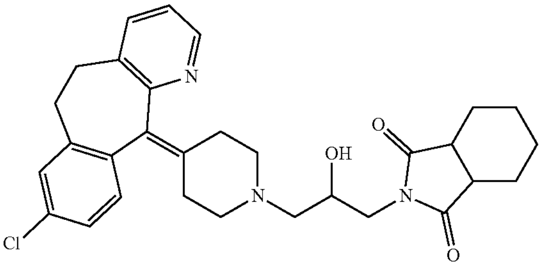 [SMILES: O=C1C2CCCCC2C(=O)N1CC(O)CN1CCC(=C2c3ccc(Cl)cc3CCc3cccnc32)CC1] | 2-(3-(4-(8-chloro-5,6-dihydro-11H-benzo-[5,6]cyclohepta[1,2-b]pyridin-11-ylidene)-piperidin-1-yl)-2-hydroxypropyl)hexa-hydro-1H-isoindole-1,3(2H)-dione | LC-MS (m/z): 521.2259 (M + H) |
| 38 | 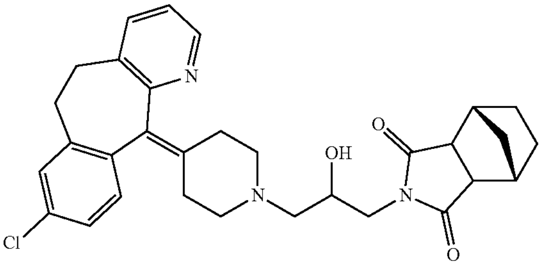 [SMILES: O=C1C2C(C(=O)N1CC(O)CN1CCC(=C3c4ccc(Cl)cc4CCc4cccnc43)CC1)[C@H]1CC[C@@H]2C1] | (4R,7S)-2-(3-(4-(8-chloro-5,6-dihydro-11H-benzo[5,6]cyclo-hepta[1,2-b]pyridin-11-ylidene)piperidin-1-yl)-2-hydroxy-propyl)hexahydro-1H-4,7-methanoiso-indole-1,3(2H)-dione | LC-MS (m/z): 533.2259 (M +H) |
| 39 | 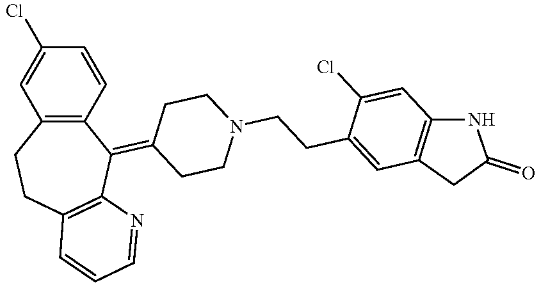 [SMILES: O=C1Cc2cc(CCN3CCC(=C4c5ccc(Cl)cc5CCc5cccnc54)CC3)c(Cl)cc2N1] | 6-chloro-5-(2-(4-(8-chloro-5,6-dihydro-11H-benzo[5,6]cyclo-hepta[1,2-b]pyridin-11-ylidene)piperidin-1-yl)ethyl)indolin-2-one | LC-MS (m/z): 505.1502 (M + H) |

TABLE 1-continued

| No | Structure | Chemical name | NMR/MS |
|---|---|---|---|
| 40 | 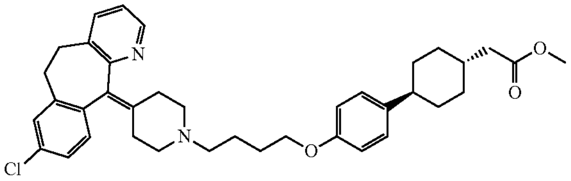 [SMILES: COC(=O)C[C@H]1CC[C@H](c2ccc(OCCCCN3CCC(=C4c5ccc(Cl)cc5CCc5cccnc54)CC3)cc2)CC1] | trans-methyl 2-(-4-(4-(4-(4-(8-chloro-5,6-dihydro-11H-benzo[5,6]cyclohepta[1,2-b]pyridin-11-ylidene)piperidin-1-yl)butoxy)phenyl)-cyclohexyl)acetate | LC-MS (m/z): 614.3089 (M + H) |
| 41 | 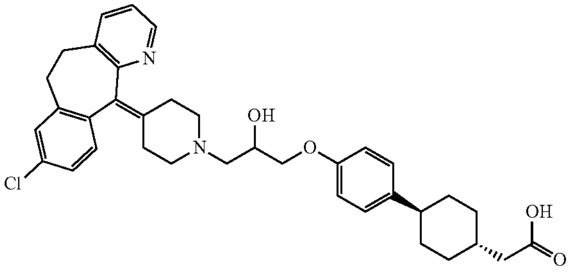 [SMILES: O=C(O)C[C@H]1CC[C@H](c2ccc(OCC(O)CN3CCC(=C4c5ccc(Cl)cc5CCc5cccnc54)CC3)cc2)CC1] | trans-2-(4-(4-(3-(4-(8-chloro-5,6-dihydro-11H-benzo[5,6]cyclohepta[1,2-b]pyridin-11-ylidene)piperidin-1-yl)-2-hydroxy-propoxy)phenyl)cyclohexyl)acetic acid | LC-MS (m/z): 602.2725 (M + H) |
| 42 | 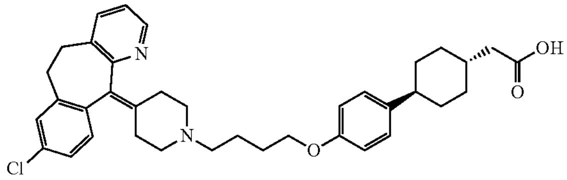 [SMILES: O=C(O)C[C@H]1CC[C@H](c2ccc(OCCCCN3CCC(=C4c5ccc(Cl)cc5CCc5cccnc54)CC3)cc2)CC1] | trans-2-(4-(4-(4-(4-(8-chloro-5,6-dihydro-11H-benzo[5,6]cyclohepta[1,2-b]pyridin-11-ylidene)piperidin-1-yl)butoxy)phenyl)-cyclohexyl)acetic acid | LC-MS (m/z): 600.2933 (M + H) |
| 43 | 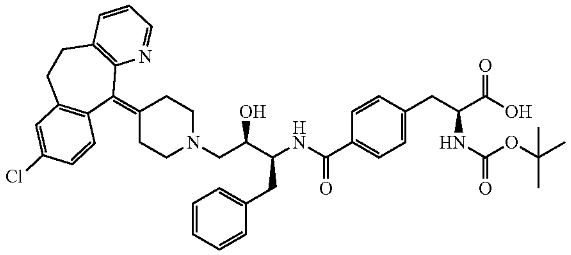 [SMILES: CC(C)(C)OC(=O)N[C@@H](Cc1ccc(C(=O)N[C@@H](Cc2ccccc2)[C@H](O)CN2CCC(=C3c4ccc(Cl)cc4CCc4cccnc43)CC2)cc1)C(=O)O] | (S)-2-((t-butoxycarbonyl)amino)-3-(4-(((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)-carbamoyl)phenyl)-propionic acid | LC-MS (m/z): 766.3311 (M + H) |
| 44 | 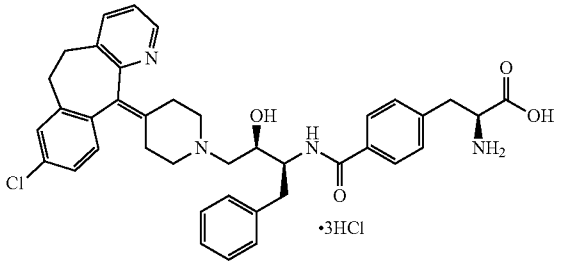 [SMILES: N[C@@H](Cc1ccc(C(=O)N[C@@H](Cc2ccccc2)[C@H](O)CN2CCC(=C3c4ccc(Cl)cc4CCc4cccnc43)CC2)cc1)C(=O)O] •3HCl | (S)-2-amino-3-(4-(((2S,3R)-4-(4-(8-chloro-5,6-dihydro-11H-benzo[5,6]cyclohepta[2,2-b]pyridin-11-ylidene)piperidin-1-yl)-3-hydroxy-1-phenylbutan-2-yl)-carbamoyl)phenyl)-propionic acid trihydrochloride | LC-MS (m/z): 666.2787 (M + H) |
| 45 | 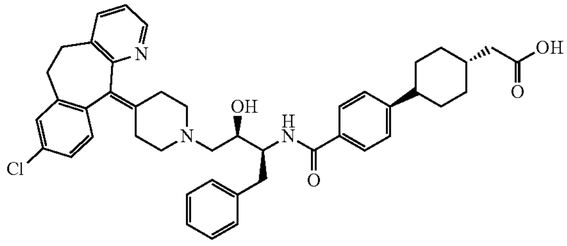 | trans-2-(4-(4-(((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)-carbamoyl)phenyl)-cyclohexyl)acetic acid | LC-MS (m/z): 719.3304 (M + H) |

TABLE 1-continued

| No | Structure | Chemical name | NMR/MS |
| --- | --- | --- | --- |
| 46 | 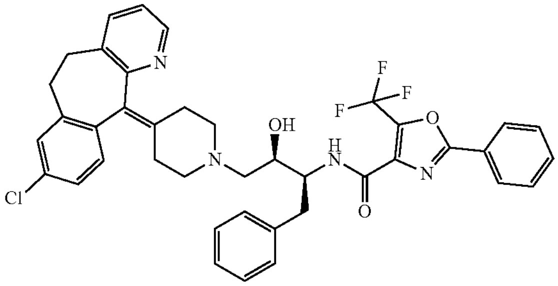 [SMILES: O=C(N[C@@H](Cc1ccccc1)[C@H](O)CN1CCC(=C2c3ccc(Cl)cc3CCc3cccnc32)CC1)c1nc(-c2ccccc2)oc1C(F)(F)F] | N-((2S,3R)-4-(4-(8-chloro-5,6-dihydro-11H-benzo[5,6]cyclo-hepta[1,2-b]pyridin-11-ylidene)piperidin-1-yl)-3-hydroxy-1-phenylbutan-2-yl)-2-phenyl-5-(trifluoro-methyl)oxazole-4-carboxamide | LC-MS (m/z): 714.2399 (M + H) |
| 47 | 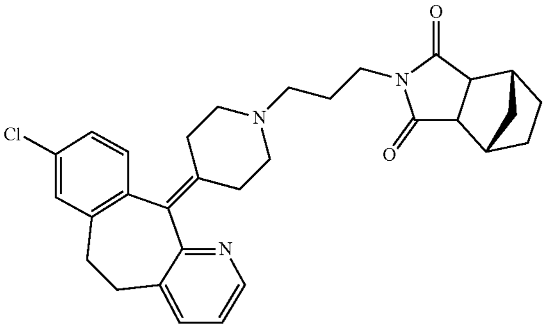 [SMILES: O=C1C2C(C(=O)N1CCCN1CCC(=C3c4ccc(Cl)cc4CCc4cccnc43)CC1)[C@H]1CC[C@@H]2C1] | (4R,7S)-2-(3-(4-(8-chloro-5,6-dihydro-11H-benzo[5,6]-cyclohepta[1,2-b]-pyridin-11-ylidene)-piperidin-1-yl)-propyl)hexahydro-1H-4,7-methanoiso-indole-1,3(2H)-dione | LC-MS (m/z): 517.2310 (M + H) |
| 48 | 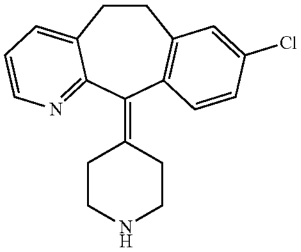 [SMILES: Clc1ccc2c(c1)CCc1cccnc1C2=C1CCNCC1] | 8-chloro-11-(piperi-din-4-ylidene)-6,11-dihydro-5H-benzo-[5,6]cyclohepta[1,2-b]pyridine | LC-MS (m/z): 311.1270 (M + H) |
| 49 | 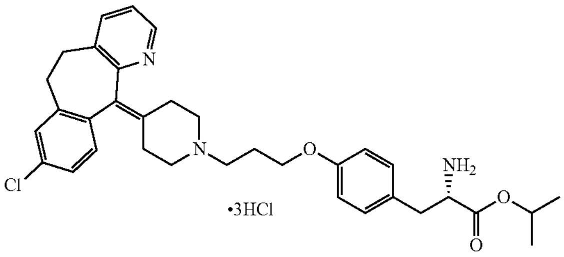 [SMILES: CC(C)OC(=O)[C@@H](N)Cc1ccc(OCCCN2CCC(=C3c4ccc(Cl)cc4CCc4cccnc43)CC2)cc1] •3HCl | isopropyl (S)-2-amino-3-(4-(3-(4-(8-chloro-5,6-dihydro-11H-benzo[5,6]cyclo-hepta[1,2-b]pyridin-11-ylidene)piperidin-1-yl)propoxy)phenyl)-propanoate trihydro-chloride | $^{1}$H NMR (300 MHz, DMSO-$d_6$): δ 8.60 (s, 5H), 8.23 (s, 1H), 7.83-7.68 (m, 1H), 7.40 (d, J = 10.99 Hz, 1H), 7.30 (d, J = 8.24 Hz, 1H), 7.24 (d, J = 8.24 Hz, 1H), 7.18-7.04 (m, 3H), 6.93-6.75 (m, 2H), 4.92-4.74 (m, 1H), 4.16-3.88 (m, 3H), 3.56-2.72 (m, 13 H), 2.70-2.07 (m, 5H), 1.17-1.07 (m, 6H). |
| 50 | 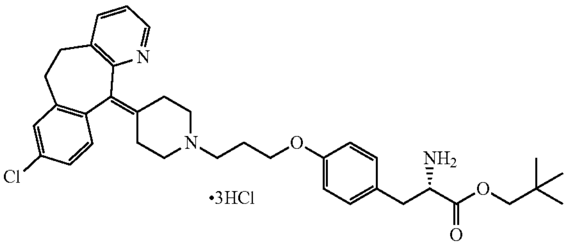 [SMILES: CC(C)(C)COC(=O)[C@@H](N)Cc1ccc(OCCCN2CCC(=C3c4ccc(Cl)cc4CCc4cccnc43)CC2)cc1] •3HCl | neopentyl (S)-2-amino-3-(4-(3-(4-(8-chloro-5,6-dihydro-11H-benzo[5,6]cyclo-hepta[1,2-b]pyridin-11-ylidene)piperidin-1-yl)propoxy)phenyl)-propanoate trihydro-chloride | $^{1}$H NMR (300 MHz, DMSO-$d_6$): δ 8.61 (s, 4H), 8.21 (s, 1H), 7.74 (s, 1H), 7.43 (d, J = 10.99 Hz, 1H), 7.33 (d, J = 8.24 Hz, 1H), 7.29-7.11 (m, 3H), 6.97-6.84 (m, 2H), 4.29-4.15 (m, 1H), 4.07-3.91 (m, 2H), 3.81-3.60 (m, 2H), 3.50-3.05 (m, 6H), 3.05-2.67 (m, 6H), 2.66-2.03 (m, 6H), 0.76 (s, 9H). |

TABLE 1-continued

| No | Structure | Chemical name | NMR/MS |
|---|---|---|---|
| 51 | 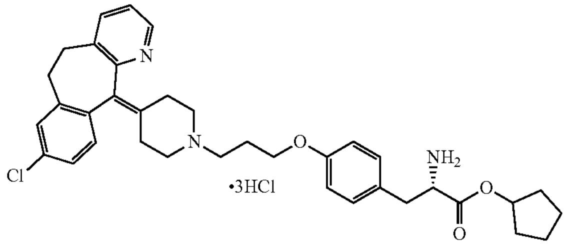 [SMILES: N[C@@H](Cc1ccc(OCCCN2CCC(=C3c4ccc(Cl)cc4CCc4cccnc43)CC2)cc1)C(=O)OC1CCCC1] | cyclopentyl (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)-propanoate trihydrochloride | $^{1}$H NMR (300 MHz, DMSO-$d_6$): δ 8.66-8.52 (m, 4H), 8.22 (s, 1H), 7.76 (s, 1H), 7.43 (dd, J = 11.14, 2.14 Hz, 1H), 7.33 (dd, J = 8.24 , 2.14 Hz, 1H), 7.29-7.09 (m, 3H), 6.90 (dd, J = 18.62, 8.54 Hz, 2H), 5.11-5.0 (m, 1H), 4.18-3.95 (m, 3H), 3.54-3.37 (m, 2H), 3.33-2.71 (m, 8H), 2.68-2.32 (m, 6H), 2.31-2.08 (m, 2H), 1.83-1.65 (m, 2H), 1.63-1.31 (m, 6H). |
| 52 | 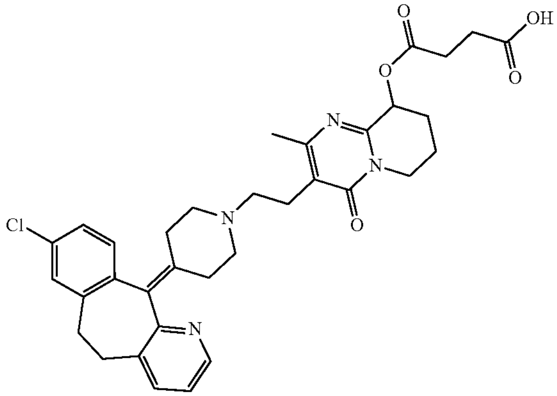 [SMILES: Cc1nc2n(c(=O)c1CCN1CCC(=C3c4ccc(Cl)cc4CCc4cccnc43)CC1)CCCC2OC(=O)CCC(=O)O] | 4-((3-(2-(4-(8-chloro-5,6-dihydro-11H-benzo[5,6]cyclohepta-[1,2-b]pyridin-11-ylidene)piperidin-1-yl)ethyl)-2-methyl-4-oxo-6,7,8,9-tetra-hydro-4H-pyrido[1,2-a]pyrimidin-9-yl)oxy)-4-oxobutanoic acid | $^{1}$H NMR (300 MHz, DMSO-$d_6$): δ 12.40 (s, 1H), 8.29 (d, J = 4.27 Hz, 1H), 7.53 (d, J = 7.63 Hz, 1H), 7.25 (s, 1H), 7.15 (t, J = 7.93 Hz, 2H), 7.03 (d, J = 8.24 Hz, 1H), 5.64-5.57 (m, 1H), 3.94-3.82 (m, 1H), 3.69-3.56 (m, 1H), 3.38-3.16 (m, 4H), 2.85-2.61 (m, 4H), 2.60-2.41 (m, 4H), 2.16 (s, 3H), 2.37-2.07 (m, 10H), 2.05-1.79 (m, 4H). |
| 53 | 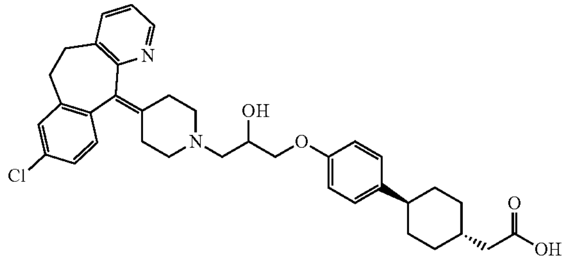 [SMILES: O=C(O)C[C@H]1CC[C@H](c2ccc(OCC(O)CN3CCC(=C4c5ccc(Cl)cc5CCc5cccnc54)CC3)cc2)CC1] | 2-((1R,4R)-4-(4-(3-(4-(8-chloro-5,6-dihydro-11H-benzo-[5,6]cyclohepta[1,2-b]pyridin-11-ylidene)-piperidin-1-yl)-2-hydroxypropoxy)-phenyl)cyclohexyl)-acetic acid | $^{1}$H NMR (300 MHz, DMSO-$d_6$): δ 11.98 (s, 1H), 8.36 (s, 1H), 7.70-7.54 (m, 1H), 7.39-7.33 (m, 1H), 7.31-7.07 (m, 5H), 6.93-6.80 (m, 2H), 5.92 (s, 1H), 4.47-4.23 (m, 1H), 4.05-3.79 (m, 2H), 3.75-3.07 (m, 8H), 3.06-2.30 (m, 7H), 2.12 (d, J = 3.97 Hz, 2H), 1.87-1.61 (m, 5H), 1.49-1.31 (m, 2H), 1.18-1.0 (m, 2H). |
| 54 | 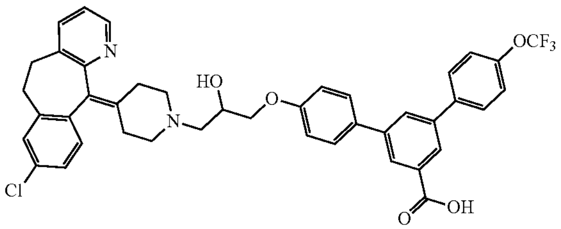 [SMILES: O=C(O)c1cc(-c2ccc(OCC(O)CN3CCC(=C4c5ccc(Cl)cc5CCc5cccnc54)CC3)cc2)cc(-c2ccc(OC(F)(F)F)cc2)c1] | 4-(3-(4-(8-chloro-5,6-dihydro-11H-benzo-[5,6]cyclohepta[1,2-b]pyridin-1-ylidene)-piperidin-1-yl)-2-hydroxypropoxy)-4"-(trifluoromethoxy)-[1,1':3',1"-terphenyl]-5'-carboxylic acid | $^{1}$H NMR (300 MHz, DMSO-$d_6$): δ 8.40-8.30 (m, 1H), 8.17-8.05 (m, 3H), 7.99-7.87 (m, 2H), 7.76 (d, J = 8.54 Hz, 2H), 7.57 (d, J = 7.32 Hz, 1H), 7.48 (d, J = 7.63 Hz, 2H), 7.37-7.16 (m, 3H), 7.12-7.01 (m, 3H), 4.13-3.91 (m, 3H), 3.04-2.17 (m, 14H). |

TABLE 1-continued

| No | Structure | Chemical name | NMR/MS |
| --- | --- | --- | --- |
| 55 | 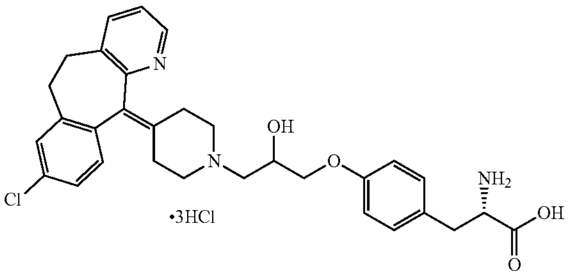 [SMILES: N[C@@H](Cc1ccc(OCC(O)CN2CCC(=C3c4ccc(Cl)cc4CCc4cccnc43)CC2)cc1)C(=O)O] | (2S)-2-amino-3-(4-(3-(4-(8-chloro-5,6-dihydro-11H-benzo-[5,6]cyclohepta[1,2-b]pyridin-11-ylidene)-piperidin-1-yl)-2-hydroxypropoxy)-phenyl)propionic acid trihydrochloride | $^1$H NMR (300 MHz, DMSO-$d_6$): δ 8.58 (s, 1H), 8.40 (s, 3H), 8.19 (s, 1H), 7.78-7.58 (m, 1H),? 7.48-7.08 (m, 4H), 7.0-6.8 (m, 4H), 6.75-6.55 (m, 1H), 4.50-4.30 (m, 1H), 4.27-2.71 (m, 17H), 2.17 (d, J = 2.14 Hz, 2H) |
| 56 | 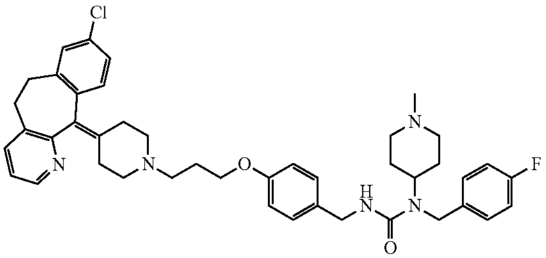 [SMILES: CN1CCC(N(Cc2ccc(F)cc2)C(=O)NCc2ccc(OCCCN3CCC(=C4c5ccc(Cl)cc5CCc5cccnc54)CC3)cc2)CC1] | 3-(4-(3-(4-(8-chloro-5,6-dihydro-11H-benzo[5,6]cyclohepta-[1,2-b]pyridin-11-ylidene)piperidin-1-yl)propoxy)benzyl)-1-(4-fluorobenzyl)-1-(1-methylpiperidin-4-yl)urea | LCMS [M + H] 722.36 |
| 57 | 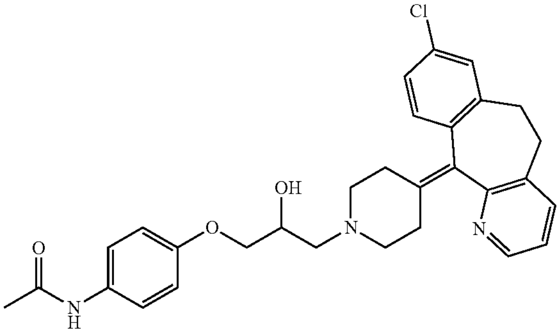 [SMILES: CC(=O)Nc1ccc(OCC(O)CN2CCC(=C3c4ccc(Cl)cc4CCc4cccnc43)CC2)cc1] | N-(4-(3-(4-(8-chloro-5,6-dihydro-11H-benzo[5,6]cyclohepta-[1,2-b]pyridin-11-ylidene)piperidin-1-yl)-2-hydroxypro-poxy)phenyl)acetamide | LCMS [M + H] 518.21 |
| 58 | 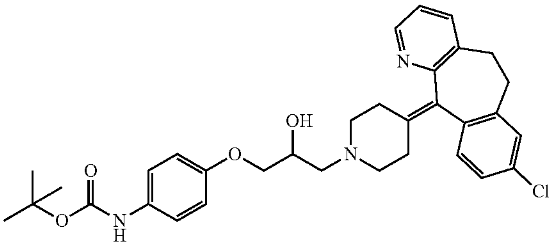 [SMILES: CC(C)(C)OC(=O)Nc1ccc(OCC(O)CN2CCC(=C3c4ccc(Cl)cc4CCc4cccnc43)CC2)cc1] | t-butyl (4-(3-(4-(8-chloro-5,6-dihydro-11H-benzo[5,6]cyclo-hepta[1,2-b]pyridin-11-ylidene)piperidin-1-yl)-2-hydroxypro-poxy)phenyl)carbamate | LCMS [M + H] 576.26 |
| 59 | 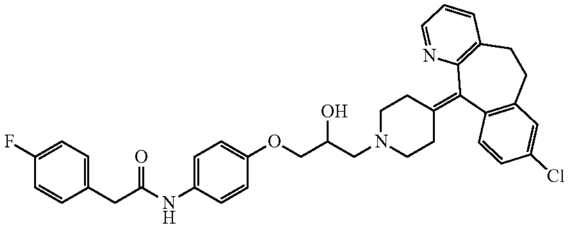 [SMILES: O=C(Cc1ccc(F)cc1)Nc1ccc(OCC(O)CN2CCC(=C3c4ccc(Cl)cc4CCc4cccnc43)CC2)cc1] | N-(4-(3-(4-(8-chloro-5,6-dihydro-11H-benzo[5,6]cyclohepta-[1,2-b]pyridin-11-ylidene)piperidin-1-yl)-2-hydroxypro-poxy)phenyl)-2-(4-fluorophenyl)acetamide | LCMS [M + H] 612.24 |

TABLE 1-continued

| No | Structure | Chemical name | NMR/MS |
|---|---|---|---|
| 60 | 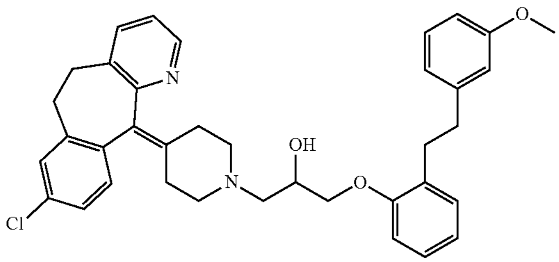 [SMILES: COc1cccc(CCc2ccccc2OCC(O)CN2CCC(=C3c4ccc(Cl)cc4CCc4cccnc43)CC2)c1] | 1-(4-(8-chloro-5,6-dihydro-11H-benzo-[5,6]cyclohepta[1,2-b]pyridin-11-ylidene)-piperidin-1-yl)-3-(2-(3-methoxyphenethyl)phenoxy)propan-2-ol | $^1$H NMR (300 MHz, DMSO-$d_6$): δ 8.33 (s, 1H), 7.57 (d, J = 6.41 Hz, 1H), 7.30 (s, 1H), 7.26-7.02 (m, 6H), 6.94 (d, J = 7.63 Hz, 1H), 6.89-6.75 (m, 3H), 6.70 (d, J = 7.32 Hz, 1H), 4.11-3.85 (m, 3H), 3.66 (s, 3H), 3.50-3.20 (m, 6H), 3.06-2.64 (m, 8H), 2.46-2.06 (m, 4H). |
| 61 | 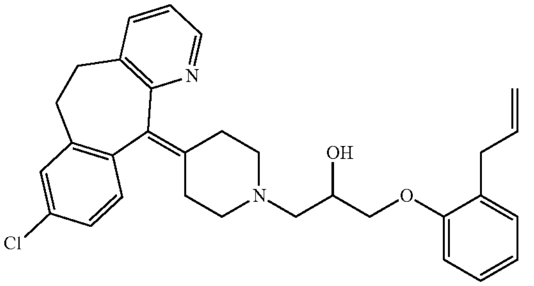 [SMILES: C=CCc1ccccc1OCC(O)CN1CCC(=C2c3ccc(Cl)cc3CCc3cccnc32)CC1] | 1-(2-allylphenoxy)-3-(4-(8-chloro-5,6-dihydro-1H-benzo-[5,6]cyclohepta[1,2-b]pyridin-11-ylidene)-piperidin-1-yl)propan-2-ol | $^1$H NMR (300 MHz, $CDCl_3$): δ 8.43-8.31 (m, 1H), 7.41 (d, J = 7.63 Hz, 1H), 7.21-6.97 (m, 6H), 6.88 (t, J = 7.32 Hz, 1H), 6.83 (d, J = 8.24 Hz, 1H), 6.03-5.83 (m, 1H), 5.07-4.89 (m, 2H), 4.17-3.85 (m, 3H), 3.68-3.10 (m, 5H), 2.98-2.65 (m, 4H), 2.63-2.09 (m, 7H). |
| 62 | 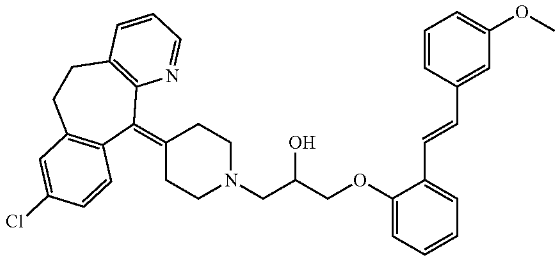 [SMILES: COc1cccc(/C=C/c2ccccc2OCC(O)CN2CCC(=C3c4ccc(Cl)cc4CCc4cccnc43)CC2)c1] | (E)-1-(4-(8-chloro-5,6-dihydro-11H-benzo[5,6]cyclohepta-[1,2-b]pyridin-11-ylidene)piperidin-1-yl)-3-(2-(3-methoxystyryl)phenoxy)propan-2-ol | $^1$H NMR (300 MHz, $CDCl_3$): δ 8.39 (d, J = 4.58 Hz, 1H), 7.56 (d, J = 7.63 Hz, 1H), 7.48-7.37 (m, 2H), 7.21 (q, J = 8.77 Hz, 2H), 7.17-7.01 (m, 7H), 6.96 (t, J = 7.63 Hz, 1H), 6.89 (d, J = 8.39 Hz, 1H), 6.78 (d, J = 8.01 Hz, 1H), 4.20-3.94 (m, 3H), 3.79 (s, 3H), 3.45-3.28 (m, 2H), 3.0-2.68 (m, 4H), 2.67-2.29 (m, 7H), 2.25-2.12 (m, 1H). |
| 63 | 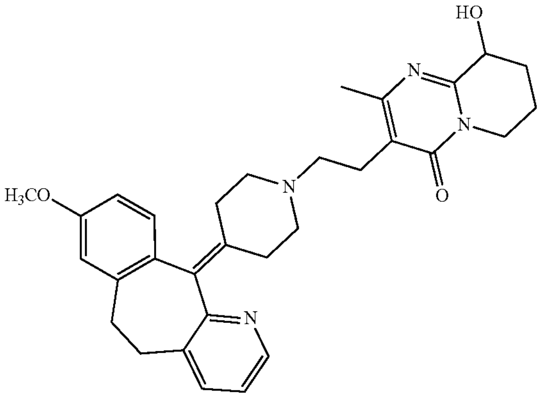 [SMILES: COc1ccc2c(c1)CCc1cccnc1C2=C1CCN(CCc2c(C)nc3n(c2=O)CCCC3O)CC1] | 9-hydroxy-3-(2-(4-(8-methoxy-5,6-dihydro-11H-benzo-[5,6]cyclohepta[1,2-b]pyridin-11-ylidene)-piperidin-1-yl)ethyl)-2-methyl-6,7,8,9-tetrahydro-4H-pyrido-[1,2-a]pyrimidin-4-one | LCMS [M + H] 513.65 |

TABLE 1-continued

| No | Structure | Chemical name | NMR/MS |
|---|---|---|---|
| 64 | 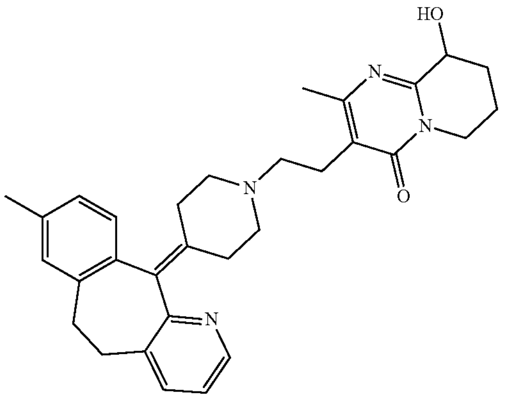 [SMILES: Cc1ccc2c(c1)CCc1cccnc1C2=C1CCN(CCc2c(C)nc3n(c2=O)CCCC3O)CC1] | 9-hydroxy-2-methyl-3-(2-(4-(8-methyl-5,6-dihydro-11H-benzo-[5,6]cyclohepta[1,2-b]pyridin-11-ylidene)-piperidin-1-yl)ethyl)-6,7,8,9-tetrahydro-4H-pyrido[1,2-a]-pyrimidin-4-one | LCMS [M + H] 497.66 |
| 65 | 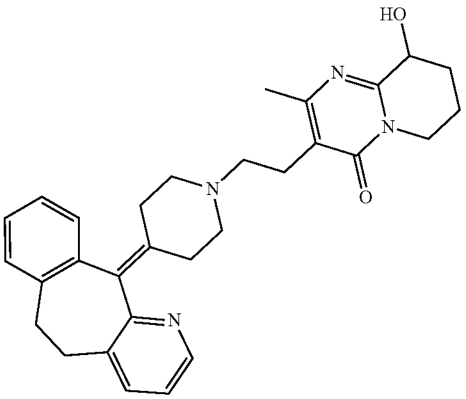 [SMILES: Cc1nc2n(c(=O)c1CCN1CCC(=C3c4ccccc4CCc4cccnc43)CC1)CCCC2O] | 3-(2-(4-(5,6-dihydro-11H-benzo[5,6]cyclo-hepta[1,2-b]pyridin-11-ylidene)piperidin-1-yl)ethyl)-9-hydroxy-2-methyl-6,7,8,9-tetrahydro-4H-pyrido-[1,2-a]pyrimidin-4-one | LCMS [M + H] 483.63 |
| 66 | 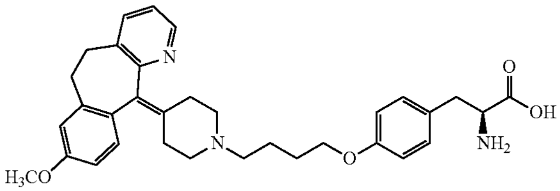 [SMILES: COc1ccc2c(c1)CCc1cccnc1C2=C1CCN(CCCCOc2ccc(C[C@H](N)C(=O)O)cc2)CC1] | (S)-2-amino-3-(4-(4-(4-(8-methoxy-5,6-dihydro-11H-benzo-[5,6]cyclohepta[1,2-b]pyridin-11-ylidene)-piperidin-1-yl)-butoxy)phenyl)pro-pionic acid trihydro-chloride | LCMS [M + H] 542.69 |
| 67 | 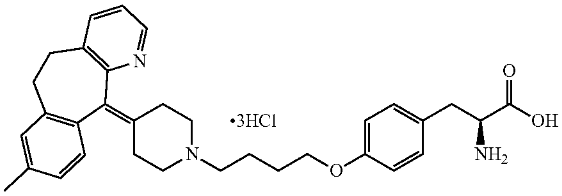 [SMILES: Cc1ccc2c(c1)CCc1cccnc1C2=C1CCN(CCCCOc2ccc(C[C@H](N)C(=O)O)cc2)CC1] | (S)-2-amino-3-(4-(4-(4-(8-methyl-5,6-dihydro-11H-benzo-[5,6]cyclohepta[1,2-b]pyridin-11-ylidene)-piperidin-1-yl)-butoxy)phenyl)pro-pionic acid trihydro-chloride | LCMS [M + H] 526.69 |
| 68 | 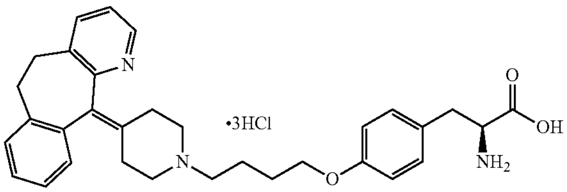 [SMILES: N[C@@H](Cc1ccc(OCCCCN2CCC(=C3c4ccccc4CCc4cccnc43)CC2)cc1)C(=O)O] | (S)-2-amino-3-(4-(4-(4-(5,6-dihydro-11H-benzo[5,6]cyclohepta-[1,2-b]pyridin-11-ylidene)piperidin-1-yl)butoxy)phenyl)-propionic acid tri-hydrochloride | LCMS [M + H] 512.67 |

TABLE 1-continued

| No | Structure | Chemical name | NMR/MS |
|---|---|---|---|
| 69 | 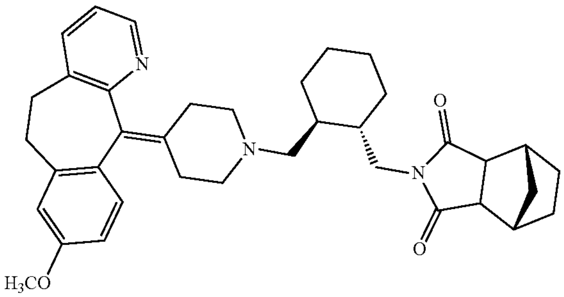 [SMILES: COc1ccc2c(c1)CCc1cccnc1C2=C1CCN(C[C@H]2CCCC[C@@H]2CN2C(=O)C3C(C2=O)[C@H]2CC[C@@H]3C2)CC1] | (4R,7S)-2-((trans-2-((4-(8-methoxy-5,6-dihydro-11H-benzo-[5,6]cyclohepta[1,2-b]pyridin-11-ylidene)-piperidin-1-yl)meth-yl)cyclohexyl)meth-yl)hexahydro-1H-4,7-methanoisoindole-1,3(2H)-dione | LCMS [M + H] 580.79 |
| 70 | 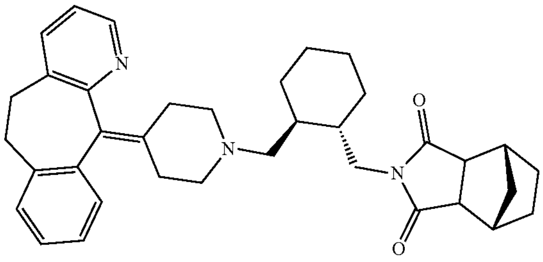 [SMILES: O=C1C2C(C(=O)N1C[C@H]1CCCC[C@@H]1CN1CCC(=C3c4ccccc4CCc4cccnc43)CC1)[C@H]1CC[C@@H]2C1] | (4R,7S)-2-((trans-2-((4-(5,6-dihydro-11H-benzo[5,6]cyclohepta-[1,2-b]pyridin-11-ylidene)piperidin-1-yl)methyl)cyclohex-yl)methyl)hexahydro-1H-4,7-methanoiso-indole-1,3(2H)-dione | LCMS [M + H] 550.76 |
| 71 | 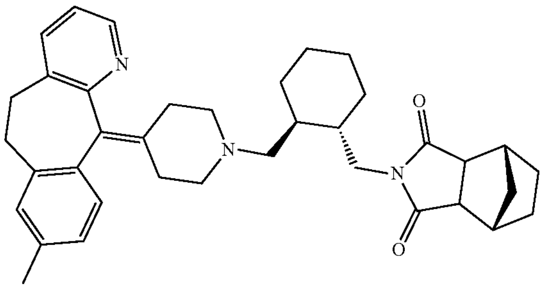 [SMILES: Cc1ccc2c(c1)CCc1cccnc1C2=C1CCN(C[C@H]2CCCC[C@@H]2CN2C(=O)C3C(C2=O)[C@H]2CC[C@@H]3C2)CC1] | (4R,7S)-2-((trans-2-((4-(8-methyl-5,6-dihydro-11H-benzo-[5,6]cyclohepta[1,2-b]pyridin-11-ylidene)-piperidin-1-yl)meth-yl)cyclohexyl)meth-yl)hexahydro-1H-4,7-methanoisoindole-1,3(2H)-dione | LCMS [M + H] 564.79 |
| 72 | 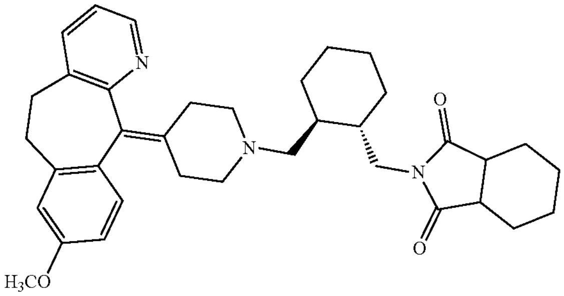 [SMILES: COc1ccc2c(c1)CCc1cccnc1C2=C1CCN(C[C@H]2CCCC[C@@H]2CN2C(=O)C3CCCCC3C2=O)CC1] | 2-((trans-2-((4-(8-methoxy-5,6-dihydro-11H-benzo[5,6]cyclo-hepta[1,2-b]pyridin-11-ylidene)piperidin-1-yl)methyl)cyclo-hexyl)methyl)hexa-hydro-1H-isoindole-1,3(2H)-dione | LCMS [M + H] 568.77 |
| 73 | 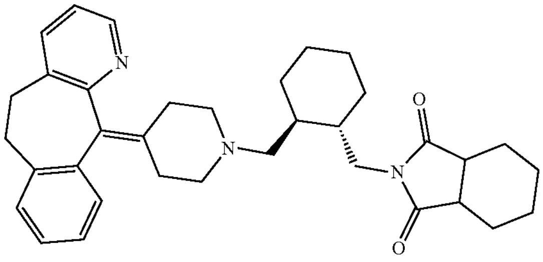 [SMILES: O=C1C2CCCCC2C(=O)N1C[C@H]1CCCC[C@@H]1CN1CCC(=C2c3ccccc3CCc3cccnc32)CC1] | 2-((trans-2-((4-(5,6-dihydro-11H-benzo-[5,6]cyclohepta[1,2-b]pyridin-11-ylidene)-piperidin-1-yl)meth-yl)cyclohexyl)meth-yl)hexahydro-1H-isoindole-1,3(2H)-dione | LCMS [M + H] 538.75 |

TABLE 1-continued

| No | Structure | Chemical name | NMR/MS |
| --- | --- | --- | --- |
| 74 | 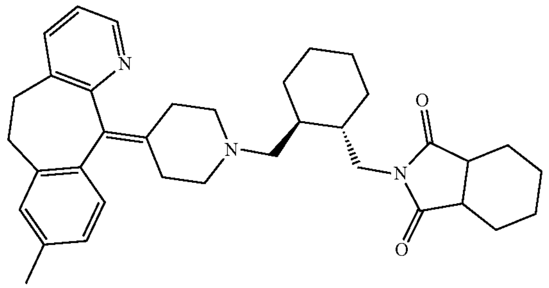 [SMILES: Cc1ccc2c(c1)CCc1cccnc1C2=C1CCN(C[C@H]2CCCC[C@@H]2CN2C(=O)C3CCCCC3C2=O)CC1] | 2-((trans-2-((4-(8-methyl-5,6-dihydro-11H-benzo[5,6]cyclo-hepta[1,2-b]pyridin-11-ylidene)piperidin-1-yl)methyl)cyclo-hexyl)methyl)hexa-hydro-1H-isoindole-1,3(2H)-dione | LCMS [M + H] 552.78 |

Experimental Example: Measurement of Inhibitory Activity Against Serotonin 2A Receptor The inhibitory activity of the compounds synthesized in Examples against serotonin 2A (5-$HT_{2A}$) receptor was measured (in vitro), and the results thereof are shown in Table 2 below.

TABLE 2

| Example No. | $IC_{50}$ (nM) |
| --- | --- |
| 2 | 232 |
| 9 | 14 |
| 10 | 14 |
| 12 | 47 |
| 13 | 119 |
| 14 | 188 |
| 15 | 30 |
| 18 | 1.3 |
| 19 | 0.19 |
| 20 | 2.08 |
| 21 | 2.1 |
| 22 | 1.3 |
| 24 | 8.1 |
| 25 | 2.3 |
| 26 | 4.05 |
| 27 | 1.19 |
| 30 | 0.15 |
| 60 | 30.8 |

As shown in Table 2, the inhibitory activity of the compounds of Examples against serotonin 2A receptor could be confirmed. Therefore, the compound according to the present invention can be usefully used for the prevention or treatment of diseases associated with serotonin activation, for example, metabolic diseases such as obesity, fatty liver and steatohepatitis.

The invention claimed is:

1. A compound of Formula 1a to 1c or a pharmaceutically acceptable salt thereof (Formula 1a)

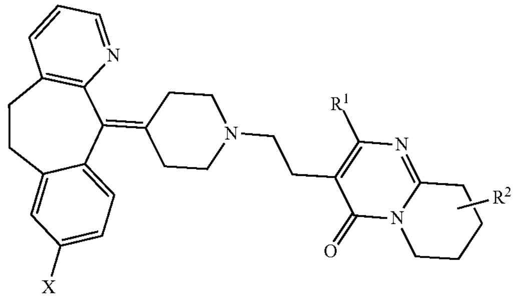

wherein:

X is H, a halogen, $C_{1-6}$ alkyl, or $C_{1-6}$ alkoxy; and $R^1$ and $R^2$ are each independently H, —OH, —F, —Cl, —Br, —$CF_3$, —CN, —COOH, or $C_{1-3}$ alkyl; or

[Chemical Formula 1b]

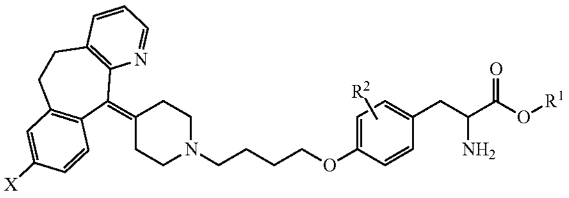

wherein:

X is H, a halogen, $C_{1-6}$ alkyl, or $C_{1-6}$ alkoxy; and $R^1$ and $R^2$ are each independently H, —Cl, or $C_{1-3}$ alkyl; or

[Chemical Formula 1c]

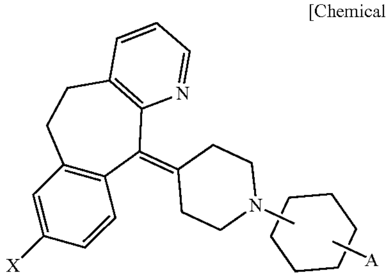

wherein:

X is H, a halogen, $C_{1-6}$ alkyl, or $C_{1-6}$ alkoxy;

A is

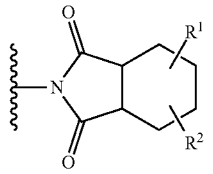 or 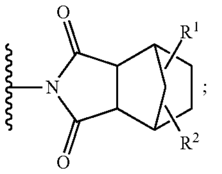 ;

and $R^1$ and $R^2$ are both H.

2. A compound or a pharmaceutically acceptable salt thereof, selected from the group consisting of:

3) 8-chloro-11-(1-(methylsulfonyl)piperidin-4-ylidene)-6,11-dihydro-5H -benzo[5,6]cyclohepta[1,2-b]pyridine;

4) 4-(8-chloro-5,6-dihydro-11H-benzo[5,6]cyclohepta[1,2-b]pyridin-11-ylidene)-N -isopropylpiperidine-1-carbothioamide;

6) (R)-3-amino-1-(4-(8-chloro-5,6-dihydro-11H-benzo[5,6]cyclohepta[1,2-b]pyridin -11-ylidene)piperidin-1-yl)-4-(2,4,5-trifluorophenyl)butan-1-one dihydrochloride;

7) (S)-2-amino-3-(4-(4-(8-chloro-5,6-dihydro-11H-benzo[5,6]cyclohepta[1,2-b]pyridin -11-ylidene)piperidine-1-carbonyl)phenyl)propionic acid dihydrochloride;

8) (S)-1-(2-amino-4-(4-(8-chloro-5,6-dihydro-11H-benzo[5,6]cyclohepta[1,2-b]pyridin -11-ylidene)piperidin-1-yl)-4-oxobutyl)-5,5-difluoropiperidin-2-one dihydrochloride;

9) 3-(2-(4-(8-chloro-5,6-dihydro-11H-benzo[5,6]cyclohepta[1,2-b]pyridin-11-ylidene) piperidin-1-yl)ethyl)-2-methyl-6,7,8,9-tetrahydro-4H-pyrido[1,2-a]pyrimidin-4-one;

10) 3-(2-(4-(8-chloro-5,6-dihydro-11H-benzo[5,6]cyclohepta[1,2-b]pyridin-11-ylidene) piperidin-1-yl)ethyl)-9-hydroxy-2-methyl-6,7,8,9-tetrahydro-4H-pyrido[1,2-a]pyrimidin-4-one;

11) 2-(4-(8-chloro-5,6-dihydro-11H-benzo[5,6]cyclohepta[1,2-b]pyridin-11-ylidene)piperidin-1-yl)-1-(6-methylimidazo[2, 1-b]thiazol-5-yl)ethan-1-one;

12) 3-(2-(4-(8-chloro-5,6-dihydro-11H-benzo[5,6]cyclohepta[1,2-b]pyridin-11-ylidene)piperidin-1-yl)ethyl) quinazoline-2,4(1H,3H)-dione;

14) (S)-2-amino-3-(4-(4-(4-(8-chloro-5,6-dihydro-11H-benzo[5,6]cyclohepta[1,2-b]pyridin-11-ylidene)piperidin-1-yl)butoxy)phenyl)propionic acid trihydrochloride;

15) 2-(4-(8-chloro-5,6-dihydro-11H-benzo[5,6]cyclohepta[1,2-b]pyridin-11-ylidene)piperidin-1-yl)-1-(6-methylimidazo[2, 1-b]thiazol-5-yl)ethan-1-ol;

16) ethyl(S)-2-((t-butoxycarbonyl)amino)-3-(4-(4-(4-(8-chloro-5,6-dihydro-11H -benzo[5,6]cyclohepta[1,2-b]pyridin-11-ylidene)piperidin-1-yl)butoxy)phenyl)propanoate;

17) (S)-2-((t-butoxycarbonyl)amino)-3-(4-(4-(4-(8-chloro-5,6-dihydro-11H -benzo[5,6]cyclohepta[1,2-b]pyridin-11-ylidene)piperidin-1-yl)butoxy)phenyl)propionic acid;

18) 7-(4-(4-(8-chloro-5,6-dihydro-11H-benzo[5,6]cyclohepta[1,2-b]pyridin-11-ylidene)piperidin-1-yl)butoxy)-3,4-dihydroquinolin-2(1H)-one;

19) 2-(4-(4-(8-chloro-5,6-dihydro-11H-benzo[5,6]cyclohepta[1,2-b]pyridin-11-ylidene)piperidin-1-yl)butyl) hexahydro-1H-isoindole-1,3(2H)-dione;

20) (S)-2-amino-3-(3-chloro-4-(4-(4-(8-chloro-5,6-dihydro-11H -benzo[5,6]cyclohepta[1,2-b]pyridin-11-ylidene)piperidin-1-yl)butoxy)phenyl)propionic acid trihydrochloride;

21) (S)-2-amino-3-(3-chloro-4-(3-(4-(8-chloro-5,6-dihydro-11H -benzo[5,6]cyclohepta[1,2-b]pyridin-11-ylidene)piperidin-1-yl)propoxy)phenyl)propionic acid trihydrochloride;

22) (S)-2-amino-3-(4-(3-(4-(8-chloro-5,6-dihydro-11H-benzo[5,6]cyclohepta[1,2-b]pyridin-11-ylidene)piperidin-1-yl)propoxy)phenyl)propionic acid trihydrochloride;

23) (2S,4S)-4-(4-(8-chloro-5,6-dihydro-11H-benzo[5,6] cyclohepta[1,2-b]pyridin-11-ylidene)piperidin-1-yl) pyrrolidine-2-carboxylic acid trihydrochloride;

24) 1-(4-bromophenyl)-2-(4-(8-chloro-5,6-dihydro-11H-benzo[5,6]cyclohepta[1,2-b]pyridin-11-ylidene)piperidin-1-yl)ethan-1-one;

25) (4R,7S)-2-(((1S,2S)-2-((4-(8-chloro-5,6-dihydro-11H-benzo[5,6]cyclohepta[1,2-b]pyridin-11-ylidene) piperidin-1-yl)methyl)cyclohexyl)methyl)hexahydro-1H-4,7-methanoisoindole-1,3(2H)-dione;

26) 2-(((1S,2S)-2-((4-(8-chloro-5,6-dihydro-11H-benzo [5,6]cyclohepta[1,2-b]pyridin-11-ylidene)piperidin-1-yl)methyl)cyclohexyl)methyl)hexahydro-1H-isoindole-1,3(2H)-dione;

27) 1-(4-bromophenyl)-2-(4-(8-chloro-5,6-dihydro-11H-benzo[5,6]cyclohepta[1,2-b]pyridin-11-ylidene)piperidin-1-yl)ethan-1-ol;

28) (2S,4R)-4-(4-(8-chloro-5,6-dihydro-11H-benzo[5,6] cyclohepta[1,2-b]pyridin-11-ylidene) piperidin-1-yl) pyrrolidine-2-carboxylic acid;

29) (S)-2-amino-3-(4-(4-(8-chloro-5,6-dihydro-11H-benzo[5,6]cyclohepta[1,2-b]pyridin -11-ylidene)piperidin-1-yl)phenyl)propionic acid dihydrochloride;

30) (4R,7S)-2-(4-(4-(8-chloro-5,6-dihydro-11H-benzo[5,6]cyclohepta[1,2-b]pyridin-11-ylidene)piperidin-1-yl) butyl)hexahydro-1H-4,7-methanoisoindole-1,3(2H)-dione;

31) ethyl(S)-2-amino-3-(4-(3-(4-(8-chloro-5,6-dihydro-11H-benzo[5,6]cyclohepta[1,2-b]pyridin-11-ylidene) piperidin-1-yl)propoxy)phenyl)propanoate trihydrochloride;

33) 3-(4-(4-(8-chloro-5,6-dihydro-11H-benzo[5,6]cyclohepta[1,2-b]pyridin-11-ylidene)piperidin-1-yl)butyl)-1H-indole-5-carbonitrile;

34) t-butyl((2S,3R)-4-(4-(8-chloro-5,6-dihydro-11H-benzo[5,6]cyclohepta[1,2-b]pyridin -11-ylidene)piperidin-1-yl)-3-hydroxy-1-phenylbutan-2-yl)carbamate;

35) (2R,3S)-3-amino-1-(4-(8-chloro-5,6-dihydro-11H-benzo[5,6]cyclohepta[1,2-b]pyridin-11-ylidene)piperidin-1-yl)-4-phenylbutan-2-ol;

36) trans-methyl 2-(-4-(4-(3-(4-(8-chloro-5,6-dihydro-11H-benzo [5,6] cyclohepta [1,2- b]pyridin-11-ylidene) piperidin-1-yl)-2-hydroxypropoxy)phenyl)cyclohexyl) acetate;

37) 2-(3-(4-(8-chloro-5,6-dihydro-11H-benzo[5,6]cyclohepta[1,2-b]pyridin-11-ylidene)piperidin-1-yl)-2-hydroxypropyl)hexahydro-1H-isoindole-1,3(2H)-dione;

38) (4R,7S)-2-(3-(4-(8-chloro-5,6-dihydro-11H-benzo[5,6]cyclohepta[1,2-b]pyridin-11-ylidene)piperidin-1-yl)-2-hydroxypropyl)hexahydro-1H-4,7-methanoisoindole-1,3(2H)-dione;

39) 6-chloro-5-(2-(4-(8-chloro-5,6-dihydro-11H-benzo[5,6]cyclohepta[1,2-b]pyridin-11-ylidene)piperidin-1-yl)ethyl)indolin-2-one;

40) trans-methyl2-(-4-(4-(4-(4-(8-chloro-5,6-dihydro-11H-benzo[5,6]cyclohepta[1,2-b]pyridin-11-ylidene) piperidin-1-yl)butoxy)phenyl)cyclohexyl)acetate;

41) trans-2-(4-(4-(3-(4-(8-chloro-5,6-dihydro-11H-benzo[5,6]cyclohepta[1,2-b]pyridin -11-ylidene)piperidin-1-yl)-2-hydroxypropoxy)phenyl)cyclohexyl)acetic acid;

42) trans-2-(4-(4-(4-(4-(8-chloro-5,6-dihydro-11H-benzo[5,6]cyclohepta[1,2-b]pyridin -11-ylidene)piperidin-1-yl)butoxy)phenyl)cyclohexyl)acetic acid;

43) (S)-2-((t-butoxycarbonyl)amino)-3-(4-(((2S,3R)-4-(4-(8-chloro-5,6-dihydro-11H -benzo[5,6]cyclohepta[1,2-b]pyridin-11-ylidene)piperidin-1-yl)-3-hydroxy-1-phenylbutan-2-yl)carbamoyl)phenyl)propionic acid;

44) (S)-2-amino-3-(4-(((2S,3R)-4-(4-(8-chloro-5,6-dihydro-11H -benzo[5,6]cyclohepta[1,2-b]pyridin-11-ylidene)piperidin-1-yl)-3-hydroxy-1-phenylbutan-2-yl)carbamoyl)phenyl)propionic acid trihydrochloride;

45) trans-2-(4-(4- (((2S,3R)-4-(4-(8-chloro-5,6-dihydro-11H-benzo[5,6]cyclohepta[1,2-b]pyridin-11-ylidene) piperidin-1-yl)-3-hydroxy-1-phenylbutan-2-yl)carbamoyl)phenyl)cyclohexyl)acetic acid;

46) N-((2S,3R)-4-(4-(8-chloro-5,6-dihydro-11H-benzo[5,6]cyclohepta[1,2-b]pyridin-11-ylidene)piperidin-1-yl)-3-hydroxy-1-phenylbutan-2-yl)-2-phenyl-5-(trifluoromethyl) oxazole-4-carboxamide;

47) (4R,7S)-2-(3-(4-(8-chloro-5,6-dihydro-11H-benzo[5,6]cyclohepta[1,2-b]pyridin-11-ylidene)piperidin-1-yl) propyl)hexahydro-1H-4,7-methanoisoindole-1,3 (2H)-dione;

49) isopropyl(S)-2-amino-3-(4-(3-(4-(8-chloro-5,6-dihydro-11H -benzo[5,6]cyclohepta[1,2-b]pyridin-11-ylidene)piperidin-1-yl)propoxy)phenyl)propanoate trihydrochloride;

50) neopentyl(S)-2-amino-3-(4-(3-(4-(8-chloro-5,6-dihydro-11H -benzo[5,6]cyclohepta[1,2-b]pyridin-11-ylidene)piperidin-1-yl)propoxy)phenyl)propanoate trihydrochloride;

51) cyclopentyl(S)-2-amino-3-(4-(3-(4-(8-chloro-5,6-dihydro-11H -benzo[5,6]cyclohepta[1,2-b]pyridin-11-ylidene)piperidin-1-yl)propoxy)phenyl)propanoate trihydrochloride;

52) 4-((3-(2-(4-(8-chloro-5,6-dihydro-11H-benzo[5,6]cyclohepta[1,2-b]pyridin-11-ylidene)piperidin-1-yl) ethyl)-2-methyl-4-oxo-6,7,8,9-tetrahydro-4H-pyrido[1,2-a]pyrimidin-9-yl)oxy)-4-oxobutanoic acid;

53) 2-((1R,4R)-4-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)cyclohexyl)acetic acid;

54) 4-(3-(4-(8-chloro-5,6-dihydro-11H-benzo[5,6]cyclohepta[1,2-b]pyridin-11-ylidene)piperidin-1-yl)-2-hydroxypropoxy)-4"-(trifluoromethoxy)-[1,1':3',1"-terphenyl]-5'-carboxylic acid;

55) (2S)-2-amino-3-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)propionic acid trihydrochloride;

56) 3-(4-(3-(4-(8-chloro-5,6-dihydro-11H-benzo[5,6]cyclohepta[1,2-b]pyridin-11-ylidene)piperidin-1-yl) propoxy)benzyl)-1-(4-fluorobenzyl)-1-(1-methylpiperidin-4-yl)urea;

57) N-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)acetamide;

58) t-butyl (4-(3-(4-(8-chloro-5,6-dihydro-11H-benzo[5,6]cyclohepta[1,2-b]pyridin-11-ylidene)piperidin-1-yl)-2-hydroxypropoxy)phenyl)carbamate;

59) N-(4-(3-(4-(8-chloro-5,6-dihydro-11H-benzo[5,6]cyclohepta[1,2-b]pyridin-11-ylidene)piperidin-1-yl)-2-hydroxypropoxy)phenyl)-2-(4-fluorophenyl)acetamide;

60) 1-(4-(8-chloro-5,6-dihydro-11H-benzo[5,6]cyclohepta[1,2-b]pyridin-11-ylidene)piperidin-1-yl)-3-(2-(3-methoxyphenethyl)phenoxy)propan-2-ol;

61) 1-(2-allylphenoxy)-3-(4-(8-chloro-5,6-dihydro-11H-benzo[5,6]cyclohepta[1,2-b]pyridin-11-ylidene)piperidin-1-yl)propan-2-ol;

62) (E)-1-(4-(8-chloro-5,6-dihydro-11H-benzo[5,6]cyclohepta[1,2-b]pyridin-11-ylidene)piperidin-1-yl)-3-(2-(3-methoxystyryl)phenoxy)propan-2-ol;

63) 9-hydroxy-3-(2-(4-(8-methoxy-5,6-dihydro-11H-benzo[5,6]cyclohepta[1,2-b]pyridin -11-ylidene)piperidin-1-yl)ethyl)-2-methyl-6,7,8,9-tetrahydro-4H-pyrido[1,2-a]pyrimidin-4-one;

64) 9-hydroxy-2-methyl-3-(2-(4-(8-methyl-5,6-dihydro-11H-benzo[5,6]cyclohepta[1,2-b]pyridin-11-ylidene) piperidin-1-yl)ethyl)-6,7,8,9-tetrahydro-4H-pyrido[1,2-a]pyrimidin-4-one;

65) 3-(2-(4-(5,6-dihydro-11H-benzo[5,6]cyclohepta[1,2-b]pyridin-11-ylidene)piperidin -1-yl) ethyl)-9-hydroxy-2-methyl-6,7,8,9-tetrahydro-4H-pyrido[1,2-a] pyrimidin-4-one;

66) (S)-2-amino-3-(4-(4-(4-(8-methoxy-5,6-dihydro-11H-benzo[5,6]cyclohepta[1,2-b]pyridin-11-ylidene) piperidin-1-yl)butoxy)phenyl)propionic acid trihydrochloride;

67) (S)-2-amino-3-(4-(4-(4-(8-methyl-5,6-dihydro-11H-benzo[5,6]cyclohepta[1,2-b]pyridin-11-ylidene)piperidin-1-yl)butoxy)phenyl)propionic acid trihydrochloride;

68) (S)-2-amino-3-(4-(4-(4-(5,6-dihydro-11H-benzo[5,6] cyclohepta[1,2-b]pyridin-11-ylidene) piperidin-1-yl) butoxy) phenyl) propionic acid trihydrochloride;

69) (4R,7S)-2-((trans-2- ((4-(8-methoxy-5,6-dihydro-11H-benzo[5,6]cyclohepta [1,2-b]pyridin-11-ylidene) piperidin-1-yl)methyl)cyclohexyl)methyl)hexahydro-1H-4,7-methanoisoindole-1,3(2H)-dione;

70) (4R,7S)-2-((trans-2-((4-(5,6-dihydro-11H-benzo[5,6] cyclohepta[1,2-b]pyridin-11-ylidene)piperidin-1-yl) methyl)cyclohexyl)methyl)hexahydro-1H-4,7-methanoisoindole-1,3(2H) -dione;

71) (4R,7S)-2-((trans-2-((4-(8-methyl-5,6-dihydro-11H-benzo[5,6]cyclohepta[1,2-b]pyridin-11-ylidene)piperidin-1-yl)methyl)cyclohexyl)methyl)hexahydro-1H-4,7-methanoisoindole-1,3(2H)-dione;

72) 2-((trans-2-((4-(8-methoxy-5,6-dihydro-11H-benzo[5,6]cyclohepta[1,2-b]pyridin-11-ylidene)piperidin-1-yl)methyl)cyclohexyl)methyl)hexahydro-1H-isoindole-1,3(2H)-dione;

73) 2-((trans-2-((4-(5,6-dihydro-11H-benzo[5,6]cyclohepta[1,2-b]pyridin-11-ylidene)piperidin-1-yl)methyl) cyclohexyl)methyl)hexahydro-1H-isoindole-1,3(2H)-dione; and 74) 2-((trans-2-((4-(8-methyl-5,6-dihydro-11H-benzo[5,6]cyclohepta[1,2-b]pyridin-11-ylidene)piperidin-1-yl) methyl)cyclohexyl)methyl)hexahydro-1H-isoindole-1,3(2H)-dione.

3. A method for treating diseases associated with serotonin 2A (5-HT2A) activation, including administering the compound of claim 1 to a subject in need thereof wherein the diseases associated with serotonin 2A (5-HT2A) activation is a metabolic disease or cancer, and wherein the metabolic disease is selected from the group consisting of obesity, diabetes, hyperlipidemia, arteriosclerosis, fatty liver, steatohepatitis, fibrosis, and hypertension, and the cancer is selected from the group consisting of colon cancer, breast cancer, and ovarian cancer.

4. A method for inhibiting the activity of serotonin 2A (5-HT2A), including administering the compound of claim 1 to a subject in need thereof.

5. A method for treating diseases associated with serotonin 2A (5-HT2A) activation, including administering the following compound to a subject in need thereof:

8-chloro-11-(1-methylpiperidin-4-ylidene)-6, 11-dihydro-5H-benzo[5,6]cyclohepta[1,2-b]pyridine, wherein the diseases associated with serotonin 2A (5-HT2A) activation is a metabolic disease, selected from the group consisting of obesity, diabetes, hyperlipidemia, arteriosclerosis, fatty liver, steatohepatitis, fibrosis, and hypertension.

6. A method for treating diseases associated with serotonin 2A (5-HT2A) activation, including administering the compound of claim 2 to a subject in need thereof;

wherein the diseases associated with serotonin 2A (5-HT2A) activation is a metabolic disease selected from the group consisting of obesity, diabetes, hyperlipidemia, arteriosclerosis, fatty liver, steatohepatitis, fibrosis, and hypertension, or a cancer selected from the group consisting of colon cancer, breast cancer, and ovarian cancer.

7. A method for inhibiting the activity of serotonin 2A (5-HT2A), including administering the compound of claim 2 to a subject in need thereof.

* * * * *